United States Patent [19]

Dahlberg et al.

[11] Patent Number: 5,541,311

[45] Date of Patent: Jul. 30, 1996

[54] NUCLEIC ACID ENCODING SYNTHESIS-DEFICIENT THERMOSTABLE DNA POLYMERASE

[75] Inventors: James E. Dahlberg; Victor I. Lyamichev; Mary Ann D. Brow, all of Madison, Wis.

[73] Assignee: Third Wave Technologies, Inc., Monrovia, Calif.

[21] Appl. No.: 73,384

[22] Filed: Jun. 4, 1993

Related U.S. Application Data

[63] Continuation-in-part of Ser. No. 986,330, Dec. 7, 1992, abandoned.

[51] Int. Cl.⁶ .............................. C12N 1/21; C12N 15/00; C07H 21/00; C07H 21/04
[52] U.S. Cl. ................... 536/23.7; 435/320.1; 435/252.8
[58] Field of Search ...................... 435/6, 69.1, 172.3, 435/320.1; 530/350; 536/23.7; 935/10, 24, 72

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,108,892 | 4/1992 | Burke et al. | 435/6 |
| 5,144,019 | 9/1992 | Rossi et al. | 536/27 |
| 5,210,015 | 5/1993 | Gelfand et al. | 435/6 |

FOREIGN PATENT DOCUMENTS

| | | | |
|---|---|---|---|
| 0482714 | 4/1992 | European Pat. Off. | C12N 15/54 |
| WO91/09950 | 7/1991 | WIPO | C12N 1/21 |
| 92/02638 | 2/1992 | WIPO | C12Q 1/68 |
| 92/06200 | 4/1992 | WIPO | C12N 15/54 |

OTHER PUBLICATIONS

Kunkel, Thomas A. Rapid and efficient site specific mutagenesis without phenotypic selection. Proc. Natl. Acad. Sci. USA. (Jan. 1985) 82:488–492.

European Patent 482714 (Abs) to Eastman Kodak Co. published Apr. 29, 1992. Mutant *Thermus aquaticus*DNA polymerase genes–used for producing thermostable . . . .

J. Marmur et al., "Strand Separation and Specific Recombination in Deoxyribonucleic Acids: Biological Studies," Proc. Natl. Acad. Sci. USA 46:453 (1960).

P. Doty et al., "Strand Separation and Specific Recombination in Deoxyribonucleic Acids: Physical Chemical Studies," Proc. Natl. Acad. Sci. USA 46:461 (1960).

M. Hayashi et al., "Restriction of In Vivo Genetic Transcription to One of the Complementary Strands of DNA," Proc. Natl. Acad. Sci. USA 50:664 (1963).

H. Smith et al., "A Restriction Enzyme from *Hemophilus influenza*," J. Mol. Biol. 51:379 (1970).

E. Southern, "Detection of Specific Sequences Among DNA Fragments Separated by Gel Electrophoresis," J. Mol Biol. 98:503 (1975).

R. Wallace et al., "Application of Synthetic Oligonucleotides to the Diagnosis of Human Genetic Diseases," Biochimie 67:755 (1985).

A. Studencki et al., "Allele–Specific Hybridization Using Oligonucleotide Probes of Very High Specific Activity: Discrimination of the Human $\beta^A$–and $\beta^S$–Globin Genes," DNA 3:7 (1984).

A. Studencki et al., "Discrimination among the Human $\beta^a$, $\beta$hu S, and $\beta^c$–Globin Genes Using Allele–Specific Oligonucleotide Hybridization Probes," Am. J. Human Genetics 37:42 (1985).

(List continued on next page.)

*Primary Examiner*—Margaret Parr
*Assistant Examiner*—David Schreiber
*Attorney, Agent, or Firm*—Medlen & Carroll

[57] ABSTRACT

A means for cleaving a nucleic acid cleavage structure in a site-specific manner is disclosed. A cleaving enzyme having 5' nuclease activity without interfering nucleic acid synthetic ability is employed as the basis of a novel method of detection of specific nucleic acid sequences. Cleaving enzymes are produced through the use of novel DNA sequences which encode novel thermostable polymerases.

9 Claims, 32 Drawing Sheets

Genes for Wild-Type and Pol(-) DNAPTaq

OTHER PUBLICATIONS

R. Saiki, "The Design and Optimization of the PCR," *PCR Technology*—Principles and Applications for DNA Amplification(H. A. Erlich, Ed.), Stockton Press, New York, pp. 7–19 (1989).

P. Holland et al., "Detection of Specific Polymerase Chain Reaction Product by Utilizing the 5'–3' Exonuclease Activity of *Thermus aquaticus* DNA Polymerase," Proc. Natl. Acad. Sci. USA 88:7276 (1991).

R. Wallace et al., "Hybridization of Synthetic Oligodeoxyribonucleotides to $\Phi_x$ 174 DNA:the Effect of Single Base Pair Mismatch," Nucl. Acids Res. 6:3543 (1979).

R. Wallace et al., "The Use of Oligonucleotides as Hybridization Probes. II. Hybridization of Oligonucleotides of Mixed Sequence to Rabbit β–Globin DNA," Nucl. Acids Res. 9:879 (1981).

R. Saiki et al., "Analysis of Enzymatically Amplified β–globin and HLA–DQα DNA with Allele–Specific Oligonucleotide Probes," Nature 324:163 (1986).

S. Kwok et al., "Effects of Primer–Template Mismatches on the Polymerase Chain Reaction: Human Immunodeficiency Virus Type I Model Studies," Nucl. Acids Res. 18:999 (1990).

A. Kornberg, *DNA Replication*, W. H. Freeman and Co., San Francisco, pp. 127–139 (1980).

K. Tindall et al., "Fidelity of DNA Synthesis by the *Thermus aquaticus* DNA Polymerase," Biochem. 27:6008 (1988).

D. Brutlag et al., "An Active Fragment of DNA Polymerase Produced by Proteolytic Cleavage," Biochem. Biophys. Res. Commun. 37:982 (1969).

H. Erlich et al., "Recent Advances in the Polymerase Chain Reaction," Science 252:1643 (1991).

P. Setlow et al., "Deoxyribonucleic Acid Polymerase: Two Distinct Enzymes in One Polypeptide–II. A Proteolytic Fragment Containing the 5'–3' Exonuclease Function. Restoration of Intact Enzyme Functions from the Two Proteolytic Fragments," J. Biol. Chem. 247:232 (1972).

D. Gelfand, "*Taq* DNA Polymerase," *PCR Technology—Principles and Applications for DNA Amplification (H. A. Erlich, Ed.)*, Stockton Press, New York, p. 19 (1989).

F. Lawyer et al., "Isolation, Characterization, and Expression in *Escherichia coli* of the DNA Polymerase Gene from *Thermus aquaticus*," J. Biol. Chem. 264:6427 (1989).

A. Akhmetzjanov et al., "Molecular Cloning and Nucleotide Sequence of the DNA Polymerase Gene from *Thermus flavus*," Nucl. Acids Res. 20:5839 (1992).

P. Setlow et al., "Deoxyribonucleic Acid Polymerase: Two Distinct Enzymes in One Polypeptide—I. A Proteolytic Fragment Containing the Polymerase and 3'–5' Exonuclease Functions," J. Biol. Chem. 247:224 (1972).

R. Saiki et al., " Primer–Directed Enzymatic Amplification of DNA with a Thermostable DNA Polymerase," Science 239:487 (1988).

K. Mullis et al., "Specific Synthesis of DNA *in Vitro* via a Polymerase–Catalyzed Chain Reaction," *Methods in Enzymology* 155:335 (1987).

F. Perler et al., "Intervening Sequences in an Archaea DNA Polymerase Gene," Proc. Natl. Acad. Sci. USA 89:5577 (1992).

A. Kaledin et al., "Isolation and Properties of DNA Polymerase from the Extremely Thermophilic Bacterium *Thermus Flavus*," Biokhimiya 46:1576 (1981).

N. Carballeira et al., "Purification of a Thermostable DNA Polymerase from *Thermus thermophilus* HB8, Useful in the Polymerase Chain Reaction," BioTechniques 9:276 (1990).

T. Myers et al., "Reverse Transcripton and DNA Amplification by a *Thermus thermophilus* DNA Polymerase," Biochem. 30:7661 (1991).

J. Ito et al., "Compilation and Alignment of DNA Polymerase Sequences," Nucl. Acids Res. 19:4045 (1991).

E. Mathur et al., "The DNA Polymerase Gene from the Hyperthermophilic Marine Archaebacterium, *Pyrococcus furiosus*, Shows Sequence Homology with α–like DNA Polymerases," Nucl. Acids. Res. 19:6952 (1991).

J. Dunn et al. "Complete Nucleotide Sequence of Bacteriophage T7 DNA and the Locations of T7 Genetic Elements," J. Mol. Biol. 166:477 (1983).

V. Antao et al., "A Thermodynamic Study of Unusually Stable RNA and DNA Hairpins," Nucl. Acids Res. 19:5901 (1991).

M. Stark, "Multicopy Expression Vectors Carrying the *lac* Repressor Gene for Regulated High–Level Expression of Genes in *Escherichia coli*," Gene 5:255 (1987).

F. Studier et al., "Use of Bacteriophage T7 RNA Polymerase to Direct Selective High–level Expression of Cloned Genes," J. Mol. Biol. 189:113 (1986).

D. Englke et al., "Purification of *Thermus aquaticus* DNA Polymerase Expressed in *Escherichia coli*," Anal. Biochem 191:396 (1990).

M. Orita et al., "Rapid and Simple Detection of Point Mutations and DNA Polymorphisms Using the Polymerase Chain Reactions," Genomics 5:874 (1989).

K. Hayashi, "PCR–SSCP: A Simple and Sensitive Method for Detection of Mutations in the Genomic DNA," PCR Meth. and Appl. 1:34 (1991).

M. Bergseid et al., "A High Fidelity Thermostable DNA Polymerase Isolated from *Pyrococcus furiosus*," Strategies (Stratagene, LaJolla, CA 4:34 (1991).

R. Kelly et al., "Excision of Thymine Dimers and Other Mismatched Sequences by DNA Polymerase of *Escherichia coli*," Nature 244:495 (1969).

A. Kornberg et al., "Enzymatic Synthesis of Deoxyribonucleic Acid, XVL Oligonucleotides as Templates and the Mechanism of Their Replication," Biochemistry 51:315 (1961).

A. Kornberg, "DNA Polymerases —A Perspective," The Enzymes, vol. XIV:3.

I. Lehman, "DNA Polymerase I of *Escherichia coli*," The Enzymes, vol. XIV:15.

P. Lopez et al., "Characterization of the polA Gene of *Streptococcus pneumoniae* and Comparison of the DNA Polymerase I It Encodes to Homologous Enzymes from *Escherichia coli* and Phage T7," J. Biol. Chem. 264:4255 (1989).

H. Schachman et al., "Enzymatic Synthesis of Deoxyribonucleic Acid," J. Biol. Chem. 235:3242 (1960).

R. Lundquist et al., "Transient Generation of Displaced Single–Stranded DNA During Nick Translation," Cell 31:53 (1982).

M. Innis et al., "DNA Sequencing with *Thermus aquaticus* DNA Polymerase and direct Sequencing of Polymerase Chain Reaction–Amplified DNA," Proc. Natl. Acad. Sci. USA 85:9436 (1988).

Perkin Elmer Cetus, Product Analysis: "AmpliTaq DNA Polymerase".

Promega, Product Analysis: "Taq DNA Polymerase", Certificate of Analysis.

M. Longley et al., "Characterization of the 5' to 3' Exonuclease Associated with *Thermus aquaticus* DNA Polymerase," Nucl. Acids Res. 18:7317 (1990).

Y. Li et al., "Targeted Cleavage of mRNA *in vitro* by RNase P from *Escherichia coli*," Proc. Natl. Acad. Sci. USA 89:3185 (1992).

A. Podhajska et al., "Conversion of the *FokI* Endonuclease to a Universal Restriction Enzyme: Cleavage of Phage M13mp7 DNA at Predetermined Sites," Gene 40:175 (1985).

R. Symons, "Small Catalytic RNAs," Annu. Rev. Biochem. 61:641 (1992).

D. Lilley et al., "Cruciform–Resolvase Interactions in Supercoiled DNA," Cell 36:413 (1984).

S. Chow et al., "Reversal of Integration and DNA Splicing Mediated by Integrase of Human Immunodeficiency Virus," Science 255:723 (1992).

F. Lawyer et al., "High-level Expression, Purification, and Enzymatic Characterization of Full-length *Thermus aquaticus* DNA Polymerase and a Truncated Form Deficient in 5' to 3' Exonuclease Activity," PCR Meth. and Appl. 2:275 (1993).

V. Lyamichev et al., "Structure–Specific Endonucleolytic Cleavage of Nucleic Acids by Eubacterial DNA Polymerases," Science 260:778 (1993).

D. Duckett et al., "The Structure of DNA Junctions and their Interaction with Enzymes," Eur. J. Biochem. 207:285 (1992).

J. Sambrook, et al. *Molecular Cloning*, Cold Spring Harbor Laboratory Press, Cold Spring Harbor, pp. 1.63–1.69 (1989).

A. Kornberg, et al., DNA Replication (2d ed.) w. H. Freeman and Co., San Francisco, pp. 403–414 (1992).

PART ONE: TRIGGER REACTION

PART TWO: DETECTION REACTION

FIG. 2A

```
MAJORITY [SEQ ID NO:7] ATCXXGGGATGCTTCCCCTCTTGAGCCCAAAGGCCCGGTCCTCGTGGAGCGGCCACCACCTGGCCT      70

DNAPTAQ  [SEQ ID NO:1]  ...AG..G..........G.....................................              70
DNAPTFL  [SEQ ID NO:2]  ......................C..C..........C..G..........                    67
DNAPTTH  [SEQ ID NO:3]  ...GA.................G....A.........................                 70

MAJORITY                ACGGCACCTTCTTCGCCCTGAAGGGCCTCACCCAGCCGGGGGGAACCGGTCCAGGCCGGTCTACGGCTT  140

DNAPTAQ                 ..............CA.............................G..G....................   140
DNAPTFL                 ...............A......T........C............................C..T....    137
DNAPTTH                 ......................G...............G..............................   140

MAJORITY                CGCCAAGAGCCTCCTCAAGGCCCTGAAGGAGGACGGGGACGCGGTCCTTGTCGTTTGACGCCAAG        207

DNAPTAQ                 ..............C........................A......                           204
DNAPTFL                 ...............A..............GT..T........-                             210
DNAPTTH                 .......................T..AA...C..CT.........

MAJORITY                CGCCCCCTCCTTCCGCCACGAGCCTACGAGCCTACAAGCCCGGGGCCCCCACCCCGAGGACTTC         277

DNAPTAQ                 ...........G..........G..GG........G..................                   274
DNAPTFL                 .....................GA..........G.......C........                       280
DNAPTTH                 .......................................................

MAJORITY                CCGGCCAGCTCGCCCTCATCAAGCCAGCTGGTGGACCTCCTGGGGCTTGCCGCCCTCCGAGGTCCCCGGCTA  347

DNAPTAQ                 ......A...................................G........                     344
DNAPTFL                 ......G..................T........A..C...T..G..T...                      350
DNAPTTH                 ...............................T..A..C..........                         
```

FIG. 2B

```
MAJORITY [SEQ ID NO:7]  CGAGGCGGAGGACGTXCTGGCCACCCTGGCCAAGAAGCGGGAAAAAGCGAGGGTACGAGGTGGGCATGCTC

DNAPTAQ  [SEQ ID NO:1]  ............................G..................C...........C........   417
DNAPTFL  [SEQ ID NO:2]  T............G..................CG...................................   414
DNAPTTH  [SEQ ID NO:3]  .............T..C...............................................        420

MAJORITY  ACCGCCGACCCGGACCTCTACCAGCTCCTTTCCACCCGCATCCCCTCCTCCACCCGAGGGGTACCTGA

DNAPTAQ  ......AAA.....T.................CA...................................     487
DNAPTFL  ...T..........................G.G....A..................T............    484
DNAPTTH  ..............A..G.C.....G....................CC......                    490

MAJORITY  TCACCCCGGCGTGGCTTTGGGAGAAGTACGGCCTGAGGCCCGACCAGTGGGTGGACTACCGGGCCCTGGC

DNAPTAQ  ............C..............A................C..C..........CC.......A.    557
DNAPTFL  ....T........AC...................................C..C................   554
DNAPTTH  .....A...............................C..............T...C.....C.T       560

MAJORITY  GGGGGACCCCCTCCGAGAACCTCCCCGGGGTCAAGGGCATCGGGGAGAGACCCCXGAAGCTCCTCXAG

DNAPTAQ  C.....GAG....T..........G........................G.GAG.....T..GG...    627
DNAPTFL  .......G.T...A...........G.................................A..G..A..CGG  624
DNAPTTH  .......A....................................................TC.........A..  630

MAJORITY  GAGTGGGGGAGCCCTGGAAAAACCTCCTCAAGAACCTGGACCGGGGTGAAGCCCGC---CXTCGGGGAGAAGA

DNAPTAQ  .....................GC...............C..................A........      694
DNAPTFL  ..................................T..C.C......A......T..T.G..........C..  691
DNAPTTH  ....A.............................................A......A.AAAA.G.        700
```

FIG. 2C

Sequence alignment figure showing nucleotide sequences for MAJORITY [SEQ ID NO:7], DNAPTAQ [SEQ ID NO:1], DNAPTFL [SEQ ID NO:2], and DNAPTTH [SEQ ID NO:3], with position numbers 764/761/770, 834/831/840, 904/901/910, 974/971/980, and 1044/1041/1050.

```
                                                                    2499
                                                                    2496
                                                                    2505
MAJORITY [SEQ ID NO:7]  GCCCCTGGAGGTGGAGGTGGGGATGGGGAGGACTGGCTCTCCGCCAAGGAGTAG

DNAPTAQ  [SEQ ID NO:1]  ..........A..........................................GA
DNAPTFL  [SEQ ID NO:2]  ...............CC.....................................
DNAPTTH  [SEQ ID NO:3]  .............................................T........GT..
```

FIG. 3A

```
MAJORITY [SEQ ID NO:8]   MXAMLPLFEPKGRVLLVDGHHLAYRTFFALKGLTTSRGEPVQAVYGFAKSLLKALKEDG-DAVXVVFDAK

TAQ PRO  [SEQ ID NO:4]   ..RG.................H.................................I.........    69
TFL PRO  [SEQ ID NO:5]   -.-..................................................-.V.........    68
TTH PRO  [SEQ ID NO:6]   ..E.................................................YK..F........    70

MAJORITY                 APSFRHEAYEAYKAGRAPTPEDFPRQLALIKELVDLLGLXRLEVPGYEADDVLATLAKKAEKEGYEVRIL

TAQ PRO                  ..........GG........................A.......................S........   139
TFL PRO                  ....................................V....F..................R........   138
TTH PRO                  ...........................................FT.......................   140

MAJORITY                 TADRDLYQLLSDRIAVLHPEGYLITPAWLWEKYGLRPEQWVDYRALXGDPSNLPGVKGIGEKTAXKLLX

TAQ PRO                  ....K............................................D..A......T..E.....R...E   209
TFL PRO                  ..................E..I............Y..................A......I........QR.IR   208
TTH PRO                  ...............V..V.........H..E.....................F..V............L...K   210

MAJORITY                 EWGSLENLLKNLDRVKP-XXREKIXAHMEDLXLSXXLSXVRTDLPLEVDFAXRREPDREGLRAFLERLEF

TAQ PRO                  ..........A...........AI....L...D..K..WD.AK....................K.......R........   278
TFL PRO                  ....FQH..Q...SL...LQ.G..A.A..RK..Q.H..............GR.T.NL...................   277
TTH PRO                  ....ENV...K.L...R..LE..R.......K.L...R..LE..R.............L.QG................   280

MAJORITY                 GSLLHEFGLLEXPKALEEAPWPPEGAFVGFVLSRPEPMWAELLALAAARXGRVHRAXDPLXGLRDLKEV

TAQ PRO                  ......S.................................K......D.............G........PE..YKA......A   348
TFL PRO                  ..G..A...................L..SF.................................G.WE..L...Q....R......G...   347
TTH PRO                  ..A.AP......................................K..C.D.........A...A..K.........   350
```

FIG. 3B

```
MAJORITY  [SEQ ID NO:8]  RGLLAKDLAVLALREGLDLXPGDDPMLLAYLLDPSNTTPEGVARRYGGEWTEDAGERALLSERLFXNLXX

TAQ PRO   [SEQ ID NO:4]  ..................S............G.P...............E...........A..WG  418
TFL PRO   [SEQ ID NO:5]  ..................I...........F.E................A......QT.KE     417
TTH PRO   [SEQ ID NO:6]  ................S..............V.................AH......HR..LK    420

MAJORITY  RLEGEERLLWLYXEVEKPLSRVLAHMEATGVRLDVAYLQALSLEVAEEIRRLEEEVFRLAGHPFNLNSRD

TAQ PRO   ..................R...R...A.............R..........................  488
TFL PRO   ...K............E......R..........EA.V.Q.......L...................  487
TTH PRO   ...K....H..........................................................  490

MAJORITY  QLERVLFDELGLPAIGKTEKTGKRSTSAAVLEALREAHPIVEKILQYRELTKLKNTYIDPLPXLVHPRTG

TAQ PRO   ................................DR..........S.............D.I......  558
TFL PRO   .........R..L..Q...........................H................A...K..  557
TTH PRO   .....................................................V..S..........  560

MAJORITY  RLHTRFNQTATATGRLSSSDPNLQNIPVRTPLGQRIRRAFVAEEGWXLVALDYSQIELRVLAHLSGDENL

TAQ PRO   ....................................I........L....V.V..............  628
TFL PRO   ............................................A.A...................  627
TTH PRO   ....................................................................  630

MAJORITY  IRVFQEGRDIHTQTASWMFGVPPEAVDPLMRRAAKTINFGVLYGMSAHRLSQELAIPYEEAVAFIERYFQ

TAQ PRO   ................E...............R..................Q..............  698
TFL PRO   .................................S..G..............G..S...........  697
TTH PRO   ...K..............................V................................  700
```

FIG. 3C

```
MAJORITY [SEQ ID NO:8]  SFPKVRAWIEKTLEEGRRRGYVETLFGRRRYVPDLNARVKSVREAAERMAFNMPVQGTAADLMKLAMVKL

TAQ PRO  [SEQ ID NO:4]  ..........................E.........................................  768
TFL PRO  [SEQ ID NO:5]  .Y......G...........................................R..............  767
TTH PRO  [SEQ ID NO:6]  ...............K....................................................  770

MAJORITY                FPRLXEMGARMLLQVHDELVLEAPKXRAEXVAALAKEVMEGVYPLAVPLEVEVGXGEDWLSAKEX

TAQ PRO                 ....E.............E...A..R.................I....................    833
TFL PRO                 ....Q.L...........D...R.........W..Q................L...........    831
TTH PRO                 ....R............QA...E......L...A..KA..............M.........G.    835
```

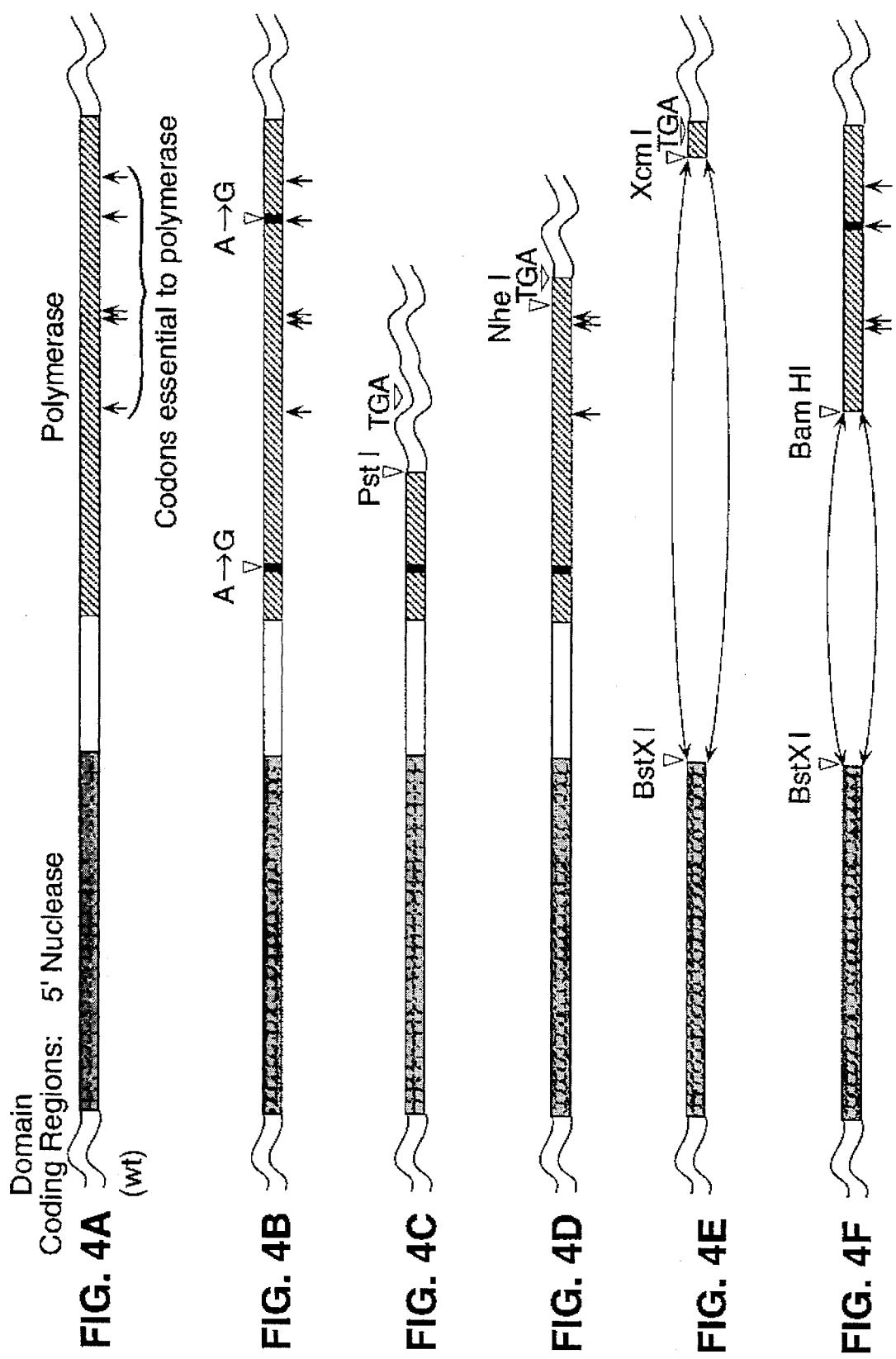

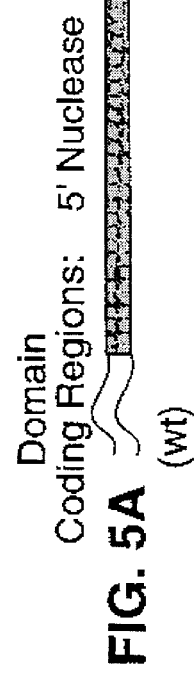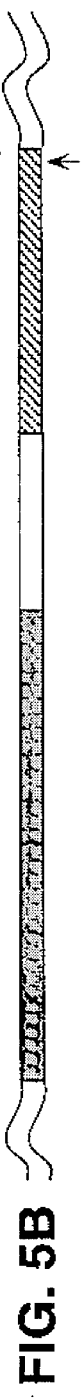
FIG. 5A
FIG. 5B

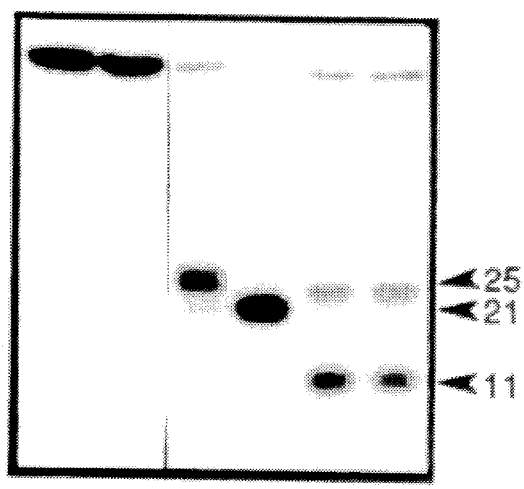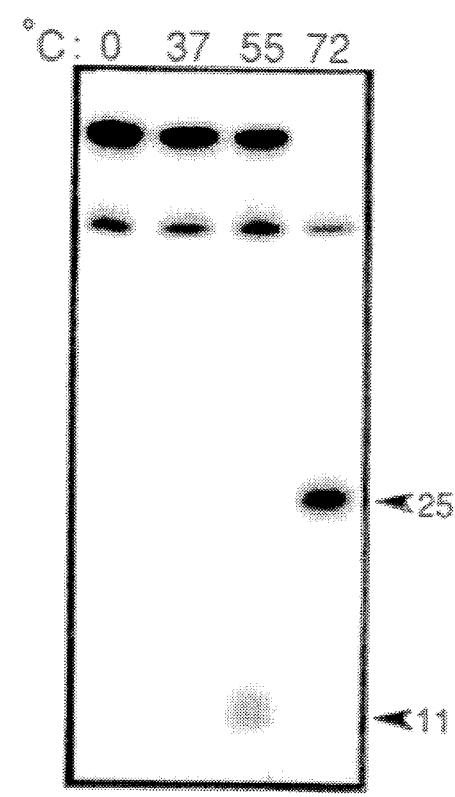
FIG. 9A
FIG. 9B

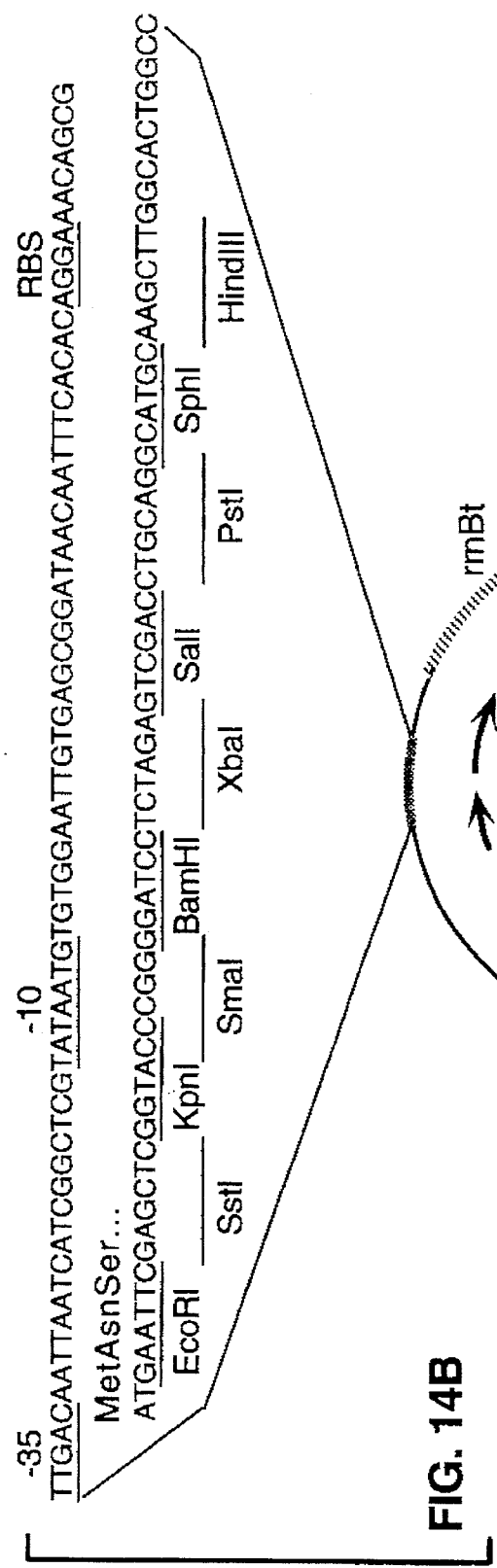
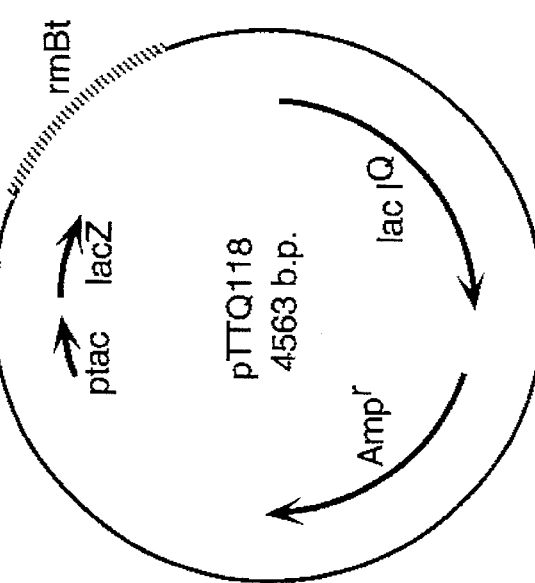
FIG. 14A
FIG. 14B
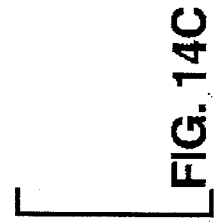
RBS: Ribosome binding site
ptac: Synthetic tac promoter
lac IQ: Lac repressor gene
lacZ: Beta-galactosidase alpha fragment
rrnBt: E. coli rrnB transcription terminator
FIG. 14C

P$_{\phi 10}$: Bacteriophage T7 φ10 promoter  RBS: Ribosome binding site
T$_\phi$: T7 φ Terminator

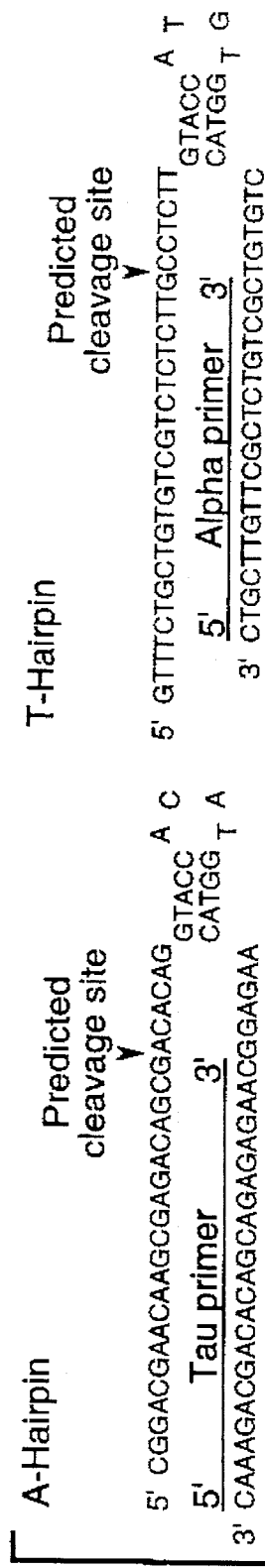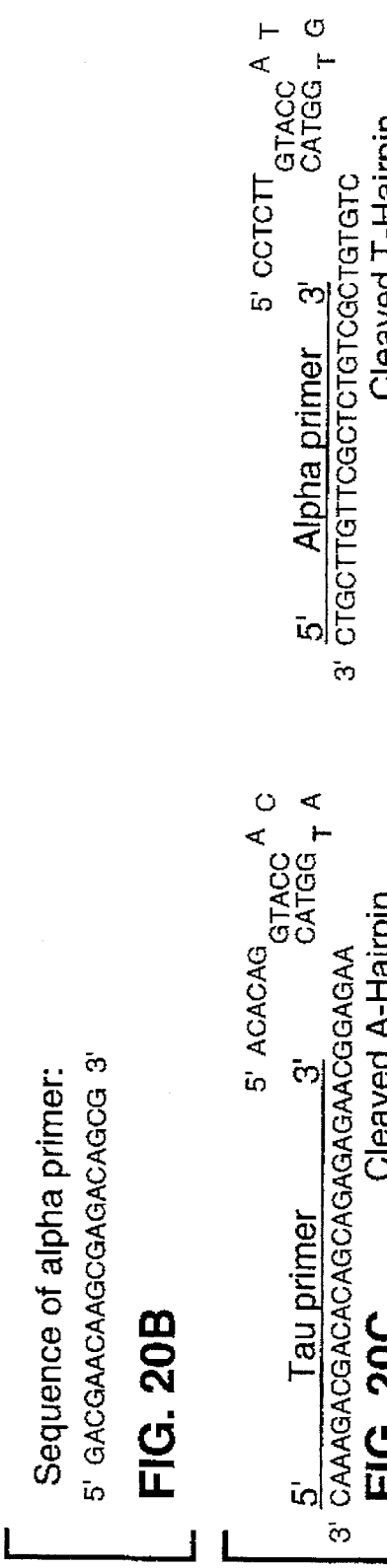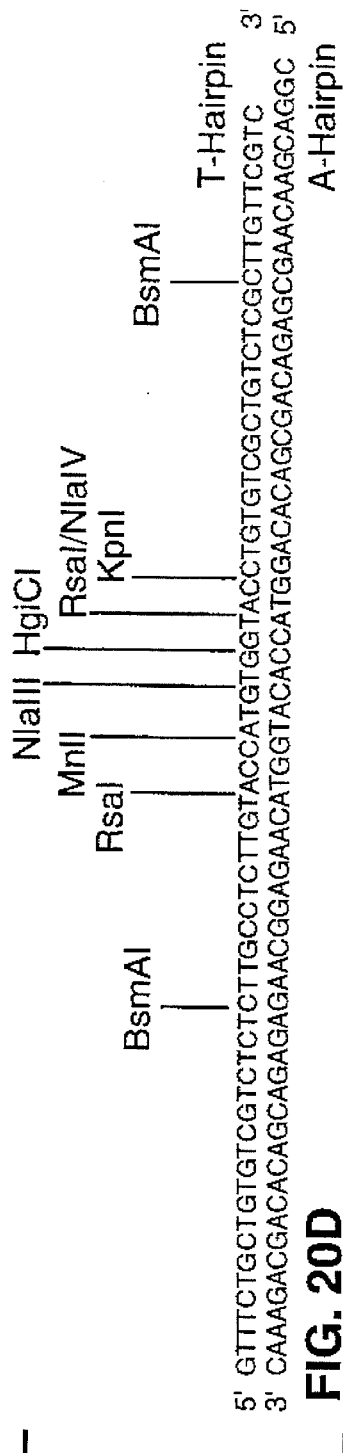

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 2506 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ATGAGGGGGA  TGCTGCCCCT  CTTTGAGCCC  AAGGGCCGGG  TCCTCCTGGT  GGACGGCCAC    60

CACCTGGCCT  ACCGCACCTT  CCACGCCCTG  AAGGGCCTCA  CCACCAGCCG  GGGGGAGCCG   120

GTGCAGGCGG  TCTACGGCTT  CGCCAAGAGC  CTCCTCAAGG  CCCTCAAGGA  GGACGGGGAC   180

GCGGTGATCG  TGGTCTTTGA  CGCCAAGGCC  CCCTCCTTCC  GCCACGAGGC  CTACGGGGGG   240

TACAAGGCGG  GCCGGGCCCC  CACGCCGGAG  GACTTTCCCC  GGCAACTCGC  CCTCATCAAG   300

GAGCTGGTGG  ACCTCCTGGG  GCTGGCGCGC  CTCGAGGTCC  CGGGCTACGA  GGCGGACGAC   360

GTCCTGGCCA  GCCTGGCCAA  GAAGGCGGAA  AAGGAGGGCT  ACGAGGTCCG  CATCCTCACC   420

GCCGACAAAG  ACCTTTACCA  GCTCCTTTCC  GACCGCATCC  ACGTCCTCCA  CCCCGAGGGG   480

TACCTCATCA  CCCCCGGCCTG  GCTTTGGGAA  AAGTACGGCC  TGAGGCCCGA  CCAGTGGGCC   540

GACTACCGGG  CCCTGACCGG  GGACGAGTCC  GACAACCTTC  CCGGGGTCAA  GGGCATCGGG   600

GAGAAGACGG  CGAGGAAGCT  TCTGGAGGAG  TGGGGGAGCC  TGGAAGCCCT  CCTCAAGAAC   660

CTGGACCGGC  TGAAGCCCGC  CATCCGGGAG  AAGATCCTGG  CCCACATGGA  CGATCTGAAG   720

CTCTCCTGGG  ACCTGGCCAA  GGTGCGCACC  GACCTGCCCC  TGGAGGTGGA  CTTCGCCAAA   780

AGGCGGGAGC  CCGACCGGGA  GAGGCTTAGG  GCCTTTCTGG  AGAGGCTTGA  GTTTGGCAGC   840

CTCCTCCACG  AGTTCGGCCT  TCTGGAAAGC  CCCAAGGCCC  TGGAGGAGGC  CCCCTGGCCC   900

CCGCCGGAAG  GGGCCTTCGT  GGGCTTTGTG  CTTTCCCGCA  AGGAGCCCAT  GTGGGCCGAT   960

CTTCTGGCCC  TGGCCGCCGC  CAGGGGGGGC  CGGGTCCACC  GGGCCCCCGA  GCCTTATAAA  1020

GCCCTCAGGG  ACCTGAAGGA  GGCGCGGGGG  CTTCTCGCCA  AAGACCTGAG  CGTTCTGGCC  1080

CTGAGGGAAG  GCCTTGGCCT  CCCGCCCGGC  GACGACCCCA  TGCTCCTCGC  CTACCTCCTG  1140
```

-continued

| | | | | | |
|---|---|---|---|---|---|
|GACCCTTCCA|ACACCACCCC|CGAGGGGGTG|GCCCGGCGCT|ACGGCGGGGA|GTGGACGGAG|1200|
|GAGGCGGGGG|AGCGGGCCGC|CCTTTCCGAG|AGGCTCTTCG|CCAACCTGTG|GGGGAGGCTT|1260|
|GAGGGGGAGG|AGAGGCTCCT|TTGGCTTTAC|CGGGAGGTGG|AGAGGCCCCT|TTCCGCTGTC|1320|
|CTGGCCCACA|TGGAGGCCAC|GGGGGTGCGC|CTGGACGTGG|CCTATCTCAG|GGCCTTGTCC|1380|
|CTGGAGGTGG|CCGAGGAGAT|CGCCCGCCTC|GAGGCCGAGG|TCTTCCGCCT|GGCCGGCCAC|1440|
|CCCTTCAACC|TCAACTCCCG|GGACCAGCTG|GAAAGGGTCC|TCTTTGACGA|GCTAGGGCTT|1500|
|CCCGCCATCG|GCAAGACGGA|GAAGACCGGC|AAGCGCTCCA|CCAGCGCCGC|CGTCCTGGAG|1560|
|GCCCTCCGCG|AGGCCCACCC|CATCGTGGAG|AAGATCCTGC|AGTACCGGGA|GCTCACCAAG|1620|
|CTGAAGAGCA|CCTACATTGA|CCCCTTGCCG|GACCTCATCC|ACCCCAGGAC|GGGCCGCCTC|1680|
|CACACCCGCT|TCAACCAGAC|GGCCACGGCC|ACGGGCAGGC|TAAGTAGCTC|CGATCCCAAC|1740|
|CTCCAGAACA|TCCCCGTCCG|CACCCCGCTT|GGGCAGAGGA|TCCGCCGGGC|CTTCATCGCC|1800|
|GAGGAGGGGT|GGCTATTGGT|GGCCCTGGAC|TATAGCCAGA|TAGAGCTCAG|GGTGCTGGCC|1860|
|CACCTCTCCG|GCGACGAGAA|CCTGATCCGG|GTCTTCCAGG|AGGGGCGGGA|CATCCACACG|1920|
|GAGACCGCCA|GCTGGATGTT|CGGCGTCCCC|CGGGAGGCCG|TGGACCCCCT|GATGCGCCGG|1980|
|GCGGCCAAGA|CCATCAACTT|CGGGGTCCTC|TACGGCATGT|CGGCCCACCG|CCTCTCCCAG|2040|
|GAGCTAGCCA|TCCCTTACGA|GGAGGCCCAG|GCCTTCATTG|AGCGCTACTT|TCAGAGCTTC|2100|
|CCCAAGGTGC|GGGCCTGGAT|TGAGAAGACC|CTGGAGGAGG|GCAGGAGGCG|GGGGTACGTG|2160|
|GAGACCCTCT|TCGGCCGCCG|CCGCTACGTG|CCAGACCTAG|AGGCCCGGGT|GAAGAGCGTG|2220|
|CGGGAGGCGG|CCGAGCGCAT|GGCCTTCAAC|ATGCCCGTCC|AGGGCACCGC|CGCCGACCTC|2280|
|ATGAAGCTGG|CTATGGTGAA|GCTCTTCCCC|AGGCTGGAGG|AAATGGGGGC|CAGGATGCTC|2340|
|CTTCAGGTCC|ACGACGAGCT|GGTCCTCGAG|GCCCCAAAAG|AGAGGGCGGA|GGCCGTGGCC|2400|
|CGGCTGGCCA|AGGAGGTCAT|GGAGGGGGTG|TATCCCCTGG|CCGTGCCCCT|GGAGGTGGAG|2460|
|GTGGGGATAG|GGGAGGACTG|GCTCTCCGCC|AAGGAGTGAT|ACCACC| |2506|

(2) INFORMATION FOR SEQ ID NO:2:

(i) SEQUENCE CHARACTERISTICS:
        (A) LENGTH: 2496 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

| | | | | | |
|---|---|---|---|---|---|
|ATGGCGATGC|TTCCCCTCTT|TGAGCCCAAA|GGCCGCGTGC|TCCTGGTGGA|CGGCCACCAC|60|
|CTGGCCTACC|GCACCTTCTT|TGCCCTCAAG|GGCCTCACCA|CCAGCCGCGG|CGAACCCGTT|120|
|CAGGCGGTCT|ACGGCTTCGC|CAAAAGCCTC|CTCAAGGCCC|TGAAGGAGGA|CGGGGACGTG|180|
|GTGGTGGTGG|TCTTTGACGC|CAAGGCCCCC|TCCTTCCGCC|ACGAGGCCTA|CGAGGCCTAC|240|
|AAGGCGGGCC|GGGCCCCCAC|CCCGGAGGAC|TTTCCCCGGC|AGCTGGCCCT|CATCAAGGAG|300|
|TTGGTGGACC|TCCTAGGCCT|TGTGCGGCTG|GAGGTTCCCG|GCTTTGAGGC|GGACGACGTG|360|
|CTGGCCACCC|TGGCCAAGCG|GGCGGAAAAG|GAGGGGTACG|AGGTGCGCAT|CCTCACTGCC|420|
|GACCGCGACC|TCTACCAGCT|CCTTTCGGAG|CGCATCGCCA|TCCTCCACCC|TGAGGGGTAC|480|
|CTGATCACCC|CGGCGTGGCT|TTACGAGAAG|TACGGCCTGC|GCCCGGAGCA|GTGGGTGGAC|540|
|TACCGGGCCC|TGGCGGGGGA|CCCCTCGGAT|AACATCCCCG|GGGTGAAGGG|CATCGGGGAG|600|
|AAGACCGCCC|AGAGGCTCAT|CCGCGAGTGG|GGGAGCCTGG|AAAACCTCTT|CCAGCACCTG|660|

```
GACCAGGTGA  AGCCCTCCTT  GCGGGAGAAG  CTCCAGGCGG  GCATGGAGGC  CCTGGCCCTT     720

TCCCGGAAGC  TTTCCCAGGT  GCACACTGAC  CTGCCCCTGG  AGGTGGACTT  CGGGAGGCGC     780

CGCACACCCA  ACCTGGAGGG  TCTGCGGGCT  TTTTTGGAGC  GGTTGGAGTT  TGGAAGCCTC     840

CTCCACGAGT  TCGGCCTCCT  GGAGGGGCCG  AAGGCGGCAG  AGGAGGCCCC  CTGGCCCCCT     900

CCGGAAGGGG  CTTTTTTGGG  CTTTTCCTTT  TCCCGTCCCG  AGCCCATGTG  GGCCGAGCTT     960

CTGGCCCTGG  CTGGGGCGTG  GGAGGGGCGC  CTCCATCGGG  CACAAGACCC  CCTTAGGGGC    1020

CTGAGGGACC  TTAAGGGGGT  GCGGGGAATC  CTGGCCAAGG  ACCTGGCGGT  TTTGGCCCTG    1080

CGGGAGGGCC  TGGACCTCTT  CCCAGAGGAC  GACCCCATGC  TCCTGGCCTA  CCTTCTGGAC    1140

CCCTCCAACA  CCACCCCTGA  GGGGTGGCC   CGGCGTTACG  GGGGGAGTG   GACGGAGGAT    1200

GCGGGGGAGA  GGGCCCTCCT  GGCCGAGCGC  CTCTTCCAGA  CCCTAAAGGA  GCGCCTTAAG    1260

GGAGAAGAAC  GCCTGCTTTG  GCTTTACGAG  GAGGTGGAGA  AGCCGCTTTC  CCGGGTGTTG    1320

GCCCGGATGG  AGGCCACGGG  GGTCCGGCTG  GACGTGGCCT  ACCTCCAGGC  CCTCTCCCTG    1380

GAGGTGGAGG  CGGAGGTGCG  CCAGCTGGAG  GAGGAGGTCT  TCCGCCTGGC  CGGCCACCCC    1440

TTCAACCTCA  ACTCCCGCGA  CCAGCTGGAG  CGGGTGCTCT  TTGACGAGCT  GGGCCTGCCT    1500

GCCATCGGCA  AGACGGAGAA  GACGGGGAAA  CGCTCCACCA  GCGCTGCCGT  GCTGGAGGCC    1560

CTGCGAGAGG  CCCACCCCAT  CGTGGACCGC  ATCCTGCAGT  ACCGGGAGCT  CACCAAGCTC    1620

AAGAACACCT  ACATAGACCC  CCTGCCCGCC  CTGGTCCACC  CCAAGACCGG  CCGGCTCCAC    1680

ACCCGCTTCA  ACCAGACGGC  CACCGCCACG  GGCAGGCTTT  CCAGCTCCGA  CCCCAACCTG    1740

CAGAACATCC  CCGTGCGCAC  CCCTCTGGGC  CAGCGCATCC  GCCGAGCCTT  CGTGGCCGAG    1800

GAGGGCTGGG  TGCTGGTGGT  CTTGGACTAC  AGCCAGATTG  AGCTTCGGGT  CCTGGCCCAC    1860

CTCTCCGGGG  ACGAGAACCT  GATCCGGGTC  TTTCAGGAGG  GGAGGGACAT  CCACACCCAG    1920

ACCGCCAGCT  GGATGTTCGG  CGTTTCCCCC  GAAGGGGTAG  ACCCTCTGAT  GCGCCGGGCG    1980

GCCAAGACCA  TCAACTTCGG  GGTGCTCTAC  GGCATGTCCG  CCCACCGCCT  CTCCGGGGAG    2040

CTTTCCATCC  CCTACGAGGA  GGCGGTGGCC  TTCATTGAGC  GCTACTTCCA  GAGCTACCCC    2100

AAGGTGCGGG  CCTGGATTGA  GGGGACCCTC  GAGGAGGGCC  GCCGGCGGGG  GTATGTGGAG    2160

ACCCTCTTCG  GCCGCCGGCG  CTATGTGCCC  GACCTCAACG  CCCGGGTGAA  GAGCGTGCGC    2220

GAGGCGGCGG  AGCGCATGGC  CTTCAACATG  CCGGTCCAGG  GCACCGCCGC  CGACCTCATG    2280

AAGCTGGCCA  TGGTGCGGCT  TTTCCCCCGG  CTTCAGGAAC  TGGGGGCGAG  GATGCTTTTG    2340

CAGGTGCACG  ACGAGCTGGT  CCTCGAGGCC  CCCAAGGACC  GGGCGGAGAG  GGTAGCCGCT    2400

TTGGCCAAGG  AGGTCATGGA  GGGGGTCTGG  CCCCTGCAGG  TGCCCCTGGA  GGTGGAGGTG    2460

GGCCTGGGGG  AGGACTGGCT  CTCCGCCAAG  GAGTAG                                2496
```

( 2 ) INFORMATION FOR SEQ ID NO:3:

( i ) SEQUENCE CHARACTERISTICS:
        ( A ) LENGTH: 2504 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
ATGGAGGCGA  TGCTTCCGCT  CTTTGAACCC  AAAGGCCGGG  TCCTCCTGGT  GGACGGCCAC      60

CACCTGGCCT  ACCGCACCTT  CTTCGCCCTG  AAGGGCCTCA  CCACGAGCCG  GGGCGAACCG     120
```

```
GTGCAGGCGG TCTACGGCTT CGCCAAGAGC CTCCTCAAGG CCCTGAAGGA GGACGGGTAC       180
AAGGCCGTCT TCGTGGTCTT TGACGCCAAG GCCCCTCCT  TCCGCCACGA GGCCTACGAG       240
GCCTACAAGG CGGGGAGGGC CCCGACCCCC GAGGACTTCC CCCGGCAGCT CGCCCTCATC       300
AAGGAGCTGG TGGACCTCCT GGGGTTTACC CGCCTCGAGG TCCCCGGCTA CGAGGCGGAC       360
GACGTTCTCG CCACCCTGGC CAAGAAGGCG GAAAAGGAGG GTACGAGGT  GCGCATCCTC       420
ACCGCCGACC GCGACCTCTA CCAACTCGTC TCCGACGCG  TCGCCGTCCT CCACCCCGAG       480
GGCCACCTCA TCACCCCGGA GTGGCTTTGG GAGAAGTACG GCCTCAGGCC GGAGCAGTGG       540
GTGGACTTCC GCGCCCTCGT GGGGGACCCC TCCGACAACC TCCCCGGGGT CAAGGGCATC       600
GGGGAGAAGA CCGCCCTCAA GCTCCTCAAG GAGTGGGGAA GCCTGGAAAA CCTCCTCAAG       660
AACCTGGACC GGGTAAAGCC AGAAACGTC  CGGGAGAAGA TCAAGGCCCA CCTGGAAGAC       720
CTCAGGCTCT CCTTGGAGCT CTCCCGGGTG CGCACCGACC TCCCCCTGGA GGTGGACCTC       780
GCCCAGGGGC GGGAGCCCGA CCGGGAGGGG CTTAGGGCCT TCCTGGAGAG GCTGGAGTTC       840
GGCAGCCTCC TCCACGAGTT CGGCCTCCTG GAGGCCCCCG CCCCCCTGGA GGAGGCCCC       900
TGGCCCCCGC CGGAAGGGGC CTTCGTGGGC TTCGTCCTCT CCCGCCCCGA GCCCATGTGG       960
GCGGAGCTTA AGCCCTGGC  CGCCTGCAGG GACGGCCGGG TGCACCGGGC AGCAGACCCC      1020
TTGGCGGGGC TAAAGGACCT CAAGGAGGTC CGGGGCCTCC TCGCCAAGGA CCTCGCCGTC      1080
TTGGCCTCGA GGGAGGGGCT AGACCTCGTG CCCGGGACG  ACCCCATGCT CCTCGCCTAC      1140
CTCCTGGACC CCTCCAACAC CACCCCCGAG GGGGTGGCGC GGCGCTACGG GGGGGAGTGG      1200
ACGGAGGACG CCGCCCACCG GGCCCTCCTC TCGGAGAGGC TCCATCGGAA CCTCCTTAAG      1260
CGCCTCGAGG GGGAGGAGAA GCTCCTTTGG CTCTACCACG AGGTGGAAAA GCCCCTCTCC      1320
CGGGTCCTGG CCCACATGGA GGCCACCGGG GTACGGCTGG ACGTGGCCTA CCTTCAGGCC      1380
CTTTCCCTGG AGCTTGCGGA GGAGATCCGC CGCCTCGAGG AGGAGGTCTT CCGCTTGGCG      1440
GGCCACCCCT TCAACCTCAA CTCCCGGGAC CAGCTGGAAA GGGTGCTCTT TGACGAGCTT      1500
AGGCTTCCCG CCTTGGGGAA GACGCAAAAG ACAGGCAAGC GCTCCACCAG CGCCGCGGTG      1560
CTGGAGGCCC TACGGGAGGC CCACCCCATC GTGGAGAAGA TCCTCCAGCA CCGGGAGCTC      1620
ACCAAGCTCA AGAACACCTA CGTGGACCCC CTCCCAAGCC TCGTCCACCC GAGGACGGGC      1680
CGCCTCCACA CCCGCTTCAA CCAGACGGCC ACGGCCACGG GAGGCTTAG  TAGCTCCGAC      1740
CCCAACCTGC AGAACATCCC CGTCCGCACC CCCTTGGGCC AGAGGATCCG CCGGGCCTTC      1800
GTGGCCGAGG CGGGTTGGGC GTTGGTGGCC CTGGACTATA GCCAGATAGA GCTCCGCGTC      1860
CTCGCCCACC TCTCCGGGGA CGAAAACCTG ATCAGGGTCT TCCAGGAGGG GAAGGACATC      1920
CACACCCAGA CCGCAAGCTG GATGTTCGGC GTCCCCCGG  AGGCCGTGGA CCCCCTGATG      1980
CGCCGGGCGG CCAAGACGGT GAACTTCGGC GTCCTCTACG GCATGTCCGC CCATAGGCTC      2040
TCCCAGGAGC TTGCCATCCC CTACGAGGAG GCGGTGGCCT TTATAGAGGC TACTTCCAAA      2100
GCTTCCCCAA GGTGCGGGCC TGGATAGAAA AGACCCTGGA GGAGGGGAGG AAGCGGGGCT      2160
ACGTGGAAAC CCTCTTCGGA AGAAGGCGCT ACGTGCCCGA CCTCAACGCC CGGGTGAAGA      2220
GCGTCAGGGA GGCCGCGGAG CGCATGGCCT TCAACATGCC CGTCCAGGGC ACCGCCGCCG      2280
ACCTCATGAA GCTCGCCATG GTGAAGCTCT TCCCCCGCCT CCGGGAGATG GGGGCCCGCA      2340
TGCTCCTCCA GGTCCACGAC GAGCTCCTCC TGGAGGCCCC CCAAGCGCGG GCCGAGGAGG      2400
TGGCGGCTTT GGCCAAGGAG GCCATGGAGA AGGCCTATCC CCTCGCCGTG CCCCTGGAGG      2460
TGGAGGTGGG GATGGGGGAG GACTGGCTTT CCGCCAAGGG TTAG                       2504
```

( 2 ) INFORMATION FOR SEQ ID NO:4:

( i ) SEQUENCE CHARACTERISTICS:
        ( A ) LENGTH: 832 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met Arg Gly Met Leu Pro Leu Phe Glu Pro Lys Gly Arg Val Leu Leu
 1               5                  10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
```

```
                    355                       360                       365
Pro  Gly  Asp  Asp  Pro  Met  Leu  Leu  Ala  Tyr  Leu  Leu  Asp  Pro  Ser  Asn
     370                 375                      380
Thr  Thr  Pro  Glu  Gly  Val  Ala  Arg  Arg  Tyr  Gly  Glu  Trp  Thr  Glu
385                      390                      395                      400
Glu  Ala  Gly  Glu  Arg  Ala  Ala  Leu  Ser  Glu  Arg  Leu  Phe  Ala  Asn  Leu
                    405                      410                           415
Trp  Gly  Arg  Leu  Glu  Gly  Glu  Glu  Arg  Leu  Leu  Trp  Leu  Tyr  Arg  Glu
               420                      425                      430
Val  Glu  Arg  Pro  Leu  Ser  Ala  Val  Leu  Ala  His  Met  Glu  Ala  Thr  Gly
          435                      440                      445
Val  Arg  Leu  Asp  Val  Ala  Tyr  Leu  Arg  Ala  Leu  Ser  Leu  Glu  Val  Ala
     450                      455                      460
Glu  Glu  Ile  Ala  Arg  Leu  Glu  Ala  Glu  Val  Phe  Arg  Leu  Ala  Gly  His
465                      470                      475                      480
Pro  Phe  Asn  Leu  Asn  Ser  Arg  Asp  Gln  Leu  Glu  Arg  Val  Leu  Phe  Asp
                    485                      490                      495
Glu  Leu  Gly  Leu  Pro  Ala  Ile  Gly  Lys  Thr  Glu  Lys  Thr  Gly  Lys  Arg
               500                      505                      510
Ser  Thr  Ser  Ala  Ala  Val  Leu  Glu  Ala  Leu  Arg  Glu  Ala  His  Pro  Ile
          515                      520                      525
Val  Glu  Lys  Ile  Leu  Gln  Tyr  Arg  Glu  Leu  Thr  Lys  Leu  Lys  Ser  Thr
     530                      535                      540
Tyr  Ile  Asp  Pro  Leu  Pro  Asp  Leu  Ile  His  Pro  Arg  Thr  Gly  Arg  Leu
545                      550                      555                      560
His  Thr  Arg  Phe  Asn  Gln  Thr  Ala  Thr  Thr  Gly  Arg  Leu  Ser  Ser
                    565                      570                      575
Ser  Asp  Pro  Asn  Leu  Gln  Asn  Ile  Pro  Val  Arg  Thr  Pro  Leu  Gly  Gln
               580                      585                      590
Arg  Ile  Arg  Arg  Ala  Phe  Ile  Ala  Glu  Glu  Gly  Trp  Leu  Leu  Val  Ala
          595                      600                      605
Leu  Asp  Tyr  Ser  Gln  Ile  Glu  Leu  Arg  Val  Leu  Ala  His  Leu  Ser  Gly
     610                      615                      620
Asp  Glu  Asn  Leu  Ile  Arg  Val  Phe  Gln  Glu  Gly  Arg  Asp  Ile  His  Thr
625                      630                      635                      640
Glu  Thr  Ala  Ser  Trp  Met  Phe  Gly  Val  Pro  Arg  Glu  Ala  Val  Asp  Pro
                    645                      650                      655
Leu  Met  Arg  Arg  Ala  Ala  Lys  Thr  Ile  Asn  Phe  Gly  Val  Leu  Tyr  Gly
               660                      665                      670
Met  Ser  Ala  His  Arg  Leu  Ser  Gln  Glu  Leu  Ala  Ile  Pro  Tyr  Glu  Glu
          675                      680                      685
Ala  Gln  Ala  Phe  Ile  Glu  Arg  Tyr  Phe  Gln  Ser  Phe  Pro  Lys  Val  Arg
     690                      695                      700
Ala  Trp  Ile  Glu  Lys  Thr  Leu  Glu  Glu  Gly  Arg  Arg  Arg  Gly  Tyr  Val
705                      710                      715                      720
Glu  Thr  Leu  Phe  Gly  Arg  Arg  Arg  Tyr  Val  Pro  Asp  Leu  Glu  Ala  Arg
                    725                      730                      735
Val  Lys  Ser  Val  Arg  Glu  Ala  Ala  Glu  Arg  Met  Ala  Phe  Asn  Met  Pro
               740                      745                      750
Val  Gln  Gly  Thr  Ala  Ala  Asp  Leu  Met  Lys  Leu  Ala  Met  Val  Lys  Leu
          755                      760                      765
Phe  Pro  Arg  Leu  Glu  Glu  Met  Gly  Ala  Arg  Met  Leu  Leu  Gln  Val  His
     770                      775                      780
```

| | | | | | | | | | | | | | | | |
|---|---|---|---|---|---|---|---|---|---|---|---|---|---|---|---|
| Asp | Glu | Leu | Val | Leu | Glu | Ala | Pro | Lys | Glu | Arg | Ala | Glu | Ala | Val | Ala |
| 785 | | | | 790 | | | | | 795 | | | | | | 800 |
| Arg | Leu | Ala | Lys | Glu | Val | Met | Glu | Gly | Val | Tyr | Pro | Leu | Ala | Val | Pro |
| | | | | 805 | | | | | 810 | | | | | 815 | |
| Leu | Glu | Val | Glu | Val | Gly | Ile | Gly | Glu | Asp | Trp | Leu | Ser | Ala | Lys | Glu |
| | | | 820 | | | | | 825 | | | | | 830 | | |

( 2 ) INFORMATION FOR SEQ ID NO:5:

( i ) SEQUENCE CHARACTERISTICS:
        ( A ) LENGTH: 831 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

| | | | | | | | | | | | | | | | |
|---|---|---|---|---|---|---|---|---|---|---|---|---|---|---|---|
| Met | Ala | Met | Leu | Pro | Leu | Phe | Glu | Pro | Lys | Gly | Arg | Val | Leu | Leu | Val |
| 1 | | | | 5 | | | | | 10 | | | | | 15 | |
| Asp | Gly | His | His | Leu | Ala | Tyr | Arg | Thr | Phe | Phe | Ala | Leu | Lys | Gly | Leu |
| | | | 20 | | | | 25 | | | | | 30 | | | |
| Thr | Thr | Ser | Arg | Gly | Glu | Pro | Val | Gln | Ala | Val | Tyr | Gly | Phe | Ala | Lys |
| | | | 35 | | | | 40 | | | | | 45 | | | |
| Ser | Leu | Leu | Lys | Ala | Leu | Lys | Glu | Asp | Gly | Asp | Val | Val | Val | Val | Val |
| | | 50 | | | | 55 | | | | | 60 | | | | |
| Phe | Asp | Ala | Lys | Ala | Pro | Ser | Phe | Arg | His | Glu | Ala | Tyr | Glu | Ala | Tyr |
| 65 | | | | | 70 | | | | 75 | | | | | | 80 |
| Lys | Ala | Gly | Arg | Ala | Pro | Thr | Pro | Glu | Asp | Phe | Pro | Arg | Gln | Leu | Ala |
| | | | | 85 | | | | | 90 | | | | | 95 | |
| Leu | Ile | Lys | Glu | Leu | Val | Asp | Leu | Leu | Gly | Leu | Val | Arg | Leu | Glu | Val |
| | | | 100 | | | | | 105 | | | | | 110 | | |
| Pro | Gly | Phe | Glu | Ala | Asp | Asp | Val | Leu | Ala | Thr | Leu | Ala | Lys | Arg | Ala |
| | | | 115 | | | | 120 | | | | | 125 | | | |
| Glu | Lys | Glu | Gly | Tyr | Glu | Val | Arg | Ile | Leu | Thr | Ala | Asp | Arg | Asp | Leu |
| | 130 | | | | | 135 | | | | | 140 | | | | |
| Tyr | Gln | Leu | Leu | Ser | Glu | Arg | Ile | Ala | Ile | Leu | His | Pro | Glu | Gly | Tyr |
| 145 | | | | | 150 | | | | | 155 | | | | | 160 |
| Leu | Ile | Thr | Pro | Ala | Trp | Leu | Tyr | Glu | Lys | Tyr | Gly | Leu | Arg | Pro | Glu |
| | | | | 165 | | | | | 170 | | | | | 175 | |
| Gln | Trp | Val | Asp | Tyr | Arg | Ala | Leu | Ala | Gly | Asp | Pro | Ser | Asp | Asn | Ile |
| | | | 180 | | | | | 185 | | | | | 190 | | |
| Pro | Gly | Val | Lys | Gly | Ile | Gly | Glu | Lys | Thr | Ala | Gln | Arg | Leu | Ile | Arg |
| | | | 195 | | | | | 200 | | | | | 205 | | |
| Glu | Trp | Gly | Ser | Leu | Glu | Asn | Leu | Phe | Gln | His | Leu | Asp | Gln | Val | Lys |
| | 210 | | | | | 215 | | | | | 220 | | | | |
| Pro | Ser | Leu | Arg | Glu | Lys | Leu | Gln | Ala | Gly | Met | Glu | Ala | Leu | Ala | Leu |
| 225 | | | | | 230 | | | | | 235 | | | | | 240 |
| Ser | Arg | Lys | Leu | Ser | Gln | Val | His | Thr | Asp | Leu | Pro | Leu | Glu | Val | Asp |
| | | | | 245 | | | | | 250 | | | | | 255 | |
| Phe | Gly | Arg | Arg | Arg | Thr | Pro | Asn | Leu | Glu | Gly | Leu | Arg | Ala | Phe | Leu |
| | | | 260 | | | | | 265 | | | | | 270 | | |
| Glu | Arg | Leu | Glu | Phe | Gly | Ser | Leu | Leu | His | Glu | Phe | Gly | Leu | Leu | Glu |
| | | 275 | | | | | 280 | | | | | 285 | | | |
| Gly | Pro | Lys | Ala | Ala | Glu | Glu | Ala | Pro | Trp | Pro | Pro | Pro | Glu | Gly | Ala |
| | 290 | | | | | 295 | | | | | 300 | | | | |
| Phe | Leu | Gly | Phe | Ser | Phe | Ser | Arg | Pro | Glu | Pro | Met | Trp | Ala | Glu | Leu |

|     |     |     |     |     |     |     |     |     |     |     |     |     |     |     |     |
|-----|-----|-----|-----|-----|-----|-----|-----|-----|-----|-----|-----|-----|-----|-----|-----|
| 305 |     |     |     | 310 |     |     |     | 315 |     |     |     | 320 |     |     |     |
| Leu | Ala | Leu | Ala | Gly | Ala | Trp | Glu | Gly | Arg | Leu | His | Arg | Ala | Gln | Asp |
|     |     |     | 325 |     |     |     |     | 330 |     |     |     | 335 |     |     |     |
| Pro | Leu | Arg | Gly | Leu | Arg | Asp | Leu | Lys | Gly | Val | Arg | Gly | Ile | Leu | Ala |
|     |     |     | 340 |     |     |     |     | 345 |     |     |     | 350 |     |     |     |
| Lys | Asp | Leu | Ala | Val | Leu | Ala | Leu | Arg | Glu | Gly | Leu | Asp | Leu | Phe | Pro |
|     |     |     | 355 |     |     |     |     | 360 |     |     |     | 365 |     |     |     |
| Glu | Asp | Asp | Pro | Met | Leu | Leu | Ala | Tyr | Leu | Leu | Asp | Pro | Ser | Asn | Thr |
|     |     |     | 370 |     |     |     |     | 375 |     |     |     | 380 |     |     |     |
| Thr | Pro | Glu | Gly | Val | Ala | Arg | Arg | Tyr | Gly | Gly | Glu | Trp | Thr | Glu | Asp |
| 385 |     |     |     |     | 390 |     |     |     |     | 395 |     |     |     |     | 400 |
| Ala | Gly | Glu | Arg | Ala | Leu | Leu | Ala | Glu | Arg | Leu | Phe | Gln | Thr | Leu | Lys |
|     |     |     |     | 405 |     |     |     |     | 410 |     |     |     |     | 415 |     |
| Glu | Arg | Leu | Lys | Gly | Glu | Glu | Arg | Leu | Leu | Trp | Leu | Tyr | Glu | Glu | Val |
|     |     |     | 420 |     |     |     |     | 425 |     |     |     | 430 |     |     |     |
| Glu | Lys | Pro | Leu | Ser | Arg | Val | Leu | Ala | Arg | Met | Glu | Ala | Thr | Gly | Val |
|     |     |     | 435 |     |     |     |     | 440 |     |     |     | 445 |     |     |     |
| Arg | Leu | Asp | Val | Ala | Tyr | Leu | Gln | Ala | Leu | Ser | Leu | Glu | Val | Glu | Ala |
|     |     |     | 450 |     |     |     |     | 455 |     |     |     | 460 |     |     |     |
| Glu | Val | Arg | Gln | Leu | Glu | Glu | Val | Phe | Arg | Leu | Ala | Gly | His | Pro |     |
| 465 |     |     |     |     | 470 |     |     |     |     | 475 |     |     |     |     | 480 |
| Phe | Asn | Leu | Asn | Ser | Arg | Asp | Gln | Leu | Glu | Arg | Val | Leu | Phe | Asp | Glu |
|     |     |     |     | 485 |     |     |     |     | 490 |     |     |     |     | 495 |     |
| Leu | Gly | Leu | Pro | Ala | Ile | Gly | Lys | Thr | Glu | Lys | Thr | Gly | Lys | Arg | Ser |
|     |     |     | 500 |     |     |     |     | 505 |     |     |     | 510 |     |     |     |
| Thr | Ser | Ala | Ala | Val | Leu | Glu | Ala | Leu | Arg | Glu | Ala | His | Pro | Ile | Val |
|     |     |     | 515 |     |     |     |     | 520 |     |     |     | 525 |     |     |     |
| Asp | Arg | Ile | Leu | Gln | Tyr | Arg | Glu | Leu | Thr | Lys | Leu | Lys | Asn | Thr | Tyr |
|     |     |     | 530 |     |     |     |     | 535 |     |     |     | 540 |     |     |     |
| Ile | Asp | Pro | Leu | Pro | Ala | Leu | Val | His | Pro | Lys | Thr | Gly | Arg | Leu | His |
| 545 |     |     |     |     | 550 |     |     |     |     | 555 |     |     |     |     | 560 |
| Thr | Arg | Phe | Asn | Gln | Thr | Ala | Thr | Ala | Thr | Gly | Arg | Leu | Ser | Ser | Ser |
|     |     |     |     | 565 |     |     |     |     | 570 |     |     |     |     | 575 |     |
| Asp | Pro | Asn | Leu | Gln | Asn | Ile | Pro | Val | Arg | Thr | Pro | Leu | Gly | Gln | Arg |
|     |     |     | 580 |     |     |     |     | 585 |     |     |     | 590 |     |     |     |
| Ile | Arg | Arg | Ala | Phe | Val | Ala | Glu | Glu | Gly | Trp | Val | Leu | Val | Val | Leu |
|     |     |     | 595 |     |     |     |     | 600 |     |     |     | 605 |     |     |     |
| Asp | Tyr | Ser | Gln | Ile | Glu | Leu | Arg | Val | Leu | Ala | His | Leu | Ser | Gly | Asp |
|     |     |     | 610 |     |     |     |     | 615 |     |     |     | 620 |     |     |     |
| Glu | Asn | Leu | Ile | Arg | Val | Phe | Gln | Glu | Gly | Arg | Asp | Ile | His | Thr | Gln |
| 625 |     |     |     |     | 630 |     |     |     |     | 635 |     |     |     |     | 640 |
| Thr | Ala | Ser | Trp | Met | Phe | Gly | Val | Ser | Pro | Glu | Gly | Val | Asp | Pro | Leu |
|     |     |     |     | 645 |     |     |     |     | 650 |     |     |     |     | 655 |     |
| Met | Arg | Arg | Ala | Ala | Lys | Thr | Ile | Asn | Phe | Gly | Val | Leu | Tyr | Gly | Met |
|     |     |     | 660 |     |     |     |     | 665 |     |     |     | 670 |     |     |     |
| Ser | Ala | His | Arg | Leu | Ser | Gly | Glu | Leu | Ser | Ile | Pro | Tyr | Glu | Glu | Ala |
|     |     |     | 675 |     |     |     |     | 680 |     |     |     | 685 |     |     |     |
| Val | Ala | Phe | Ile | Glu | Arg | Tyr | Phe | Gln | Ser | Tyr | Pro | Lys | Val | Arg | Ala |
|     |     |     | 690 |     |     |     |     | 695 |     |     |     | 700 |     |     |     |
| Trp | Ile | Glu | Gly | Thr | Leu | Glu | Glu | Gly | Arg | Arg | Arg | Gly | Tyr | Val | Glu |
| 705 |     |     |     |     | 710 |     |     |     |     | 715 |     |     |     |     | 720 |
| Thr | Leu | Phe | Gly | Arg | Arg | Arg | Tyr | Val | Pro | Asp | Leu | Asn | Ala | Arg | Val |
|     |     |     |     | 725 |     |     |     |     | 730 |     |     |     |     | 735 |     |

```
Lys  Ser  Val  Arg  Glu  Ala  Ala  Glu  Arg  Met  Ala  Phe  Asn  Met  Pro  Val
               740                 745                          750

Gln  Gly  Thr  Ala  Ala  Asp  Leu  Met  Lys  Leu  Ala  Met  Val  Arg  Leu  Phe
          755                      760                 765

Pro  Arg  Leu  Gln  Glu  Leu  Gly  Ala  Arg  Met  Leu  Leu  Gln  Val  His  Asp
     770                      775                      780

Glu  Leu  Val  Leu  Glu  Ala  Pro  Lys  Asp  Arg  Ala  Glu  Arg  Val  Ala  Ala
785                      790                 795                           800

Leu  Ala  Lys  Glu  Val  Met  Glu  Gly  Val  Trp  Pro  Leu  Gln  Val  Pro  Leu
               805                      810                      815

Glu  Val  Glu  Val  Gly  Leu  Gly  Glu  Asp  Trp  Leu  Ser  Ala  Lys  Glu
               820                 825                          830
```

( 2 ) INFORMATION FOR SEQ ID NO:6:

( i ) SEQUENCE CHARACTERISTICS:
    ( A ) LENGTH: 834 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:6:

```
Met  Glu  Ala  Met  Leu  Pro  Leu  Phe  Glu  Pro  Lys  Gly  Arg  Val  Leu  Leu
1                   5                   10                      15

Val  Asp  Gly  His  His  Leu  Ala  Tyr  Arg  Thr  Phe  Phe  Ala  Leu  Lys  Gly
               20                  25                      30

Leu  Thr  Thr  Ser  Arg  Gly  Glu  Pro  Val  Gln  Ala  Val  Tyr  Gly  Phe  Ala
          35                      40                      45

Lys  Ser  Leu  Leu  Lys  Ala  Leu  Lys  Glu  Asp  Gly  Tyr  Lys  Ala  Val  Phe
     50                       55                      60

Val  Val  Phe  Asp  Ala  Lys  Ala  Pro  Ser  Phe  Arg  His  Glu  Ala  Tyr  Glu
65                       70                      75                           80

Ala  Tyr  Lys  Ala  Gly  Arg  Ala  Pro  Thr  Pro  Glu  Asp  Phe  Pro  Arg  Gln
               85                       90                           95

Leu  Ala  Leu  Ile  Lys  Glu  Leu  Val  Asp  Leu  Leu  Gly  Phe  Thr  Arg  Leu
               100                      105                     110

Glu  Val  Pro  Gly  Tyr  Glu  Ala  Asp  Asp  Val  Leu  Ala  Thr  Leu  Ala  Lys
          115                      120                     125

Lys  Ala  Glu  Lys  Glu  Gly  Tyr  Glu  Val  Arg  Ile  Leu  Thr  Ala  Asp  Arg
     130                      135                     140

Asp  Leu  Tyr  Gln  Leu  Val  Ser  Asp  Arg  Val  Ala  Val  Leu  His  Pro  Glu
145                      150                      155                          160

Gly  His  Leu  Ile  Thr  Pro  Glu  Trp  Leu  Trp  Glu  Lys  Tyr  Gly  Leu  Arg
               165                      170                     175

Pro  Glu  Gln  Trp  Val  Asp  Phe  Arg  Ala  Leu  Val  Gly  Asp  Pro  Ser  Asp
          180                      185                     190

Asn  Leu  Pro  Gly  Val  Lys  Gly  Ile  Gly  Glu  Lys  Thr  Ala  Leu  Lys  Leu
          195                      200                     205

Leu  Lys  Glu  Trp  Gly  Ser  Leu  Glu  Asn  Leu  Leu  Lys  Asn  Leu  Asp  Arg
     210                      215                     220

Val  Lys  Pro  Glu  Asn  Val  Arg  Glu  Lys  Ile  Lys  Ala  His  Leu  Glu  Asp
225                      230                      235                          240

Leu  Arg  Leu  Ser  Leu  Glu  Leu  Ser  Arg  Val  Arg  Thr  Asp  Leu  Pro  Leu
               245                      250                     255

Glu  Val  Asp  Leu  Ala  Gln  Gly  Arg  Glu  Pro  Asp  Arg  Glu  Gly  Leu  Arg
```

-continued

|     |     |     |     |     | 260 |     |     |     |     | 265 |     |     |     |     | 270 |     |     |
|-----|-----|-----|-----|-----|-----|-----|-----|-----|-----|-----|-----|-----|-----|-----|-----|-----|-----|
| Ala | Phe | Leu | Glu | Arg | Leu | Glu | Phe | Gly | Ser | Leu | Leu | His | Glu | Phe | Gly |
|     |     | 275 |     |     |     |     | 280 |     |     |     |     | 285 |     |     |     |
| Leu | Leu | Glu | Ala | Pro | Ala | Pro | Leu | Glu | Glu | Ala | Pro | Trp | Pro | Pro | Pro |
|     | 290 |     |     |     |     | 295 |     |     |     |     | 300 |     |     |     |     |
| Glu | Gly | Ala | Phe | Val | Gly | Phe | Val | Leu | Ser | Arg | Pro | Glu | Pro | Met | Trp |
| 305 |     |     |     |     | 310 |     |     |     |     | 315 |     |     |     |     | 320 |
| Ala | Glu | Leu | Lys | Ala | Leu | Ala | Ala | Cys | Arg | Asp | Gly | Arg | Val | His | Arg |
|     |     |     |     | 325 |     |     |     |     | 330 |     |     |     |     | 335 |     |
| Ala | Ala | Asp | Pro | Leu | Ala | Gly | Leu | Lys | Asp | Leu | Lys | Glu | Val | Arg | Gly |
|     |     |     | 340 |     |     |     |     | 345 |     |     |     |     | 350 |     |     |
| Leu | Leu | Ala | Lys | Asp | Leu | Ala | Val | Leu | Ala | Ser | Arg | Glu | Gly | Leu | Asp |
|     |     | 355 |     |     |     |     | 360 |     |     |     |     | 365 |     |     |     |
| Leu | Val | Pro | Gly | Asp | Asp | Pro | Met | Leu | Leu | Ala | Tyr | Leu | Leu | Asp | Pro |
|     | 370 |     |     |     |     | 375 |     |     |     |     | 380 |     |     |     |     |
| Ser | Asn | Thr | Thr | Pro | Glu | Gly | Val | Ala | Arg | Arg | Tyr | Gly | Gly | Glu | Trp |
| 385 |     |     |     |     | 390 |     |     |     |     | 395 |     |     |     |     | 400 |
| Thr | Glu | Asp | Ala | Ala | His | Arg | Ala | Leu | Leu | Ser | Glu | Arg | Leu | His | Arg |
|     |     |     |     | 405 |     |     |     |     | 410 |     |     |     |     | 415 |     |
| Asn | Leu | Leu | Lys | Arg | Leu | Glu | Gly | Glu | Glu | Lys | Leu | Leu | Trp | Leu | Tyr |
|     |     |     | 420 |     |     |     |     | 425 |     |     |     |     | 430 |     |     |
| His | Glu | Val | Glu | Lys | Pro | Leu | Ser | Arg | Val | Leu | Ala | His | Met | Glu | Ala |
|     |     | 435 |     |     |     |     | 440 |     |     |     |     | 445 |     |     |     |
| Thr | Gly | Val | Arg | Leu | Asp | Val | Ala | Tyr | Leu | Gln | Ala | Leu | Ser | Leu | Glu |
|     | 450 |     |     |     |     | 455 |     |     |     |     | 460 |     |     |     |     |
| Leu | Ala | Glu | Glu | Ile | Arg | Arg | Leu | Glu | Glu | Glu | Val | Phe | Arg | Leu | Ala |
| 465 |     |     |     |     | 470 |     |     |     |     | 475 |     |     |     |     | 480 |
| Gly | His | Pro | Phe | Asn | Leu | Asn | Ser | Arg | Asp | Gln | Leu | Glu | Arg | Val | Leu |
|     |     |     |     | 485 |     |     |     |     | 490 |     |     |     |     | 495 |     |
| Phe | Asp | Glu | Leu | Arg | Leu | Pro | Ala | Leu | Gly | Lys | Thr | Gln | Lys | Thr | Gly |
|     |     |     | 500 |     |     |     |     | 505 |     |     |     |     | 510 |     |     |
| Lys | Arg | Ser | Thr | Ser | Ala | Ala | Val | Leu | Glu | Ala | Leu | Arg | Glu | Ala | His |
|     |     | 515 |     |     |     |     | 520 |     |     |     |     | 525 |     |     |     |
| Pro | Ile | Val | Glu | Lys | Ile | Leu | Gln | His | Arg | Glu | Leu | Thr | Lys | Leu | Lys |
|     | 530 |     |     |     |     | 535 |     |     |     |     | 540 |     |     |     |     |
| Asn | Thr | Tyr | Val | Asp | Pro | Leu | Pro | Ser | Leu | Val | His | Pro | Arg | Thr | Gly |
| 545 |     |     |     |     | 550 |     |     |     |     | 555 |     |     |     |     | 560 |
| Arg | Leu | His | Thr | Arg | Phe | Asn | Gln | Thr | Ala | Thr | Ala | Thr | Gly | Arg | Leu |
|     |     |     |     | 565 |     |     |     |     | 570 |     |     |     |     | 575 |     |
| Ser | Ser | Ser | Asp | Pro | Asn | Leu | Gln | Asn | Ile | Pro | Val | Arg | Thr | Pro | Leu |
|     |     |     | 580 |     |     |     |     | 585 |     |     |     |     | 590 |     |     |
| Gly | Gln | Arg | Ile | Arg | Arg | Ala | Phe | Val | Ala | Glu | Ala | Gly | Trp | Ala | Leu |
|     |     | 595 |     |     |     |     | 600 |     |     |     |     | 605 |     |     |     |
| Val | Ala | Leu | Asp | Tyr | Ser | Gln | Ile | Glu | Leu | Arg | Val | Leu | Ala | His | Leu |
|     | 610 |     |     |     |     | 615 |     |     |     |     | 620 |     |     |     |     |
| Ser | Gly | Asp | Glu | Asn | Leu | Ile | Arg | Val | Phe | Gln | Glu | Gly | Lys | Asp | Ile |
| 625 |     |     |     |     | 630 |     |     |     |     | 635 |     |     |     |     | 640 |
| His | Thr | Gln | Thr | Ala | Ser | Trp | Met | Phe | Gly | Val | Pro | Pro | Glu | Ala | Val |
|     |     |     |     | 645 |     |     |     |     | 650 |     |     |     |     | 655 |     |
| Asp | Pro | Leu | Met | Arg | Arg | Ala | Ala | Lys | Thr | Val | Asn | Phe | Gly | Val | Leu |
|     |     |     | 660 |     |     |     |     | 665 |     |     |     |     | 670 |     |     |
| Tyr | Gly | Met | Ser | Ala | His | Arg | Leu | Ser | Gln | Glu | Leu | Ala | Ile | Pro | Tyr |
|     |     | 675 |     |     |     |     | 680 |     |     |     |     | 685 |     |     |     |

| | | | | | | | | | | | | | | |
|---|---|---|---|---|---|---|---|---|---|---|---|---|---|---|
| Glu | Glu | Ala | Val | Ala | Phe | Ile | Glu | Arg | Tyr | Phe | Gln | Ser | Phe | Pro | Lys |
| | 690 | | | | | 695 | | | | | 700 | | | | |
| Val | Arg | Ala | Trp | Ile | Glu | Lys | Thr | Leu | Glu | Glu | Gly | Arg | Lys | Arg | Gly |
| 705 | | | | | 710 | | | | | 715 | | | | | 720 |
| Tyr | Val | Glu | Thr | Leu | Phe | Gly | Arg | Arg | Arg | Tyr | Val | Pro | Asp | Leu | Asn |
| | | | | 725 | | | | | 730 | | | | | 735 | |
| Ala | Arg | Val | Lys | Ser | Val | Arg | Glu | Ala | Ala | Glu | Arg | Met | Ala | Phe | Asn |
| | | | 740 | | | | | 745 | | | | | 750 | | |
| Met | Pro | Val | Gln | Gly | Thr | Ala | Ala | Asp | Leu | Met | Lys | Leu | Ala | Met | Val |
| | | 755 | | | | | 760 | | | | | 765 | | | |
| Lys | Leu | Phe | Pro | Arg | Leu | Arg | Glu | Met | Gly | Ala | Arg | Met | Leu | Leu | Gln |
| | 770 | | | | | 775 | | | | | 780 | | | | |
| Val | His | Asp | Glu | Leu | Leu | Leu | Glu | Ala | Pro | Gln | Ala | Arg | Ala | Glu | Glu |
| 785 | | | | | 790 | | | | | 795 | | | | | 800 |
| Val | Ala | Ala | Leu | Ala | Lys | Glu | Ala | Met | Glu | Lys | Ala | Tyr | Pro | Leu | Ala |
| | | | | 805 | | | | | 810 | | | | | 815 | |
| Val | Pro | Leu | Glu | Val | Glu | Val | Gly | Met | Gly | Glu | Asp | Trp | Leu | Ser | Ala |
| | | | 820 | | | | | 825 | | | | | 830 | | |
| Lys | Gly | | | | | | | | | | | | | | |

( 2 ) INFORMATION FOR SEQ ID NO:7:

( i ) SEQUENCE CHARACTERISTICS:
 ( A ) LENGTH: 2502 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:7:

```
ATGNNGGCGA TGCTTCCCCT CTTTGAGCCC AAAGGCCGGG TCCTCCTGGT GGACGGCCAC      60
CACCTGGCCT ACCGCACCTT CTTCGCCCTG AAGGGCCTCA CCACCAGCCG GGGCGAACCG     120
GTGCAGGCGG TCTACGGCTT CGCCAAGAGC CTCCTCAAGG CCCTGAAGGA GGACGGGGAC     180
NNGGCGGTGN TCGTGGTCTT TGACGCCAAG GCCCCTCCT TCCGCCACGA GGCCTACGAG      240
GCCTACAAGG CGGGCCGGGC CCCCACCCCG GAGGACTTTC CCGGCAGCT CGCCCTCATC      300
AAGGAGCTGG TGGACCTCCT GGGGCTTGCG CGCCTCGAGG TCCCCGGCTA CGAGGCGGAC     360
GACGTNCTGG CCACCCTGGC CAAGAAGGCG GAAAAGGAGG GTACGAGGT GCGCATCCTC      420
ACCGCCGACC GCGACCTCTA CCAGCTCCTT TCCGACCGCA TCGCCGTCCT CCACCCCGAG     480
GGGTACCTCA TCACCCCGGC GTGGCTTTGG GAGAAGTACG GCCTGAGGCC GGAGCAGTGG     540
GTGGACTACC GGGCCCTGGC GGGGGACCCC TCCGACAACC TCCCCGGGGT CAAGGGCATC     600
GGGGAGAAGA CCGCCCNGAA GCTCCTCNAG GAGTGGGGGA GCCTGGAAAA CCTCCTCAAG     660
AACCTGGACC GGGTGAAGCC CGCCNTCCGG GAGAAGATCC AGGCCCACAT GGANGACCTG     720
ANGCTCTCCT GGGAGCTNTC CCAGGTGCGC ACCGACCTGC CCCTGGAGGT GGACTTCGCC     780
AAGNGGCGGG AGCCCGACCG GGAGGGGCTT AGGGCCTTTC TGGAGAGGCT GGAGTTTGGC     840
AGCCTCCTCC ACGAGTTCGG CCTCCTGGAG GGCCCAAGG CCCTGGAGGA GGCCCCTGG      900
CCCCGCCGG AAGGGGCCTT CGTGGGCTTT GTCCTTTCCC GCCCCGAGCC CATGTGGGCC     960
GAGCTTCTGG CCCTGGCCGC CGCCAGGGAG GGCCGGGTCC ACCGGGCACC AGACCCCTTT    1020
ANGGGCCTNA GGGACCTNAA GGAGGTGCGG GGNCTCCTCG CCAAGGACCT GGCCGTTTTG    1080
GCCCTGAGGG AGGGCCTNGA CCTCNTGCCC GGGGACGACC CCATGCTCCT CGCCTACCTC    1140
CTGGACCCCT CCAACACCAC CCCCGAGGGG GTGGCCCGGC GCTACGGGGG GGAGTGGACG    1200
```

-continued

| | | | | | |
|---|---|---|---|---|---|
| GAGGANGCGG | GGGAGCGGGC | CCTCCTNTCC | GAGAGGCTCT | TCCNGAACCT | NNNGCAGCGC | 1260
| CTTGAGGGGG | AGGAGAGGCT | CCTTTGGCTT | TACCAGGAGG | TGGAGAAGCC | CCTTTCCCGG | 1320
| GTCCTGGCCC | ACATGGAGGC | CACGGGGGTN | CGGCTGGACG | TGGCCTACCT | CCAGGCCCTN | 1380
| TCCCTGGAGG | TGGCGGAGGA | GATCCGCCGC | CTCGAGGAGG | AGGTCTTCCG | CCTGGCCGGC | 1440
| CACCCCTTCA | ACCTCAACTC | CCGGGACCAG | CTGGAAAGGG | TGCTCTTTGA | CGAGCTNGGG | 1500
| CTTCCCGCCA | TCGGCAAGAC | GGAGAAGACN | GGCAAGCGCT | CCACCAGCGC | CGCCGTGCTG | 1560
| GAGGCCCTNC | GNGAGGCCCA | CCCCATCGTG | GAGAAGATCC | TGCAGTACCG | GGAGCTCACC | 1620
| AAGCTCAAGA | ACACCTACAT | NGACCCCCTG | CCNGCCTCG | TCCACCCCAG | GACGGGCCGC | 1680
| CTCCACACCC | GCTTCAACCA | GACGGCCACG | GCCACGGGCA | GGCTTAGTAG | CTCCGACCCC | 1740
| AACCTGCAGA | ACATCCCCGT | CCGCACCCCN | CTGGGCCAGA | GGATCCGCCG | GGCCTTCGTG | 1800
| GCCGAGGAGG | GNTGGGTGTT | GGTGGCCCTG | GACTATAGCC | AGATAGAGCT | CCGGGTCCTG | 1860
| GCCCACCTCT | CCGGGGACGA | GAACCTGATC | CGGGTCTTCC | AGGAGGGGAG | GGACATCCAC | 1920
| ACCCAGACCG | CCAGCTGGAT | GTTCGGCGTC | CCCCCGGAGG | CCGTGGACCC | CCTGATGCGC | 1980
| CGGGCGGCCA | AGACCATCAA | CTTCGGGGTC | CTCTACGGCA | TGTCCGCCCA | CCGCCTCTCC | 2040
| CAGGAGCTTG | CCATCCCCTA | CGAGGAGGCG | GTGGCCTTCA | TTGAGCGCTA | CTTCCAGAGC | 2100
| TTCCCCAAGG | TGCGGGCCTG | GATTGAGAAG | ACCCTGGAGG | AGGGCAGGAG | GCGGGGGTAC | 2160
| GTGGAGACCC | TCTTCGGCCG | CCGGCGCTAC | GTGCCCGACC | TCAACGCCCG | GGTGAAGAGC | 2220
| GTGCGGGAGG | CGGCGGAGCG | CATGGCCTTC | AACATGCCCG | TCCAGGGCAC | CGCCGCCGAC | 2280
| CTCATGAAGC | TGGCCATGGT | GAAGCTCTTC | CCCCGGCTNC | AGGAAATGGG | GGCCAGGATG | 2340
| CTCCTNCAGG | TCCACGACGA | GCTGGTCCTC | GAGGCCCCCA | AAGAGCGGGC | GGAGGNGGTG | 2400
| GCCGCTTTGG | CCAAGGAGGT | CATGGAGGGG | GTCTATCCCC | TGGCCGTGCC | CCTGGAGGTG | 2460
| GAGGTGGGGA | TGGGGAGGA | CTGGCTCTCC | GCCAAGGAGT | AG | | 2502

( 2 ) INFORMATION FOR SEQ ID NO:8:

( i ) SEQUENCE CHARACTERISTICS:
( A ) LENGTH: 833 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:8:

```
Met Xaa Ala Met Leu Pro Leu Phe Glu Pro Lys Gly Arg Val Leu Leu
  1               5                  10                  15

Val Asp Gly His His Leu Ala Tyr Arg Thr Phe Phe Ala Leu Lys Gly
              20                  25                  30

Leu Thr Thr Ser Arg Gly Glu Pro Val Gln Ala Val Tyr Gly Phe Ala
          35                  40                  45

Lys Ser Leu Leu Lys Ala Leu Lys Glu Asp Gly Asp Ala Val Xaa Val
      50                  55                  60

Val Phe Asp Ala Lys Ala Pro Ser Phe Arg His Glu Ala Tyr Glu Ala
 65                  70                  75                  80

Tyr Lys Ala Gly Arg Ala Pro Thr Pro Glu Asp Phe Pro Arg Gln Leu
                  85                  90                  95

Ala Leu Ile Lys Glu Leu Val Asp Leu Leu Gly Leu Xaa Arg Leu Glu
             100                 105                 110

Val Pro Gly Tyr Glu Ala Asp Asp Val Leu Ala Thr Leu Ala Lys Lys
         115                 120                 125
```

```
Ala Glu Lys Glu Gly Tyr Glu Val Arg Ile Leu Thr Ala Asp Arg Asp
    130             135                 140
Leu Tyr Gln Leu Leu Ser Asp Arg Ile Ala Val Leu His Pro Glu Gly
145             150                 155                 160
Tyr Leu Ile Thr Pro Ala Trp Leu Trp Lys Tyr Gly Leu Arg Pro
                165                 170                 175
Glu Gln Trp Val Asp Tyr Arg Ala Leu Xaa Gly Asp Pro Ser Asp Asn
            180                 185                 190
Leu Pro Gly Val Lys Gly Ile Gly Glu Lys Thr Ala Xaa Lys Leu Leu
            195                 200                 205
Xaa Glu Trp Gly Ser Leu Glu Asn Leu Leu Lys Asn Leu Asp Arg Val
    210                 215                 220
Lys Pro Xaa Xaa Arg Glu Lys Ile Xaa Ala His Met Glu Asp Leu Xaa
225                 230                 235                 240
Leu Ser Xaa Xaa Leu Ser Xaa Val Arg Thr Asp Leu Pro Leu Glu Val
                245             250                 255
Asp Phe Ala Xaa Arg Arg Glu Pro Asp Arg Glu Gly Leu Arg Ala Phe
            260                 265                 270
Leu Glu Arg Leu Glu Phe Gly Ser Leu Leu His Glu Phe Gly Leu Leu
        275                 280                 285
Glu Xaa Pro Lys Ala Leu Glu Glu Ala Pro Trp Pro Pro Pro Glu Gly
    290                 295                 300
Ala Phe Val Gly Phe Val Leu Ser Arg Pro Glu Pro Met Trp Ala Glu
305                 310                 315                 320
Leu Leu Ala Leu Ala Ala Ala Arg Xaa Gly Arg Val His Arg Ala Xaa
                325                 330                 335
Asp Pro Leu Xaa Gly Leu Arg Asp Leu Lys Glu Val Arg Gly Leu Leu
            340                 345                 350
Ala Lys Asp Leu Ala Val Leu Ala Leu Arg Glu Gly Leu Asp Leu Xaa
            355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Asp Ala Gly Glu Arg Ala Leu Leu Ser Glu Arg Leu Phe Xaa Asn Leu
                405                 410                 415
Xaa Xaa Arg Leu Glu Gly Glu Glu Arg Leu Leu Trp Leu Tyr Xaa Glu
            420                 425                 430
Val Glu Lys Pro Leu Ser Arg Val Leu Ala His Met Glu Ala Thr Gly
        435                 440                 445
Val Arg Leu Asp Val Ala Tyr Leu Gln Ala Leu Ser Leu Glu Val Ala
    450                 455                 460
Glu Glu Ile Arg Arg Leu Glu Glu Val Phe Arg Leu Ala Gly His
465                 470                 475                 480
Pro Phe Asn Leu Asn Ser Arg Asp Gln Leu Glu Arg Val Leu Phe Asp
            485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
        515                 520                 525
Val Glu Lys Ile Leu Gln Tyr Arg Glu Leu Thr Lys Leu Lys Asn Thr
    530                 535                 540
Tyr Ile Asp Pro Leu Pro Xaa Leu Val His Pro Arg Thr Gly Arg Leu
```

|     | 545 | | | | 550 | | | | 555 | | | | 560 |
|---|---|---|---|---|---|---|---|---|---|---|---|---|---|
| | His | Thr | Arg | Phe | Asn | Gln | Thr | Ala | Thr | Ala | Thr | Gly | Arg | Leu | Ser | Ser |
| | | | | | 565 | | | | 570 | | | | 575 |
| | Ser | Asp | Pro | Asn | Leu | Gln | Asn | Ile | Pro | Val | Arg | Thr | Pro | Leu | Gly | Gln |
| | | | | 580 | | | | 585 | | | | 590 |
| | Arg | Ile | Arg | Arg | Ala | Phe | Val | Ala | Glu | Glu | Gly | Trp | Xaa | Leu | Val | Ala |
| | | | 595 | | | | 600 | | | | 605 |
| | Leu | Asp | Tyr | Ser | Gln | Ile | Glu | Leu | Arg | Val | Leu | Ala | His | Leu | Ser | Gly |
| | | 610 | | | | 615 | | | | 620 |
| | Asp | Glu | Asn | Leu | Ile | Arg | Val | Phe | Gln | Glu | Gly | Arg | Asp | Ile | His | Thr |
| | 625 | | | | 630 | | | | 635 | | | | 640 |
| | Gln | Thr | Ala | Ser | Trp | Met | Phe | Gly | Val | Pro | Pro | Glu | Ala | Val | Asp | Pro |
| | | | | 645 | | | | 650 | | | | 655 |
| | Leu | Met | Arg | Arg | Ala | Ala | Lys | Thr | Ile | Asn | Phe | Gly | Val | Leu | Tyr | Gly |
| | | | | 660 | | | | 665 | | | | 670 |
| | Met | Ser | Ala | His | Arg | Leu | Ser | Gln | Glu | Leu | Ala | Ile | Pro | Tyr | Glu | Glu |
| | | | 675 | | | | 680 | | | | 685 |
| | Ala | Val | Ala | Phe | Ile | Glu | Arg | Tyr | Phe | Gln | Ser | Phe | Pro | Lys | Val | Arg |
| | | 690 | | | | 695 | | | | 700 |
| | Ala | Trp | Ile | Glu | Lys | Thr | Leu | Glu | Glu | Gly | Arg | Arg | Arg | Gly | Tyr | Val |
| | 705 | | | | 710 | | | | 715 | | | | 720 |
| | Glu | Thr | Leu | Phe | Gly | Arg | Arg | Arg | Tyr | Val | Pro | Asp | Leu | Asn | Ala | Arg |
| | | | | 725 | | | | 730 | | | | 735 |
| | Val | Lys | Ser | Val | Arg | Glu | Ala | Ala | Glu | Arg | Met | Ala | Phe | Asn | Met | Pro |
| | | | 740 | | | | 745 | | | | 750 |
| | Val | Gln | Gly | Thr | Ala | Ala | Asp | Leu | Met | Lys | Leu | Ala | Met | Val | Lys | Leu |
| | | | 755 | | | | 760 | | | | 765 |
| | Phe | Pro | Arg | Leu | Xaa | Glu | Met | Gly | Ala | Arg | Met | Leu | Leu | Gln | Val | His |
| | | 770 | | | | 775 | | | | 780 |
| | Asp | Glu | Leu | Val | Leu | Glu | Ala | Pro | Lys | Xaa | Arg | Ala | Glu | Xaa | Val | Ala |
| | 785 | | | | 790 | | | | 795 | | | | 800 |
| | Ala | Leu | Ala | Lys | Glu | Val | Met | Glu | Gly | Val | Tyr | Pro | Leu | Ala | Val | Pro |
| | | | | 805 | | | | 810 | | | | 815 |
| | Leu | Glu | Val | Glu | Val | Gly | Xaa | Gly | Glu | Asp | Trp | Leu | Ser | Ala | Lys | Glu |
| | | | 820 | | | | 825 | | | | 830 |
| | Xaa |

( 2 ) INFORMATION FOR SEQ ID NO:9:

( i ) SEQUENCE CHARACTERISTICS:
        ( A ) LENGTH: 1647 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

```
ATGAATTCGG  GGATGCTGCC  CCTCTTTGAG  CCCAAGGGCC  GGGTCCTCCT  GGTGGACGGC     60

CACCACCTGG  CCTACCGCAC  CTTCCACGCC  CTGAAGGGCC  TCACCACCAG  CCGGGGGGAG    120

CCGGTGCAGG  CGGTCTACGG  CTTCGCCAAG  AGCCTCCTCA  AGGCCCTCAA  GGAGGACGGG    180

GACGCGGTGA  TCGTGGTCTT  TGACGCCAAG  GCCCCCTCCT  TCCGCCACGA  GGCCTACGGG    240

GGGTACAAGG  CGGGCCGGGC  CCCCACGCCG  GAGGACTTTC  CCCGGCAACT  CGCCCTCATC    300

AAGGAGCTGG  TGGACCTCCT  GGGGCTGGCG  CGCCTCGAGG  TCCCGGGCTA  CGAGGCGGAC    360
```

| | | | | | |
|---|---|---|---|---|---|
| GACGTCCTGG | CCAGCCTGGC | CAAGAAGGCG | GAAAAGGAGG | GCTACGAGGT | CCGCATCCTC | 420
| ACCGCCGACA | AAGACCTTTA | CCAGCTCCTT | TCCGACCGCA | TCCACGTCCT | CCACCCCGAG | 480
| GGGTACCTCA | TCACCCCGGC | CTGGCTTTGG | GAAAAGTACG | GCCTGAGGCC | CGACCAGTGG | 540
| GCCGACTACC | GGGCCCTGAC | CGGGGACGAG | TCCGACAACC | TTCCCGGGGT | CAAGGGCATC | 600
| GGGGAGAAGA | CGGCGAGGAA | GCTTCTGGAG | GAGTGGGGGA | GCCTGGAAGC | CCTCCTCAAG | 660
| AACCTGGACC | GGCTGAAGCC | CGCCATCCGG | GAGAAGATCC | TGGCCCACAT | GGACGATCTG | 720
| AAGCTCTCCT | GGGACCTGGC | CAAGGTGCGC | ACCGACCTGC | CCTGGAGGT | GGACTTCGCC | 780
| AAAAGGCGGG | AGCCCGACCG | GGAGAGGCTT | AGGGCCTTTC | TGGAGAGGCT | TGAGTTTGGC | 840
| AGCCTCCTCC | ACGAGTTCGG | CCTTCTGGAA | AGCCCCAAGG | CCCTGGAGGA | GGCCCCTGG | 900
| CCCCCGCCGG | AAGGGGCCTT | CGTGGGCTTT | GTGCTTTCCC | GCAAGGAGCC | CATGTGGGCC | 960
| GATCTTCTGG | CCCTGGCCGC | CGCCAGGGGG | GGCCGGGTCC | ACCGGGCCCC | CGAGCCTTAT | 1020
| AAAGCCCTCA | GGGACCTGAA | GGAGGCGCGG | GGGCTTCTCG | CCAAAGACCT | GAGCGTTCTG | 1080
| GCCCTGAGGG | AAGGCCTTGG | CCTCCCGCCC | GGCGACGACC | CCATGCTCCT | CGCCTACCTC | 1140
| CTGGACCCTT | CCAACACCAC | CCCCGAGGGG | GTGGCCCGGC | GCTACGGCGG | GGAGTGGACG | 1200
| GAGGAGGCGG | GGGAGCGGGC | CGCCCTTTCC | GAGAGGCTCT | TCGCCAACCT | GTGGGGAGG | 1260
| CTTGAGGGGG | AGGAGAGGCT | CCTTTGGCTT | TACCGGGAGG | TGGAGAGGCC | CCTTTCCGCT | 1320
| GTCCTGGCCC | ACATGGAGGC | CACGGGGGTG | CGCCTGGACG | TGGCCTATCT | CAGGGCTTG | 1380
| TCCCTGGAGG | TGGCCGGGGA | GATCGCCCGC | CTCGAGGCCG | AGGTCTTCCG | CCTGGCCGGC | 1440
| CACCCCTTCA | ACCTCAACTC | CCGGGACCAG | CTGGAAAGGG | TCCTCTTTGA | CGAGCTAGGG | 1500
| CTTCCCGCCA | TCGGCAAGAC | GGAGAAGACC | GGCAAGCGCT | CCACCAGCGC | CGCCGTCCTG | 1560
| GAGGCCCTCC | GCGAGGCCCA | CCCCATCGTG | GAGAAGATCC | TGCAGGCATG | CAAGCTTGGC | 1620
| ACTGGCCGTC | GTTTTACAAC | GTCGTGA | | | | 1647

( 2 ) INFORMATION FOR SEQ ID NO:10:

( i ) SEQUENCE CHARACTERISTICS:
  ( A ) LENGTH: 2088 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:10:

| | | | | | |
|---|---|---|---|---|---|
| ATGAATTCGG | GGATGCTGCC | CCTCTTTGAG | CCCAAGGGCC | GGGTCCTCCT | GGTGGACGGC | 60
| CACCACCTGG | CCTACCGCAC | CTTCCACGCC | CTGAAGGGCC | TCACCACCAG | CCGGGGGGAG | 120
| CCGGTGCAGG | CGGTCTACGG | CTTCGCCAAG | AGCCTCCTCA | AGGCCCTCAA | GGAGGACGGG | 180
| GACGCGGTGA | TCGTGGTCTT | TGACGCCAAG | GCCCCCTCCT | TCCGCCACGA | GGCCTACGGG | 240
| GGGTACAAGG | CGGGCCGGGC | CCCCACGCCG | GAGGACTTTC | CCCGGCAACT | CGCCCTCATC | 300
| AAGGAGCTGG | TGGACCTCCT | GGGGCTGGCG | CGCCTCGAGG | TCCCGGGCTA | CGAGGCGGAC | 360
| GACGTCCTGG | CCAGCCTGGC | CAAGAAGGCG | GAAAAGGAGG | GCTACGAGGT | CCGCATCCTC | 420
| ACCGCCGACA | AAGACCTTTA | CCAGCTCCTT | TCCGACCGCA | TCCACGTCCT | CCACCCCGAG | 480
| GGGTACCTCA | TCACCCCGGC | CTGGCTTTGG | GAAAAGTACG | GCCTGAGGCC | CGACCAGTGG | 540
| GCCGACTACC | GGGCCCTGAC | CGGGGACGAG | TCCGACAACC | TTCCCGGGGT | CAAGGGCATC | 600
| GGGGAGAAGA | CGGCGAGGAA | GCTTCTGGAG | GAGTGGGGGA | GCCTGGAAGC | CCTCCTCAAG | 660
| AACCTGGACC | GGCTGAAGCC | CGCCATCCGG | GAGAAGATCC | TGGCCCACAT | GGACGATCTG | 720

| | | | | | |
|---|---|---|---|---|---|
| AAGCTCTCCT | GGGACCTGGC | CAAGGTGCGC | ACCGACCTGC | CCCTGGAGGT | GGACTTCGCC | 780
| AAAAGGCGGG | AGCCCGACCG | GGAGAGGCTT | AGGGCCTTTC | TGGAGAGGCT | TGAGTTTGGC | 840
| AGCCTCCTCC | ACGAGTTCGG | CCTTCTGGAA | AGCCCCAAGG | CCCTGGAGGA | GGCCCCCTGG | 900
| CCCCCGCCGG | AAGGGGCCTT | CGTGGGCTTT | GTGCTTTCCC | GCAAGGAGCC | CATGTGGGCC | 960
| GATCTTCTGG | CCCTGGCCGC | CGCCAGGGGG | GGCCGGGTCC | ACCGGGCCCC | CGAGCCTTAT | 1020
| AAAGCCCTCA | GGGACCTGAA | GGAGGCGCGG | GGGCTTCTCG | CCAAAGACCT | GAGCGTTCTG | 1080
| GCCCTGAGGG | AAGGCCTTGG | CCTCCCGCCC | GGCGACGACC | CCATGCTCCT | CGCCTACCTC | 1140
| CTGGACCCTT | CCAACACCAC | CCCCGAGGGG | GTGGCCCGGC | GCTACGGCGG | GAGTGGACG | 1200
| GAGGAGGCGG | GGGAGCGGGC | CGCCCTTTCC | GAGAGGCTCT | TCGCCAACCT | GTGGGGAGG | 1260
| CTTGAGGGGG | AGGAGAGGCT | CCTTTGGCTT | TACCGGGAGG | TGGAGAGGCC | CCTTTCCGCT | 1320
| GTCCTGGCCC | ACATGGAGGC | CACGGGGGTG | CGCCTGGACG | TGGCCTATCT | CAGGGCCTTG | 1380
| TCCCTGGAGG | TGGCCGGGGA | GATCGCCCGC | CTCGAGGCCG | AGGTCTTCCG | CCTGGCCGGC | 1440
| CACCCCTTCA | ACCTCAACTC | CCGGGACCAG | CTGGAAAGGG | TCCTCTTTGA | CGAGCTAGGG | 1500
| CTTCCCGCCA | TCGGCAAGAC | GGAGAAGACC | GGCAAGCGCT | CCACCAGCGC | CGCCGTCCTG | 1560
| GAGGCCCTCC | GCGAGGCCCA | CCCCATCGTG | GAGAAGATCC | TGCAGTACCG | GGAGCTCACC | 1620
| AAGCTGAAGA | GCACCTACAT | TGACCCCTTG | CCGGACCTCA | TCCACCCCAG | GACGGGCCGC | 1680
| CTCCACACCC | GCTTCAACCA | GACGGCCACG | GCCACGGGCA | GGCTAAGTAG | CTCCGATCCC | 1740
| AACCTCCAGA | ACATCCCCGT | CCGCACCCCG | CTTGGGCAGA | GGATCCGCCG | GGCCTTCATC | 1800
| GCCGAGGAGG | GGTGGCTATT | GGTGGCCCTG | GACTATAGCC | AGATAGAGCT | CAGGGTGCTG | 1860
| GCCCACCTCT | CCGGCGACGA | GAACCTGATC | CGGGTCTTCC | AGGAGGGGCG | GGACATCCAC | 1920
| ACGGAGACCG | CCAGCTGGAT | GTTCGGCGTC | CCCCGGGAGG | CCGTGGACCC | CCTGATGCGC | 1980
| CGGGCGGCCA | AGACCATCAA | CTTCGGGGTC | CTCTACGGCA | TGTCGGCCCA | CCGCCTCTCC | 2040
| CAGGAGCTAG | CTAGCCATCC | CTTACGAGGA | GGCCCAGGCC | TTCATTGA | | 2088

( 2 ) INFORMATION FOR SEQ ID NO:11:

( i ) SEQUENCE CHARACTERISTICS:
( A ) LENGTH: 962 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| ATGAATTCGG | GGATGCTGCC | CCTCTTTGAG | CCCAAGGGCC | GGGTCCTCCT | GGTGGACGGC | 60
| CACCACCTGG | CCTACCGCAC | CTTCCACGCC | CTGAAGGGCC | TCACCACCAG | CCGGGGGGAG | 120
| CCGGTGCAGG | CGGTCTACGG | CTTCGCCAAG | AGCCTCCTCA | AGGCCCTCAA | GGAGGACGGG | 180
| GACGCGGTGA | TCGTGGTCTT | TGACGCCAAG | GCCCCCTCCT | TCCGCCACGA | GGCCTACGGG | 240
| GGGTACAAGG | CGGGCCGGGC | CCCCACGCCG | GAGGACTTTC | CCCGGCAACT | CGCCCTCATC | 300
| AAGGAGCTGG | TGGACCTCCT | GGGGCTGGCG | CGCCTCGAGG | TCCCGGGCTA | CGAGGCGGAC | 360
| GACGTCCTGG | CCAGCCTGGC | CAAGAAGGCG | GAAAAGGAGG | CTACGAGGT | CCGCATCCTC | 420
| ACCGCCGACA | AAGACCTTTA | CCAGCTTCTT | TCCGACCGCA | TCCACGTCCT | CCACCCCGAG | 480
| GGGTACCTCA | TCACCCCGGC | CTGGCTTTGG | GAAAAGTACG | GCCTGAGGCC | CGACCAGTGG | 540
| GCCGACTACC | GGGCCCTGAC | CGGGGACGAG | TCCGACAACC | TTCCCGGGGT | CAAGGGCATC | 600

| GGGGAGAAGA | CGGCGAGGAA | GCTTCTGGAG | GAGTGGGGGA | GCCTGGAAGC | CCTCCTCAAG | 660 |
| AACCTGGACC | GGCTGAAGCC | CGCCATCCGG | GAGAAGATCC | TGGCCCACAT | GGACGATCTG | 720 |
| AAGCTCTCCT | GGGACCTGGC | CAAGGTGCGC | ACCGACCTGC | CCCTGGAGGT | GGACTTCGCC | 780 |
| AAAAGGCGGG | AGCCCGACCG | GGAGAGGCTT | AGGGCCTTTC | TGGAGAGGCT | TGAGTTTGGC | 840 |
| AGCCTCCTCC | ACGAGTTCGG | CCTTCTGGAA | AGCCCAAGT | CATGGAGGGG | GTGTATCCCC | 900 |
| TGGCCGTGCC | CCTGGAGGTG | GAGGTGGGGA | TAGGGAGGA | CTGGCTCTCC | GCCAAGGAGT | 960 |
| GA | | | | | | 962 |

(2) INFORMATION FOR SEQ ID NO:12:

(i) SEQUENCE CHARACTERISTICS:
    (A) LENGTH: 1600 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:12:

| ATGGAATTCG | GGGATGCTGC | CCCTCTTTGA | GCCCAAGGGC | CGGGTCCTCC | TGGTGGACGG | 60 |
| CCACCACCTG | GCCTACCGCA | CCTTCCACGC | CCTGAAGGGC | CTCACCACCA | GCCGGGGGA | 120 |
| GCCGGTGCAG | GCGGTCTACG | GCTTCGCCAA | GAGCCTCCTC | AAGGCCCTCA | AGGAGGACGG | 180 |
| GGACGCGGTG | ATCGTGGTCT | TTGACGCCAA | GGCCCCCTCC | TTCCGCCACG | AGGCCTACGG | 240 |
| GGGGTACAAG | GCGGGCCGGG | CCCCCACGCC | GGAGGACTTT | CCCCGGCAAC | TCGCCCTCAT | 300 |
| CAAGGAGCTG | GTGGACCTCC | TGGGGCTGGC | GCGCCTCGAG | GTCCCGGGCT | ACGAGGCGGA | 360 |
| CGACGTCCTG | GCCAGCCTGG | CCAAGAAGGC | GGAAAAGGAG | GGCTACGAGG | TCCGCATCCT | 420 |
| CACCGCCGAC | AAAGACCTTT | ACCAGCTCCT | TTCCGACCGC | ATCCACGTCC | TCCACCCCGA | 480 |
| GGGGTACCTC | ATCACCCCGG | CCTGGCTTTG | GGAAAAGTAC | GGCCTGAGGC | CCGACCAGTG | 540 |
| GGCCGACTAC | CGGGCCCTGA | CCGGGGACGA | GTCCGACAAC | CTTCCCGGGG | TCAAGGGCAT | 600 |
| CGGGGAGAAG | ACGGCGAGGA | AGCTTCTGGA | GGAGTGGGGG | AGCCTGGAAG | CCCTCCTCAA | 660 |
| GAACCTGGAC | CGGCTGAAGC | CCGCCATCCG | GGAGAAGATC | CTGGCCCACA | TGGACGATCT | 720 |
| GAAGCTCTCC | TGGGACCTGG | CCAAGGTGCG | CACCGACCTG | CCCCTGGAGG | TGGACTTCGC | 780 |
| CAAAAGGCGG | GAGCCCGACC | GGGAGAGGCT | TAGGGCCTTT | CTGGAGAGGC | TTGAGTTTGG | 840 |
| CAGCCTCCTC | CACGAGTTCG | GCCTTCTGGA | AAGCCCCAAG | ATCCGCCGGG | CCTTCATCGC | 900 |
| CGAGGAGGGG | TGGCTATTGG | TGGCCCTGGA | CTATAGCCAG | ATAGAGCTCA | GGGTGCTGGC | 960 |
| CCACCTCTCC | GGCGACGAGA | ACCTGATCCG | GGTCTTCCAG | GAGGGGCGGG | ACATCCACAC | 1020 |
| GGAGACCGCC | AGCTGGATGT | CGGCGTCCC | CCGGGAGGCC | GTGGACCCCC | TGATGCGCCG | 1080 |
| GGCGGCCAAG | ACCATCAACT | TCGGGGTCCT | CTACGGCATG | TCGGCCCACC | GCCTCTCCCA | 1140 |
| GGAGCTAGCC | ATCCCTTACG | AGGAGGCCCA | GGCCTTCATT | GAGCGCTACT | TTCAGAGCTT | 1200 |
| CCCCAAGGTG | CGGGCCTGGA | TTGAGAAGAC | CCTGGAGGAG | GGCAGGAGGC | GGGGGTACGT | 1260 |
| GGAGACCCTC | TTCGGCCGCC | GCCGCTACGT | GCCAGACCTA | GAGGCCCGGG | TGAAGAGCGT | 1320 |
| GCGGGAGGCG | GCCGAGCGCA | TGGCCTTCAA | CATGCCCGTC | CGGGGCACCG | CCGCCGACCT | 1380 |
| CATGAAGCTG | GCTATGGTGA | AGCTCTTCCC | CAGGCTGGAG | GAAATGGGGG | CCAGGATGCT | 1440 |
| CCTTCAGGTC | CACGACGAGC | TGGTCCTCGA | GGCCCCAAAA | GAGAGGGCGG | AGGCCGTGGC | 1500 |
| CCGGCTGGCC | AAGGAGGTCA | TGGAGGGGGT | GTATCCCCTG | GCCGTGCCCC | TGGAGGTGGA | 1560 |
| GGTGGGGATA | GGGGAGGACT | GGCTCTCCGC | CAAGGAGTGA | | | 1600 |

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
CACGAATTCG GGGATGCTGC CCCTCTTTGA GCCCAA                                    36
```

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
GTGAGATCTA TCACTCCTTG GCGGAGAGCC AGTC                                      34
```

( 2 ) INFORMATION FOR SEQ ID NO:15:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
TAATACGACT CACTATAGGG AGACCGGAAT TCGAGCTCGC CCGGGCGAGC TCGAATTCCG           60

TGTATTCTAT AGTGTCACCT AAATCGAATT C                                         91
```

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
TAATACGACT CACTATAGGG                                                      20
```

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
GAATTCGATT TAGGTGACAC TATAGAA                                              27
```

( 2 ) INFORMATION FOR SEQ ID NO:18:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
GTAATCATGG TCATAGCTGG TAGCTTGCTA C                                         31
```

( 2 ) INFORMATION FOR SEQ ID NO:19:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

| | | | | |
|---|---|---|---|---|
| GGATCCTCTA | GAGTCGACCT | GCAGGCATGC | CTACCTTGGT | AG | 42 |

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GGATCCTCTA GAGTCGACCT GCAGGCATGC       30

( 2 ) INFORMATION FOR SEQ ID NO:21:

( i ) SEQUENCE CHARACTERISTICS:
        ( A ) LENGTH: 2502 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:21:

| | | | | | |
|---|---|---|---|---|---|
| ATGAATTCGG | GGATGCTGCC | CCTCTTTGAG | CCCAAGGGCC | GGGTCCTCCT | GGTGGACGGC | 60 |
| CACCACCTGG | CCTACCGCAC | CTTCCACGCC | CTGAAGGGCC | TCACCACCAG | CCGGGGGGAG | 120 |
| CCGGTGCAGG | CGGTCTACGG | CTTCGCCAAG | AGCCTCCTCA | AGGCCCTCAA | GGAGGACGGG | 180 |
| GACGCGGTGA | TCGTGGTCTT | TGACGCCAAG | GCCCCTCCT | TCCGCCACGA | GGCCTACGGG | 240 |
| GGGTACAAGG | CGGGCCGGGC | CCCCACGCCG | GAGGACTTTC | CCCGGCAACT | CGCCCTCATC | 300 |
| AAGGAGCTGG | TGGACCTCCT | GGGGCTGGCG | CGCCTCGAGG | TCCCGGGCTA | CGAGGCGGAC | 360 |
| GACGTCCTGG | CCAGCCTGGC | CAAGAAGGCG | GAAAAGGAGG | CTACGAGGT | CCGCATCCTC | 420 |
| ACCGCCGACA | AAGACCTTTA | CCAGCTCCTT | TCCGACCGCA | TCCACGTCCT | CCACCCCGAG | 480 |
| GGGTACCTCA | TCACCCCGGC | CTGGCTTTGG | GAAAAGTACG | GCCTGAGGCC | CGACCAGTGG | 540 |
| GCCGACTACC | GGGCCCTGAC | CGGGGACGAG | TCCGACAACC | TTCCCGGGGT | CAAGGGCATC | 600 |
| GGGGAGAAGA | CGGCGAGGAA | GCTTCTGGAG | GAGTGGGGGA | GCCTGGAAGC | CCTCCTCAAG | 660 |
| AACCTGGACC | GGCTGAAGCC | CGCCATCCGG | GAGAAGATCC | TGGCCCACAT | GGACGATCTG | 720 |
| AAGCTCTCCT | GGGACCTGGC | CAAGGTGCGC | ACCGACCTGC | CCTGGAGGT | GGACTTCGCC | 780 |
| AAAAGGCGGG | AGCCCGACCG | GGAGAGGCTT | AGGGCCTTTC | TGGAGAGGCT | TGAGTTTGGC | 840 |
| AGCCTCCTCC | ACGAGTTCGG | CCTTCTGGAA | AGCCCAAGG | CCCTGGAGGA | GGCCCCCTGG | 900 |
| CCCCCGCCGG | AAGGGGCCTT | CGTGGGCTTT | GTGCTTTCCC | GCAAGGAGCC | CATGTGGGCC | 960 |
| GATCTTCTGG | CCCTGGCCGC | CGCCAGGGGG | GGCCGGGTCC | ACCGGGCCCC | CGAGCCTTAT | 1020 |
| AAAGCCCTCA | GGGACCTGAA | GGAGGCGCGG | GGGCTTCTCG | CCAAAGACCT | GAGCGTTCTG | 1080 |
| GCCCTGAGGG | AAGGCCTTGG | CCTCCCGCCC | GGCGACGACC | CCATGCTCCT | CGCCTACCTC | 1140 |
| CTGGACCCTT | CCAACACCAC | CCCCGAGGGG | GTGGCCCGGC | GCTACGGCGG | GGAGTGGACG | 1200 |

| | | | | | |
|---|---|---|---|---|---|
| GAGGAGGCGG | GGGAGCGGGC | CGCCCTTTCC | GAGAGGCTCT | TCGCCAACCT | GTGGGGAGG | 1260 |
| CTTGAGGGGG | AGGAGAGGCT | CCTTTGGCTT | TACCGGGAGG | TGGAGAGGCC | CCTTTCCGCT | 1320 |
| GTCCTGGCCC | ACATGGAGGC | CACGGGGGTG | CGCCTGGACG | TGGCCTATCT | CAGGGCCTTG | 1380 |
| TCCCTGGAGG | TGGCCGGGGA | GATCGCCCGC | CTCGAGGCCG | AGGTCTTCCG | CCTGGCCGGC | 1440 |
| CACCCCTTCA | ACCTCAACTC | CCGGGACCAG | CTGGAAAGGG | TCCTCTTTGA | CGAGCTAGGG | 1500 |
| CTTCCCGCCA | TCGGCAAGAC | GGAGAAGACC | GGCAAGCGCT | CCACCAGCGC | CGCCGTCCTG | 1560 |
| GAGGCCCTCC | GCGAGGCCCA | CCCCATCGTG | GAGAAGATCC | TGCAGTACCG | GGAGCTCACC | 1620 |
| AAGCTGAAGA | GCACCTACAT | TGACCCCTTG | CCGGACCTCA | TCCACCCCAG | GACGGGCCGC | 1680 |
| CTCCACACCC | GCTTCAACCA | GACGGCCACG | GCCACGGGCA | GGCTAAGTAG | CTCCGATCCC | 1740 |
| AACCTCCAGA | ACATCCCCGT | CCGCACCCCG | CTTGGGCAGA | GGATCCGCCG | GGCCTTCATC | 1800 |
| GCCGAGGAGG | GGTGGCTATT | GGTGGCCCTG | GACTATAGCC | AGATAGAGCT | CAGGGTGCTG | 1860 |
| GCCCACCTCT | CCGGCGACGA | GAACCTGATC | CGGGTCTTCC | AGGAGGGGCG | GGACATCCAC | 1920 |
| ACGGAGACCG | CCAGCTGGAT | GTTCGGCGTC | CCCCGGGAGG | CCGTGGACCC | CCTGATGCGC | 1980 |
| CGGGCGGCCA | AGACCATCAA | CTTCGGGGTC | CTCTACGGCA | TGTCGGCCCA | CCGCCTCTCC | 2040 |
| CAGGAGCTAG | CCATCCCTTA | CGAGGAGGCC | CAGGCCTTCA | TTGAGCGCTA | CTTTCAGAGC | 2100 |
| TTCCCCAAGG | TGCGGGCCTG | GATTGAGAAG | ACCCTGGAGG | AGGGCAGGAG | GCGGGGGTAC | 2160 |
| GTGGAGACCC | TCTTCGGCCG | CCGCCGCTAC | GTGCCAGACC | TAGAGGCCCG | GGTGAAGAGC | 2220 |
| GTGCGGGAGG | CGGCCGAGCG | CATGGCCTTC | AACATGCCCG | TCCGGGGCAC | CGCCGCCGAC | 2280 |
| CTCATGAAGC | TGGCTATGGT | GAAGCTCTTC | CCCAGGCTGG | AGGAAATGGG | GGCCAGGATG | 2340 |
| CTCCTTCAGG | TCCACGACGA | GCTGGTCCTC | GAGGCCCCAA | AAGAGAGGGC | GGAGGCCGTG | 2400 |
| GCCCGGCTGG | CCAAGGAGGT | CATGGAGGGG | GTGTATCCCC | TGGCCGTGCC | CCTGGAGGTG | 2460 |
| GAGGTGGGGA | TAGGGAGGA | CTGGCTCTCC | GCCAAGGAGT | GA | | 2502 |

( 2 ) INFORMATION FOR SEQ ID NO:22:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

| | |
|---|---|
| GATTTAGGTG ACACTATAG | 19 |

( 2 ) INFORMATION FOR SEQ ID NO:23:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

| | | | | | |
|---|---|---|---|---|---|
| CGGACGAACA | AGCGAGACAG | CGACACAGGT | ACCACATGGT | ACAAGAGGCA | AGAGAGACGA | 60 |
| CACAGCAGAA AC | | | | | | 72 |

( 2 ) INFORMATION FOR SEQ ID NO:24:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

GTTTCTGCTG TGTCGTCTCT CTTGCCTCTT GTACCATGTG GTACCTGTGT CGCTGTCTCG    60

CTTGTTCGTC    70

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GACGAACAAG CGAGACAGCG    20

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GTTTCTGCTG TGTCGTCTCT CTTG    24

( 2 ) INFORMATION FOR SEQ ID NO:27:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CCTCTTGTAC CATGTGGTAC CTGTGTCGCT GTCTCGCTTG TTCGTC    46

( 2 ) INFORMATION FOR SEQ ID NO:28:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

ACACAGGTAC CACATGGTAC AAGAGGCAAG AGAGACGACA CAGCAGAAAC    50

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

Met Ala Ser Met Thr Gly Gly Gln Gln Met Gly Arg Ile Asn Ser
1               5                   10                  15

NUCLEIC ACID ENCODING SYNTHESIS-DEFICIENT THERMOSTABLE DNA POLYMERASE

This is a continuation-in-part of application Ser. No. 07/986,330, filed Dec. 12, 1992, now abandoned.

FIELD OF THE INVENTION

The present invention relates to means for cleaving a nucleic acid cleavage structure in a site-specific manner. In particular, the present invention relates to a cleaving enzyme having 5' nuclease activity without interfering nucleic acid synthetic ability.

BACKGROUND OF THE INVENTION

The detection of specific nucleic acid sequences has been utilized to diagnose the presence of vital or bacterial nucleic acid sequences indicative of an infection, the presence of variants or alleles of mammalian genes associated with disease and the identification of the source of nucleic acids found in forensic samples and in paternity determinations.

The detection of specific nucleic acid sequences has been achieved typically by hybridization. Hybridization methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et at., Proc. Natl. Acad. Sci. USA 46:461 (1960) have been followed by the refinement of this process into an essential tool of modern biology.

Initial hybridization studies, such as those performed by Hayashi et al., Proc. Natl. Acad. Sci. USA 50:664 (1963), were formed in solution. Further development led to the immobilization of the target DNA or RNA on solid supports. With the discovery of specific restriction endonucleases by Smith and Wilcox, J. Mol. Biol. 51:379 (1970), it became possible to isolate discrete fragments of DNA. Utilization of immobilization techniques, such as those described by Southern, J. Mol. Biol. 98:503 (1975), in combination with restriction enzymes, has allowed for the identification by hybridization of single copy genes among a mass of fractionated, genomic DNA.

In spite of the progress made in hybridization methodology, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

1. Inefficient Hybridization

It is experimentally observed that only a fraction of the possible number of probe-target complexes are formed in a hybridization reaction. This is particularly true with short oligonucleotide probes (less than 100 bases in length). Them are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

The immobilization of target nucleic acids to solid surfaces such as nylon or nitrocellulose is a common practice in molecular biology. Immobilization formats eliminate the reassociation problem that can occur between complementary strands of target molecules, but not the problems associated with secondary structure effects. However, these mixed phase formats (i.e., Southern hybridization or dot blot hybridization) require time consuming fixation procedures. The hybridization reaction itself is kinetically much slower than a solution phase hybridization reaction. Together, the fixation and hybridization procedures require a minimum of several hours to several days to perform. Additionally, the standard immobilization procedures are often inefficient and result in the attachment of many of the target molecules to multiple portions on the solid surface, rendering them incapable of subsequent hybridization to probe molecules. Overall, these combined effects result in just a few percent of the initial target molecules being bound by probes in a hybridization reaction.

2. Low Target Sequence Concentration

In laboratory experiments, purified probes and targets are used. The concentrations of these probes and targets, moreover, can be adjusted according to the sensitivity required. By contrast, the goal in the application of hybridization to medical diagnostics is the detection of a target sequence from a mixture of genomic DNA. Usually the DNA fragment containing the target sequence is in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. See Wallace et at., Biochimie 67:755 (1985). In the case of radioactive oligonucleotide probes, only extremely high specific activities are found to show satisfactory results. See Studencki and Wallace, DNA 3:1 (1984) and Studencki et al., Human Genetics 37:42 (1985).

Polymerase chain reaction (PCR) technology provides an alternate approach to the problems of low target sequence concentration. PCR can be used to directly increase the concentration of the target prior to hybridization. In U.S. Pat. Nos. 4,683,195 and 4,683,202, Mullis et al. describe a method for increasing the concentration of a segment of target sequence in a mixture of genomic DNA without cloning or purification.

This process for amplifying the target sequence consists of introducing a molar excess of two oligonucleotide primers to the DNA mixture containing the desired target sequence. The two primers are complementary to their respective strands of the double-stranded sequence. The mixture is denatured and then allowed to hybridize. Following hybridization, the primers are extended with polymerase so as to form complementary strands. The steps of denaturation, hybridization, and polymerase extension can be repeated as often as needed to obtain relatively high concentration of a segment of the desired target sequence. The length of the segment of the desired target sequence is determined by the relative positions of the primers with respect to each other, and, therefore, this length is a controllable parameter. By virtue of the repeating aspect of the process, the method is referred to by the inventors as the "Polymerase Chain Reaction" (or PCR). Because the desired segment of the target sequence become the dominant sequences (in terms of concentration) in the mixture, they are said to be "PCR-amplified."

However the PCR process is susceptible to the production of non-target fragments during the amplification process. Spurious extension of primers at partially complementary regions occurs during PCR reactions. Factors influencing the specificity of the amplification process include: a) the concentration of the target sequence in the DNA to be analyzed; b) the concentration of the $Mg^{++}$, polymerase enzyme and primers; c) the number of cycles of amplification performed; and d) the temperatures and times used at the various steps in the amplification process (*PCR Technology—Principles and Applications for DNA Amplification* (H. A. Erlich, Ed.), Stockton Press, New York pp. 7–16 (1989). When the specific target sequence is present in low concentration in the sample DNA more non-target fragments are produced. Low target concentration is often the norm in clinical samples where the target may be present as a single copy in the genome or where very little viral DNA is present as in HIV infections.

Because amplification products are produced which do not represent the specific target sequence to be detected, the products of a PCR reaction must be analyzed using a probe specific for the target DNA. The detection of specific amplification products has been accomplished by the hybridization of a probe specific for the target sequence to the reaction products immobilized upon a solid support. Such a detection method is cumbersome and is subject to the same problems associated with the detection of any target molecule by hybridization as discussed above.

A non-hybridization based detection assay for specific PCR products has been described by Holland et al., Proc. Natl. Acad. Sci. USA 88:7276 (1991). In this detection system, the 5' nuclease activity of wild type DNA polymerase from *Thermus aquaticus* ("DNAPTaq") is used to generate a specific detectable product concomitantly with amplification. An oligonucleotide probe specific for the target DNA is labeled on the 5' end and added to the PCR reaction along with the unlabelled primers used for extension of the target to be amplified. The 5' nuclease activity of the DNAPTaq cleaves the labeled probe annealed to the target DNA before the extension of the primer is complete, generating a smaller fragment of the probe. This detection system requires that amplification be performed upon the sample to produce the specific detection product. This is slow and requires cumbersome equipment.

A minimum of 100 starting copies (i.e., copy number prior to amplification) of target DNA were used in this detection system; it is not clear whether fewer starting copies of target DNA will yield detectable results using this method. Very low copy number may be a problem for some clinical samples where very little DNA is obtained due to restrictions on sample size (blood from neonates or fetuses, forensic samples, etc.).

While such an assay is an improvement over earlier hybridization detection methods, it still requires that a PCR reaction be performed upon the sample and it possesses certain inherent problems. One such problem is that this system requires that the detection probe must bind to the target DNA before primer extension occurs. If extension occurs first, the probe binding site will be unavailable and no digestion of the probe will occur and therefore no detectable signal will be produced. To overcome this problem the user must vary the relative amounts of primer and probe or manipulate the sequence and length of the probe. The need for such optimization may prove too burdensome for clinical laboratories.

3. Partial Complementarity

Hybridization, regardless of the method used, requires some degree of complementarity between the sequence being assayed (the target sequence) and the fragment of DNA used to perform the test (the probe). (Of course, one can obtain binding without any complementarity but this binding is nonspecific and to be avoided.) For many diagnostic applications, it is not important to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the method of hybridization distinguish between variant target sequences. For example, it may be of interest that a particular allelic variant of a pathogen is present. These normal and variant sequences may differ in one or more bases.

There are other applications that may require that the hybridization method distinguish between partial and complete complementarity. It may be of interest to detect genetic polymorphisms. Human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

Unless combined with other techniques (such as restriction enzyme analysis), hybridization methods that allow for the same level of hybridization in the case of both partial as well as complete complementarity are unsuited for such applications; the probe will hybridize to both the normal and variant target sequence.

Methods have been devised to enable discrimination between partial and complete complementarity. One approach is to take advantage of the temperature requirements of the specific hybridization under study. In typical melting curve experiments, such as those described by Wallace et al., Nucl. Acids Res. 6:3543 (1979) and Nucl. Acids Res. 9:879 (1981), an immobilized probe-target complex is washed at increasing temperatures under non-equilibrium conditions. It is observed that partially complementary probe-target complexes display a lower thermal stability as compared to completely complementary probe-target complexes. This difference can be used, therefore, to determine whether the probe has hybridized to the partially complementary or the completely complementary target sequence.

Conventional methods that utilize the temperature dependant nature of hybridization are artful. The application of this method for the discrimination of single base mutations in human genomic targets is limited to the use of short oligonucleotide probes where the hybridization interaction with the target sequence is in the size range of 17 bases to 25 bases in length. The lower length limit is determined by the random probability of having a complement to the probe in the human genome, which is greater than 1 for a random 16 base pair interaction, but less than 1 for interactions 17 bases or longer in length. The upper limit is one of practicality. It is difficult to differentiate single base mismatches on the basis of thermal stability for interactions longer than 25 bases in length. These conventional methods are, unfortunately also time consuming. Probe concentrations in these experiments are approximately $1-5\times10^{-10}$M. These concentrations are empirically derived; they minimize the use of probe and simultaneously provide sufficient discrimination to distinguish single copy genes utilizing probes of approximately 20 nucleotides in length. Hybridization times are two to ten hours at these concentrations. After hybridization, several washes of varying stringency are employed to remove excess probe, non-specifically bound probe, and probe bound to partially complementary sequences in the target genome. Careful control of these wash steps is necessary, since the signal (specifically bound probe) to noise (non-specifically bound probe) ratio of the experiment is ultimately determined by the wash procedures.

No detection method heretofore described has solved all three of the problems discussed above. The PCR process solves the problem of low target concentration. However, the specific detection of PCR products by any hybridization method is subject to the same problems associated with the detection of any target molecules. The detection of single base differences between PCR targets was initially accomplished through the use of a restriction enzyme analysis of the hybridization complexes formed between oligonucleotide probes and PCR targets. This technique is limited by that fact that restriction enzymes do not exist that are sequence independent. More recent studies have achieved discrimination without restriction enzymes, however these studies have involved the inefficient immobilization of target nucleic acids to solid surfaces [dot blot hybridization; Saiki et al., Nature 324:163 (1986)].

Another method for the detection of allele-specific variants is disclosed by Kwok et al., Nucl. Acids Res. 18:999 (1990). This method is based upon the fact that it is difficult for a DNAP to synthesize a DNA strand when there is a mismatch between the template strand and the primer. The mismatch acts to prevent the extension thereby preventing the amplification of a target DNA that is not perfectly complementary to the primer used in a PCR reaction. While an allele-specific variant may be detected by the use of a primer that is perfectly matched with only one of the possible alleles, this method of detection is artful and has limitations. Particularly troublesome is the fact that the base composition of the mismatch influences the ability to prevent extension across the mismatch. Certain mismatches do not prevent extension or have only a minimal effect.

An ideal method of detecting specific target DNAs would allow detection without the need to amplify the sample DNA first and would allow the detection of target sequences which are present in low copy numbers in the DNA sample. This ideal method would also allow the discrimination between variants of the target sequence such that single base variations between alleles of mammalian genes can be discerned.

One object of the present invention is to provide a method of detection of specific nucleic acid sequences that solves the above-named problems.

SUMMARY OF THE INVENTION

The present invention relates to means for cleaving a nucleic acid cleavage structure in a site-specific manner. In particular, the present invention relates to a cleaving enzyme having 5' nuclease activity without interfering nucleic acid synthetic ability.

In one embodiment, the means for cleaving is a cleaving enzyme comprising synthesis-deficient DNA polymerases. These polymerases form the basis of a novel method of detection of specific nucleic acid sequences. The present invention contemplates use of the novel detection method for, among other uses, clinical diagnostic purposes.

In one embodiment, the present invention contemplates a DNA sequence encoding a DNA polymerase altered in sequence relative to the native sequence such that it exhibits altered DNA synthetic activity from that of the native DNA polymerase. It is preferred that the encoded DNA polymerase is altered such that it exhibits reduced synthetic activity from that of the native DNA polymerase. In this manner, the polymerase of the invention retains 5' nuclease activity, leaving it capable of cleaving nucleic acids in a structure-specific manner in the absence of interfering synthetic activity.

It is not intended that the invention be limited by the nature of the alteration necessary to render the polymerase synthesis deficient nor the extent of the deficiency. The present invention contemplates altered structure (primary, secondary, etc.) as well as native structure inhibited by synthesis inhibitors.

Where the structure is altered, it is not intended that the invention be limited by the means by which the structure of the polymerase is altered. In one embodiment, the alteration of the native DNA sequence comprises a change in a single nucleotide. In another embodiment, the alteration of the native DNA sequence comprises a deletion of one or more nucleotides. In yet another embodiment, the alteration of the native DNA sequence comprises an insertion of one or more nucleotides. In either of these cases, the change in DNA sequence may manifest itself in a change in amino acid sequence.

The present invention contemplates polymerases from a variety of sources. The preferred polymerases are thermostable. Thermostable polymerases are contemplated as particularly useful in that they operate at temperatures where nucleic acid hybridization is extremely specific, allowing for allele-specific detection (including single-base mismatches). In one embodiment, the thermostable polymerases are selected from the group consisting of altered polymerases derived from the native polymerases of *Thermus aquaticus, Thermus flavus* and *Thermus thermophilus*.

As noted above, the present invention contemplates the use of altered polymerases in a detection method. In one embodiment, the present invention contemplates a method of detecting the presence of a specific target DNA molecule comprising: a) providing: i) a target nucleic acid, ii) a first oligonucleotide complementary to a first portion of said target nucleic acid, and iii) a second oligonucleotide, a region of which is complementary to a second portion of said target nucleic acid, said non-complementary region of said second oligonucleotide providing a single-stranded arm at its 5' end; b) mixing said target nucleic acid, said first oligonucleotide and said second oligonucleotide under conditions wherein said first oligonucleotide and the 3' end of said second oligonucleotide are annealed to said target DNA sequence so as to create a first cleavage structure; c) providing a cleavage means under conditions such that cleavage of said first cleavage structure occurs preferentially at a site located within said second oligonucleotide in a manner dependent upon the annealing of said first and second oligonucleotides on said target nucleic acid, thereby liberating the single-stranded arm of said second oligonucleotide generating a third oligonucleotide; d) providing a first hairpin structure having a single-stranded 3' arm and a single-stranded 5' arm under conditions wherein said third oligonucleotide anneals to said single-stranded 3' arm of said first hairpin thereby creating a second cleavage structure; e) providing conditions under which cleavage of said second cleavage structure occurs by said cleavage means liberating the single-stranded 5' arm of said second cleavage structure so as to create reaction products comprising a fourth oligonucleotide and a first cleaved hairpin detection molecule; f) providing a second hairpin structure having a single-stranded 3' arm and a single-stranded 5' arm under conditions wherein said fourth oligonucleotide anneals to the single-stranded 3' arm of said second hairpin thereby creating a third cleavage structure; g) providing conditions under which cleavage of said third cleavage structure occurs by said cleavage means, liberating the single-stranded 5' arm of said third cleavage structure so as to create reaction products comprising generating a fifth oligonucleotide identical in sequence to said third oligonucleotide and a second cleaved hairpin detection molecule; and h) detecting the presence of said first and second cleaved hairpin detection molecules.

In one embodiment, the detection method of the present invention allows the detection of specific target nucleic acid sequences present in a sample without the need to amplify the number of target copies prior to detection. In this embodiment, steps d) through g) of the method are repeated at least once.

In a preferred embodiment, the cleavage means comprises a cleavage enzyme comprising an altered thermostable DNA polymerase having reduced synthesis capability. While a complete absence of synthesis is not required, it is desired that cleavage reactions occur in the absence of polymerase activity at a level where it interferes with the discrimination needed for detection.

While the cleavage of the detection method can be independent of the annealing of the oligonucleotides, it is preferred that the cleavage is primer-dependent. In other words, it is desired that the cleavage reactions of steps c), e) and g) will not occur absent the annealing of said first oligonucleotide, said third oligonucleotide and said fourth oligonucleotide, respectively.

While cleavage is site-specific, the present invention allows for cleavage at a variety of sites. In one embodiment, the cleavage reaction of step c) occurs within the annealed portion of said second oligonucleotide. In another embodiment, the cleavage reaction of step c) occurs within the non-annealed portion of said second oligonucleotide.

DESCRIPTION OF THE DRAWINGS

Figure 2D:
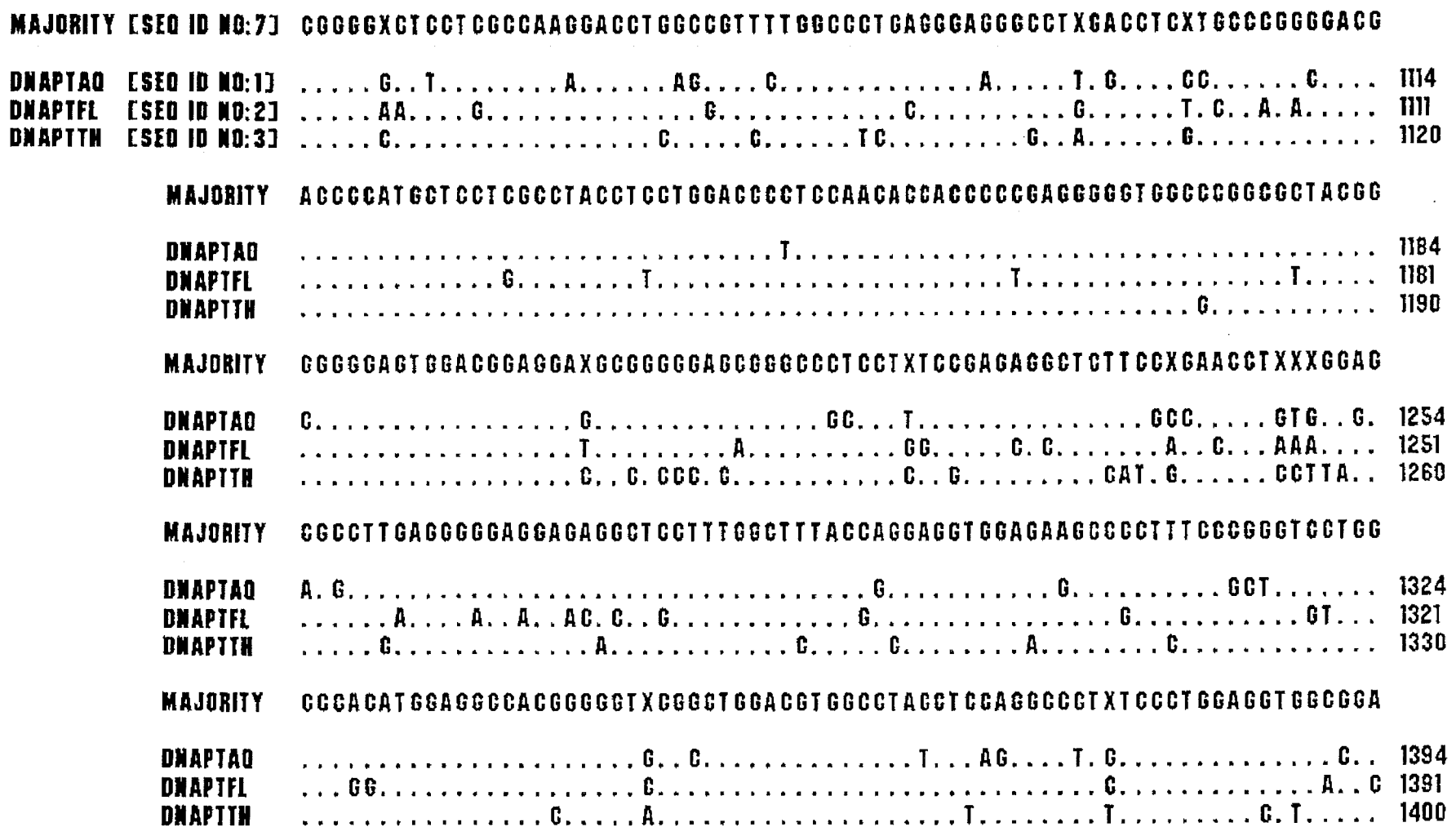
Figure 2E:
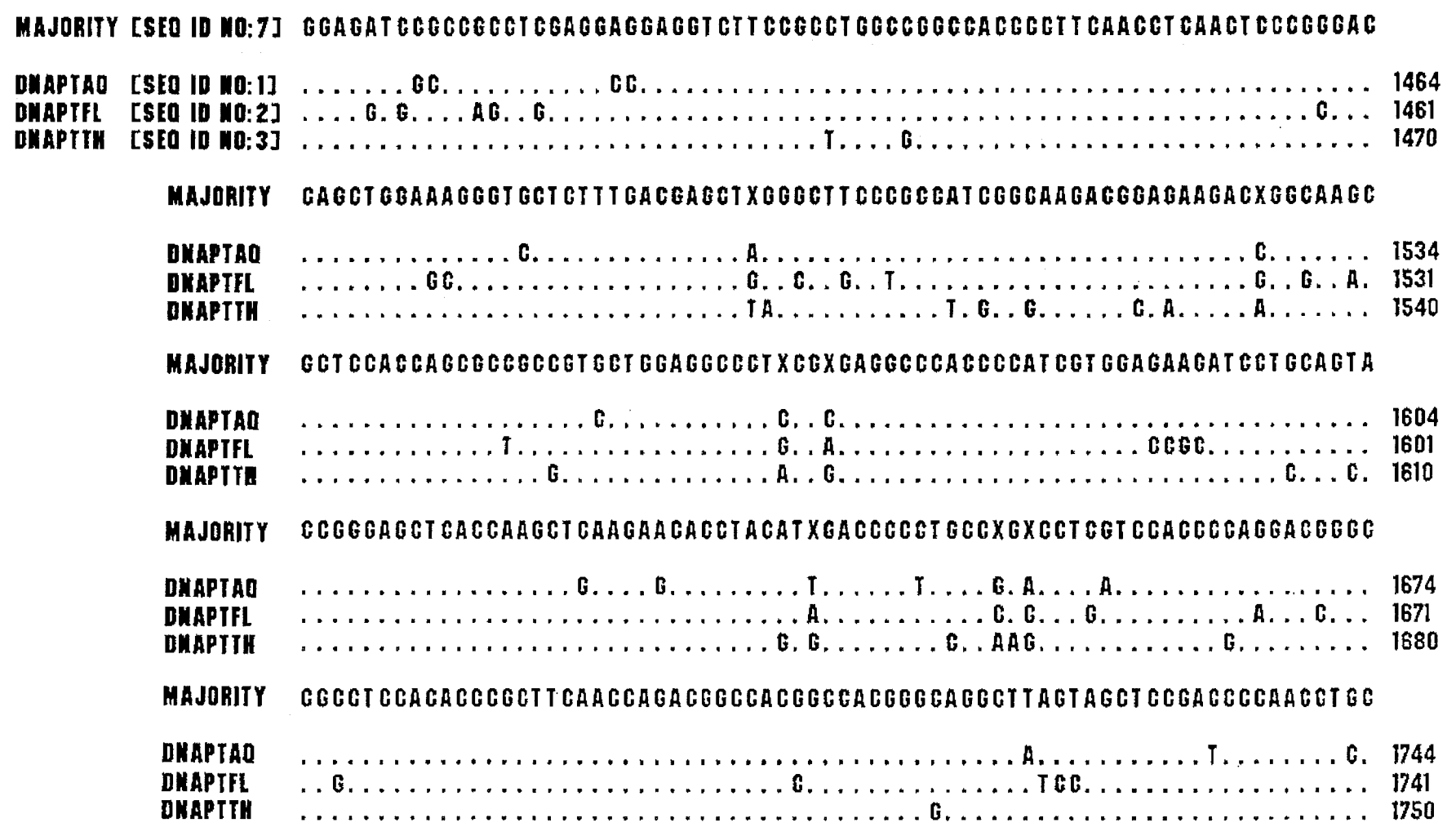
Figure 2G:
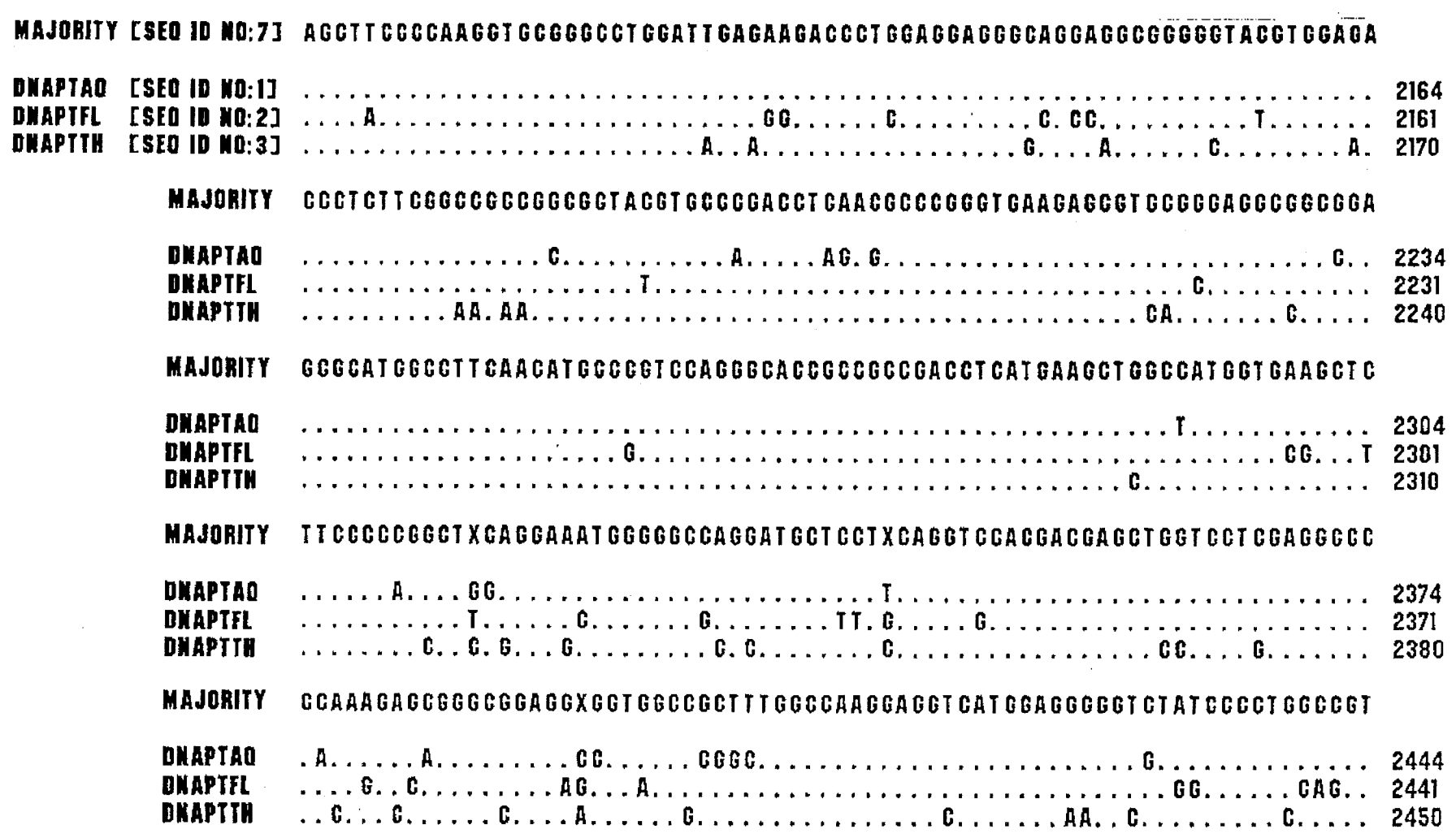

FIG. 2 is a comparison of the nucleotide structure of DNAPs isolated from *Thermus aquaticus*, (SEQ ID NO:1) *Thermus flavus* (SEQ ID NO:2) and *Thermus thermophilus;* (SEQ ID NO:3) the consensus sequence (SEQ ID NO:4) is shown at the top of each row.

FIG. 3 is a comparison of the amino acid sequence of the DNAP isolated from *Thermus aquaticus*, (SEQ ID NO:4) *Thermus flavus*, (SEQ ID NO:5) and *Thermus thermophilus;* (SEQ ID NO:6) the consensus sequence (SEQ ID NO:8) is shown at the top of each row.

FIGS. 4A–F are a set of diagrams of wild-type and synthesis-deficient DNAPTaq genes.

FIG. 5A depicts the wild-type *Thermus flavus* polymerase gene.

FIG. 5B depicts a synthesis-deficient *Thermus flavus* polymerase gene.

FIGS. 9A–B are a set of autoradiograms of gels analyzing cleavage or lack of cleavage upon addition of different reaction components and change of incubation temperature during attempts to cleave a bifurcated duplex with DNAPTaq.

FIG. 14 is a diagram of vector pTTQ18.

FIG. 20A shows the A- and T-hairpin molecules used in the trigger/detection assay.

FIG. 20B shows the sequence of the alpha primer used in the trigger/detection assay.

FIG. 20C shows the structure of the cleaved A- and T-hairpin molecules.

FIG. 20D depicts the complementarity between the A- and T-hairpin molecules.

DESCRIPTION OF THE INVENTION

Figure 1A:
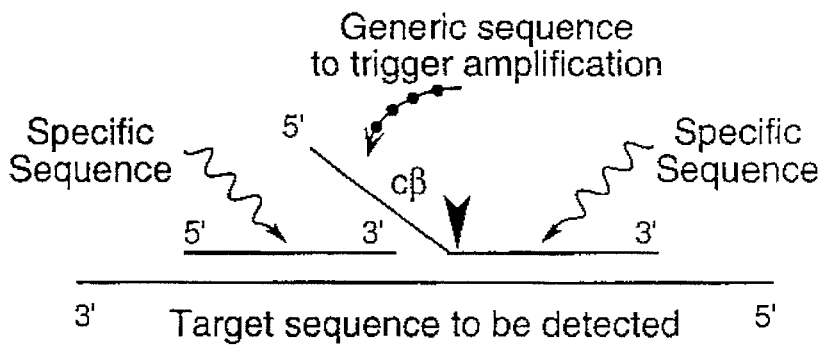
FIG. 1 is a schematic representation of the trigger/detection assay.

The present invention relates to means for cleaving a nucleic acid cleavage structure in a site-specific manner. In particular, the present invention relates to a cleaving enzyme having 5' nuclease activity without interfering nucleic acid synthetic ability.

This invention provides thermostable DNA polymerases which exhibit altered DNA synthetic activity from that of native thermostable DNA polymerases. The 5' nuclease activity of the polymerase is retained while the synthetic activity is reduced or absent. Such modified polymerases are capable of catalyzing the structure-specific cleavage of nucleic acids in the absence of interfering synthetic activity. The lack of synthetic activity during a cleavage reaction results in nucleic acid cleavage products of uniform size.

The novel properties of the polymerases of the invention form the basis of a method of detecting specific nucleic acid sequences. This method relies upon the amplification of the detection molecule rather than upon the amplification of the target sequence itself as do existing methods of detecting specific target sequences.

DNA polymerases, such as those isolated from *E. coli* or from thermophilic bacteria of the genus Thermus, DNA polymerases (DNAPs) are enzymes that synthesize new DNA strands. Several of the known DNAPs contain associated nuclease activities in addition to the synthetic activity of the enzyme.

Some DNAPs are known to remove nucleotides from the 5' and 3' ends of DNA chains Kornberg et al., DNA Replication, 2d Ed., W. H. Freeman and Co., San Francisco, (1992) These nuclease activities are usually referred to as 5' exonuclease and 3' exonuclease activities, respectively. For example, the 5' exonuclease activity located in the N-terminal domain of several DNAPs participates in the removal of RNA primers during lagging strand synthesis during DNA replication and the removal of damaged nucleotides during repair. Some DNAPs, such as the *E. coli* DNA polymerase (DNAPEcl), also have a 3' exonuclease activity responsible for proofreading during DNA synthesis (Kornberg, supra).

A DNAP isolated from *Thermus aquaticus*, termed Taq DNA polymerase (DNAPTaq), has a 5' exonuclease activity, but lacks a functional 3' exonucleolytic domain Lawyer et al., J. Biol. Chem. Sci., 12:288 (1987) Derivatives of DNAPEcl and DNAPTaq, respectively called the Klenow and Stoffel fragments, lack 5' exonuclease domains as a result of enzymatic or genetic manipulations [Brutlag et al., Biochem. Biophys. Res. Commun. 37:982 (1969); Erlich et al., Science 252:1643 (1991); Setlow and Kornberg, J. Biol. Chem. 247:232 (1972)].

The 5' exonuclease activity of DNAPTaq was reported to require concurrent synthesis [Gelfand, PCR *Technology—Principles and Applications for DNA Amplification* (H. A. Erlich, Ed.) Stockton Press, New York, p. 17 (1989)]. Although mononucleotides predominate among the digestion products of the 5' exonucleases of DNAPTaq and DNAPEcl, short oligonucleotides ($\leq 12$ nucleotides) can also be observed implying that these so-called 5' exonucleases can function endonucleolytically [Setlow, supra; Holland et al., Proc. Natl. Acad. Sci. USA 88:7276 (1991)].

In WO 92/06200, Gelfand et al. show that the preferred substrate of the 5' exonuclease activity of the thermostable DNA polymerases is displaced single-stranded DNA. Hydrolysis of the phosphodiester bond occurs between the displaced single-stranded DNA and the double-helical DNA with the preferred exonuclease cleavage site being a phosphodiester bond in the double helical region. Thus, the 5' exonuclease activity usually associated with DNAPs is a structure-dependent single-stranded endonuclease and is more properly referred to as a 5' nuclease. Exonucleases are enzymes which cleave nucleotide molecules from the ends of the nucleic acid molecule. Endonucleases, on the other hand, are enzymes which cleave the nucleic acid molecule at internal rather than terminal sites. The nuclease activity associated with some thermostable DNA polymerases cleaves endonucleolytically but this cleavage requires contact with the 5' end of the molecule being cleaved. Therefore, these nucleases are referred to as 5' nucleases.

When a 5' nuclease activity is associated with a eubacterial Type A DNA polymerase, it is found in the one-third N-terminal region of the protein as an independent functional domain. The C-terminal two-thirds of the molecule constitute the polymerization domain which is responsible for the synthesis of DNA. Some Type A DNA polymerases also have a 3' exonuclease activity associated with the two-third C-terminal region of the molecule.

The 5' exonuclease activity and the polymerization activity of DNAPs have been separated by proteolytic cleavage or genetic manipulation of the polymerase molecule. To date thermostable DNAPs have been modified to remove or reduce the amount of 5' nuclease activity while leaving the polymerase activity intact.

The Klenow or large proteolytic cleavage fragment of DNAPEcl contains the polymerase and 3' exonuclease activity but lacks the 5' nuclease activity. The Stoffel fragment of DNAPTaq DNAPStf lacks the 5' nuclease activity due to a genetic manipulation which deleted the N-terminal 289 amino acids of the polymerase molecule [Erlich et al., Science 252:1643 (1991)]. WO 92/06200 describes a thermostable DNAP with an altered level of 5' to 3' exonuclease. U.S. Pat. No. 5,108,892 describes a *Thermus aquaticus* DNAP without a 5' to 3' exonuclease. However, the art of molecular biology lacks a thermostable DNA polymerase with a lessened amount of synthetic activity.

The present invention provides modified thermostable Type A DNA polymerases that retain 5' nuclease activity but have reduced or absent synthetic activity. The ability to uncouple the synthetic activity of the enzyme from the 5' nuclease activity proves that the 5' nuclease activity does not require concurrent DNA synthesis as was previously reported (Gelfand, *PCR Technology*, supra).

The description of the invention is divided into I. Detection of Specific Nucleic Acid Sequences Using Modified Thermostable DNA Polymerases; II. Generation of Modified Thermostable DNA Polymerases; III. Therapeutic Uses of Modified Thermostable DNA Polymerases; and IV. Detection of Antigenic or Nucleic Acid Targets by a Dual Capture Assay. To facilitate understanding of the invention, a number of terms are defined below.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired coding sequence and appropriate DNA sequences necessary for the expression of the operably linked coding sequence in a particular host organism. DNA sequences necessary for expression in procaryotes include a promoter, optionally an operator sequence, a ribosome binding site and possibly other sequences. Eucaryotic cells are known to utilize promoters, polyadenlyation signals and enhancers.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phoshodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated.

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The term "cleavage structure" as used herein, refers to a nucleic acid structure which is a substrate for cleavage by the 5' nuclease activity of a DNAP.

The term "cleavage means" as used herein refers to any means which is capable of cleaving a cleavage structure in a specific manner. The cleavage means may include native DNAPs having 5' nuclease activity, and, more specifically, modified DNAPs having 5' nuclease but lacking synthetic activity.

The term "liberating" as used herein refers to the release of a nucleic acid fragment from a larger nucleic acid fragment, such as an oligonucleotide, by the action of a 5' nuclease such that the released fragment is no longer covalently attached to the remainder of the oligonucleotide.

The term "substrate strand" as used herein, means that strand of nucleic acid in a cleavage structure in which the cleavage mediated by the 5' nuclease activity occurs.

The term "template strand" as used herein, means that strand of nucleic acid in a cleavage structure which is at least partially complementary to the substrate strand and which anneals to the substrate strand to form the cleavage structure.

The term "$K_m$" as used herein refers to the Michaelis-Menten constant for an enzyme and is defined as the concentration of the specific substrate at which a given enzyme yields one-half its maximum velocity in an enzyme catalyzed reaction.

Figure 1B:
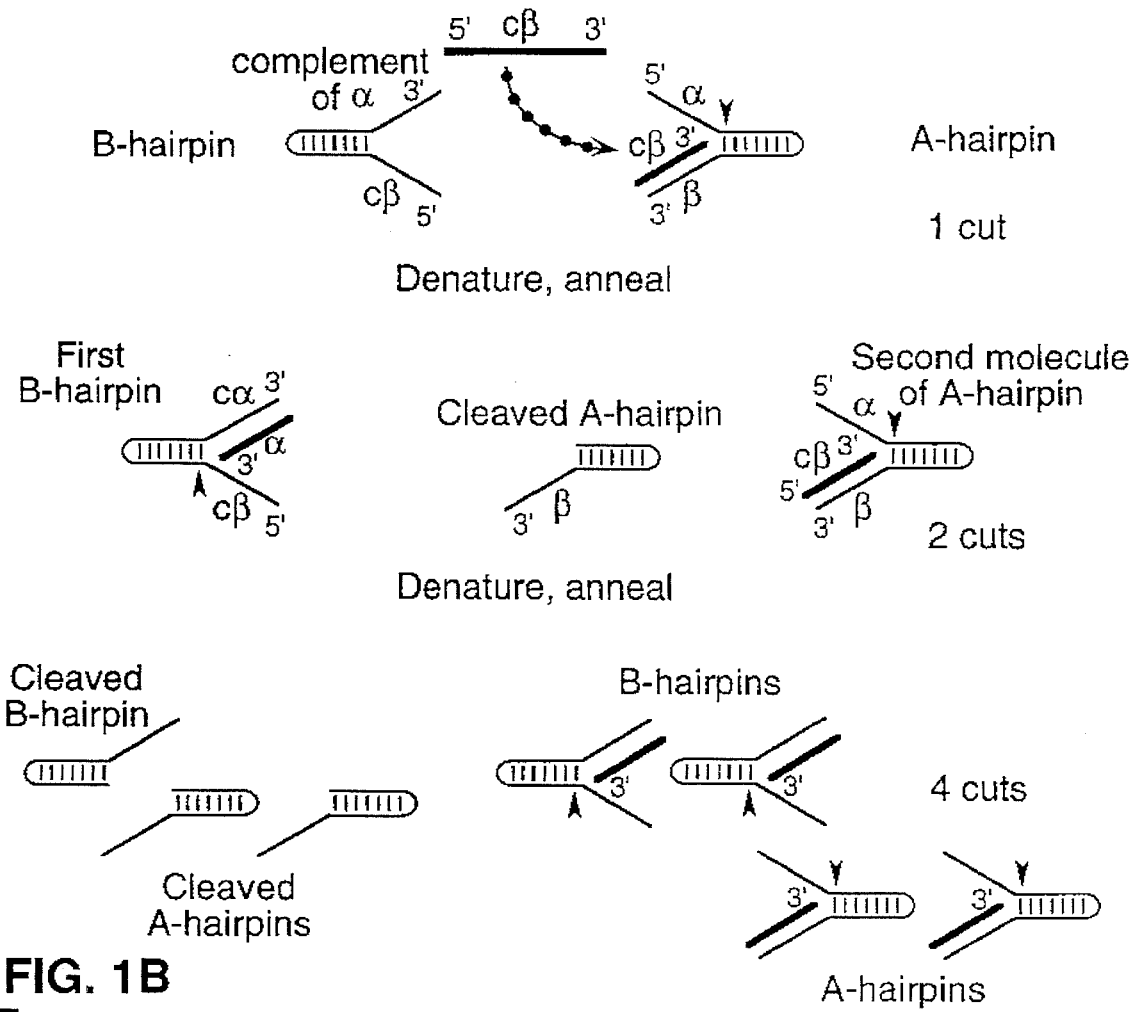

I. Detection of Specific Nucleic Acid Sequences Using Modified Thermostable DNA Polymerases The modified thermostable DNAPs of the invention form the basis of a novel detection assay for the identification of specific nucleic acid sequences. This detection system identifies the presence of specific nucleic acid sequences by requiring the annealing of two oligonucleotide probes to two portions of the target sequence. As used herein, the term "target sequence" or "target nucleic acid sequence" refers to a specific nucleic acid sequence within a polynucleotide sequence, such as genomic DNA or RNA, which is to be either detected or cleaved or both. FIG. 1 provides a schematic of the two part detection method.

In part one of the detection method, the target sequence is recognized by two distinct oligonucleotides in the triggering or trigger reaction. The first oligonucleotide is completely complementary to a portion of the target sequence. The second oligonucleotide is partially complementary to the target sequence; the 3' end of the second oligonucleotide is fully complementary to the target sequence while the 5' end is non-complementary and forms a single-stranded arm. The non-complementary end of the second oligonucleotide may be a generic sequence which can be used with a set of standard hairpin structures (described below). The detection of different target sequences would require unique portions of two oligonucleotides: the entire first oligonucleotide and the 3' end of the second oligonucleotide. The 5' arm of the second oligonucleotide can be invariant or generic in sequence.

The annealing of the first and second oligonucleotides near one another along the target sequence forms a forked cleavage structure which is a substrate for the 5' nuclease of DNA polymerases. The approximate location of the cleavage site is indicated by the large solid arrowhead in FIG. 1.

The modified polymerases of the invention are capable of cleaving this structure but are not capable of polymerizing the extension of the 3' end of the first oligonucleotide. The lack of polymerization activity is advantageous as extension of the first oligonucleotide results in displacement of the annealed region of the second oligonucleotide and results in moving the site of cleavage along the second oligonucleotide. If polymerization is allowed to occur to any significant amount, multiple lengths of cleavage product will be generated. A single cleavage product of uniform length is desirable as this cleavage product initiates the detection reaction.

The trigger reaction may be run under conditions that allow for thermocycling. Thermocycling of the reaction allows for a logarithmic increase in the amount of the trigger oligonucleotide released in the reaction.

The second part of the detection method allows the annealing of the fragment of the second oligonucleotide liberated by the cleavage of the first cleavage structure formed in the triggering reaction (called the third or trigger oligonucleotide) to a first hairpin structure. This first hairpin structure has a single-stranded 5' arm and a single-stranded 3' arm. The third oligonucleotide triggers the cleavage of this first hairpin structure by annealing to the 3' arm of the hairpin thereby forming a substrate for cleavage by the modified polymerase. The cleavage of this first hairpin structure generates two reaction products: 1) the cleaved 5' arm of the hairpin called the fourth oligonucleotide, and 2) the cleaved hairpin structure which now lacks the 5' arm and is smaller in size than the uncleaved hairpin. This cleaved first hairpin may be used as a detection molecule to indicate that cleavage directed by the trigger or third oligonucleotide occurred. Thus, this indicates that the first two oligonucleotides found and annealed to the target sequence thereby indicating the presence of the target sequence in the sample.

The detection products are amplified by having the fourth oligonucleotide anneal to a second hairpin structure. This hairpin structure has a 5' single-stranded arm and a 3' single-stranded arm. The fourth oligonucleotide generated by cleavage of the first hairpin structure anneals to the 3' arm of the second hairpin structure thereby creating a third cleavage structure recognized by the modified polymerase. The cleavage of this second hairpin structure also generates two reaction products: 1) the cleaved 5' arm of the hairpin called the fifth oligonucleotide which is similar or identical in sequence to the third nucleotide, and 2) the cleaved second hairpin structure which now lacks the 5' arm and is smaller in size than the uncleaved hairpin. This cleaved second hairpin may be as a detection molecule and amplifies the signal generated by the cleavage of the first hairpin structure. Simultaneously with the annealing of the forth oligonucleotide, the third oligonucleotide is dissociated from the cleaved first hairpin molecule so that it is free to anneal to a new copy of the first hairpin structure. The disassociation of the oligonucleotides from the hairpin structures may be accomplished by heating or other means suitable to disrupt base-pairing interactions.

Further amplification of the detection signal is achieved by annealing the fifth oligonucleotide (similar or identical in sequence to the third oligonucleotide) to another molecule of the first hairpin structure. Cleavage is then performed and the oligonucleotide that is liberated then is annealed to another molecule of the second hairpin structure. Successive rounds of annealing and cleavage of the first and second hairpin structures, provided in excess, are performed to generate a sufficient amount of cleaved hairpin products to be detected. The temperature of the detection reaction is cycled just below and just above the annealing temperature for the oligonucleotides used to direct cleavage of the hairpin structures, generally about 55° C. to 70° C. The number of cleavages will double in each cycle until the amount of hairpin structures remaining is below the $K_m$ for the hairpin structures. This point is reached when the hairpin structures are substantially used up. When the detection reaction is to be used in a quantitative manner, the cycling reactions are stopped before the accumulation of the cleaved hairpin detection products reach a plateau.

Detection of the cleaved hairpin structures may be achieved in several ways. In one embodiment detection is achieved by separation on agarose or polyacrylamide gels followed by staining with ethidium bromide. In another embodiment, detection is achieved by separation of the cleaved and uncleaved hairpin structures on a gel followed by autoradiography when the hairpin structures are first labelled with a radioactive probe and separation on chromatography columns using HPLC or FPLC followed by detection of the differently sized fragments by absorption at $OD_{260}$. Other means of detection include detection of changes in fluorescence polarization when the single-stranded 5' arm is released by cleavage, the increase in fluorescence of an intercalating fluorescent indicator as the amount of primers annealed to 3' arms of the hairpin structures increases. The formation of increasing amounts of duplex DNA (between the primer and the 3' arm of the hairpin) occurs if successive rounds of cleavage occur.

The hairpin structures may be attached to a solid support, such as an agarose, styrene or magnetic bead, via the 3' end of the hairpin. A spacer molecule may be placed between the 3' end of the hairpin and the bead, if so desired. The advantage of attaching the hairpin structures to a solid support is that this prevents the hybridization of the two hairpin structures to one another over regions which are complementary. If the hairpin structures anneal to one another, this would reduce the amount of hairpins available for hybridization to the primers released during the cleavage reactions. If the hairpin structures are attached to a solid support, then additional methods of detection of the products of the cleavage reaction may be employed. These methods include, but are not limited to, the measurement of the released single-stranded 5' arm when the 5' arm contains a label at the 5' terminus. This label may be radioactive, fluorescent, biotinylated, etc. If the hairpin structure is not cleaved, the 5' label will remain attached to the solid support. If cleavage occurs, the 5' label will be released from the solid support.

The 3' end of the hairpin molecule may be blocked through the use of dideoxynucleotides. A 3' terminus containing a dideoxynucleotide is unavailable to participate in reactions with certain DNA modifying enzymes, such as terminal transferase. Cleavage of the hairpin having a 3' terminal dideoxynucleotide generates a new, unblocked 3' terminus at the site of cleavage. This new 3' end has a free hydroxyl group which can interact with terminal transferase thus providing another means of detecting the cleavage products.

The hairpin structures are designed so that their self-complementary regions are very short (generally in the range of 3–8 base pairs). Thus, the hairpin structures are not stable at the high temperatures at which this reaction is performed (generally in the range of 50°–75° C.) unless the hairpin is stabilized by the presence of the annealed oligonucleotide on the 3' arm of the hairpin. This instability prevents the polymerase from cleaving the hairpin structure in the absence of an associated primer thereby preventing false positive results due to non-oligonucleotide directed cleavage.

As discussed above, the use of the modified polymerases of the invention which have reduced polymerization activity is advantageous in this method of detecting specific nucleic acid sequences. Significant amounts of polymerization during the cleavage reaction would cause shifting of the site of cleavage in unpredictable ways resulting in the production of a series of cleaved hairpin structures of various sizes rather than a single easily quantifiable product. Additionally, the primers used in one round of cleavage could, if elongated, become unusable for the next cycle, by either forming an incorrect structure or by being too long to melt off under moderate temperature cycling conditions. In a pristine system (i.e., lacking the presence of dNTPs), one could use the unmodified polymerase, but the presence of nucleotides (dNTPs) can decrease the per cycle efficiency enough to give a false negative result. When a crude extract (genomic DNA preparations, crude cell lysates, etc.) is employed or where a sample of DNA from a PCR reaction, or any other sample that might be contaminated with dNTPs, the modified synthesis-deficient polymerases of the present invention are particularly useful.

II. Generation of Modified Thermostable DNA Polymerases

The genes encoding Type A DNA polymerases share about 85% homology to each other on the DNA sequence level. Preferred examples of thermostable polymerases include those isolated from *Thermus aquaticus, Thermus flavus,* and *Thermus thermophilus.* However, other thermostable Type A polymerases which have 5' nuclease activity are also suitable. FIGS. 2 and 3 compare the nucleotide and amino acid sequences of the three above mentioned polymerases. In FIGS. 2 and 3, the consensus or majority sequence derived from a comparison of the nucleotide (FIG. 2) or amino acid (FIG. 3) sequence of the three thermostable DNA polymerases is shown on the top line. A dot appears in the sequences of each of these three polymerases whenever an amino acid residue in a given sequence is identical to that contained in the consensus amino acid sequence. Dashes are used in order to maximize alignment between the displayed sequences. When no consensus nucleotide or amino acid is present at a given position, an "X" is placed in the consensus sequence. SEQ ID NOS: 1–3 display the nucleotide sequences and SEQ ID NOS:4–6 display the amino acid sequences of the three wild-type polymerases. SEQ ID NO:1 corresponds to the nucleic acid sequence of the wild type *Thermus aquaticus* DNA polymerase gene isolated from the YT-1 strain [Lawyer et at., J. Biol. Chem. 264:6427 (1989)]. SEQ ID NO:2 corresponds to the nucleic acid sequence of the wild type *Thermus flavus* DNA polymerase gene [Akhmetzjanov and Vakhitov, Nucl. Acids Res. 20:5839 (1992)]. SEQ ID NO:3 corresponds to the nucleic acid sequence of the wild type *Thermus thermophilus* DNA polymerase gene [Gelfand et at., WO 91/09950 (1991)]. SEQ ID NOS:7–8 depict the consensus nucleotide and amino acid sequences, respectively for the above three DNAPs (also shown on the top row in FIGS. 2 and 3).

The modified polymerases of the invention have reduced synthetic ability, but retain substantially the same 5' exonuclease activity as the native DNA polymerase. The term "substantially the same 5' nuclease activity" as used herein means that the 5' nuclease activity of the modified enzyme retains the ability to function as a structure-dependent single-stranded endonuclease but not necessarily at the same rate of cleavage as compared to the unmodified enzyme. Type A DNA polymerases may also be modified so as to produce an enzyme which has increases 5' nuclease activity while having a reduced level of synthetic activity. Modified enzymes having reduced synthetic activity and increased 5' nuclease activity are also envisioned by the present invention.

By the term "reduced synthetic activity" as used herein it is meant that the modified enzyme has less than the level of synthetic activity found in the unmodified or "native" enzyme. The modified enzyme may have no synthetic activity remaining or may have that level of synthetic activity that will not interfere with the use of the modified enzyme in the detection assay described below. The modified polymerases of the present invention are advantageous in situations where the cleavage activity of the polymerase is desired, but the synthetic ability is not (such as in the detection assay of the invention).

As noted above, it is not intended that the invention be limited by the nature of the alteration necessary to render the polymerase synthesis deficient. The present invention contemplates a variety of methods, including but not limited to: 1) proteolysis; 2) recombinant constructs (including mutants); and 3) physical and/or chemical modification and/or inhibition.

1. Proteolysis

Thermostable DNA polymerases having a reduced level of synthetic activity are produced by physically cleaving the unmodified enzyme with proteolytic enzymes to produce fragments of the enzyme that are deficient in synthetic activity but retain 5' nuclease activity. Following proteolytic digestion, the resulting fragments are separated by standard chromatographic techniques and assayed for the ability to synthesize DNA and to act as a 5' nuclease. The assays to determine synthetic activity and 5' nuclease activity are described below.

2. Recombinant Constructs

The examples below describe a preferred method for creating a construct encoding a modified thermostable DNA polymerase. As the Type A DNA polymerases are similar in DNA sequence, the cloning strategies employed for the Thermus aquaticus and flavus polymerases are applicable to other thermostable Type A polymerases. In general, a thermostable DNA polymerase is cloned by isolating genomic DNA using molecular biological methods from a bacteria containing a thermostable Type A DNA polymerase. This genomic DNA is exposed to primers which are capable of amplifying the polymerase gene by PCR.

This amplified polymerase sequence is then subjected to standard deletion processes to delete the polymerase portion of the gene. Suitable deletion processes are described below in the examples.

The example below discusses the strategy used to determine which portions of the DNAPTaq polymerase domain could be removed without eliminating the 5' nuclease activity. Deletion of amino acids from the protein can be done either by deletion of the encoding genetic material, or by introduction of a translational stop codon by mutation or frame shift. In addition, proteolytic treatment of the protein molecule can be performed to remove segments of the protein.

In the examples below, specific alterations of the Taq gene were: a deletion between nucleotides 1601 and 2502 (the end of the coding region), a 4 nucleotide insertion at position 2043, and deletions between nucleotides 1614 and 1848 and between nucleotides 875 and 1778 (numbering is as in SEQ ID NO:1). These modified sequences are described below in the examples and at SEQ ID NOS:9–12.

Those skilled in the art understand that single base pair changes can be innocuous in terms of enzyme structure and function. Similarly, small additions and deletions can be present without substantially changing the exonuclease or polymerase function of these enzymes.

Other deletions are also suitable to create the modified polymerase of the present invention. It is preferable that the deletion decrease the polymerase activity of the modified polymerase to a level at which synthetic activity will not interfere with the use of the modified enzyme in the detection assay of the invention. Most preferably, the synthetic ability is absent. Modified polymerases are tested for the presence of synthetic and 5' nuclease activity as in assays described below.

In the example below, the PCR product of the amplified Thermus aquaticus genomic DNA did not have the identical nucleotide structure of the native genomic DNA and did not have the same synthetic ability of the original clone. Base pair changes which result due to the infidelity of DNAPTaq during PCR amplification of a polymerase gene are also a method by which the synthetic ability of a polymerase gene may be inactivated. The examples below and FIGS. 4A and 5A indicate regions in the native Thermus aquaticus and flavus DNA polymerases likely to be important for synthetic ability. There are other base pair changes and substitutions that will likely also inactivate the polymerase.

It is not necessary, however, that one start out the process of producing a modified DNA polymerase with such a mutated amplified product. This is the method by which the examples below were performed to generate the synthesis-deficient DNAPTaq mutants, but it is understood by those skilled in the art that a wild-type DNA polymerase sequence may be used as the starting material for the introduction of deletions, insertion and substitutions to produce a modified DNA polymerase having altered synthetic activity. For example, to generate the synthesis-deficient DNAPTfl mutant, the primers listed in SEQ ID NOS:13–14 were used to amplify the wild type DNA polymerase gene from Thermus flavus strain AT-62. The amplified polymerase gene was then subjected to restriction enzyme digestion to delete a large portion of the domain encoding the synthetic activity.

The present invention contemplates that the nucleic acid construct of the present invention be capable of expression in a suitable host. Those in the art know methods for attaching various promoters and 3' sequences to a gene structure to achieve efficient expression. The examples below disclose two suitable vectors and six suitable vector constructs. Of course, there are other promoter/vector combinations that would be suitable. It is not necessary that a host organism be used for the expression of the nucleic acid constructs of the invention. For example, expression of the protein encoded by a nucleic acid construct may be achieved through the use of a cell-free in vitro transcription/translation system. An example of such a cell-free system is the commercially available TnT™ Coupled Reticulocyte Lysate System (Promega Corporation, Madison, Wis.).

Once a suitable nucleic acid construct has been made, the modified polymerase may be produced from the construct. The examples below and standard molecular biological teachings enable one to manipulate the construct by different suitable methods.

Once the modified polymerase has been expressed, the polymerase is tested for both synthetic and nuclease activity as described below.

3. Physical and/or Chemical Modification and/or Inhibition

The synthetic activity of a thermostable DNA polymerase may be reduced by chemical and/or physical means. In one embodiment, the cleavage reaction catalyzed by the 5' nuclease activity of the polymerase is run under conditions which preferentially inhibit the synthetic activity of the polymerase. The level of synthetic activity need only be reduced to that level of activity which does not interfere with cleavage reactions requiring no significant synthetic activity.

As shown in the examples below, concentrations of $Mg^{++}$ greater than 5 mM inhibit the polymerization activity of the native DNAPTaq. The ability of the 5' nuclease to function under conditions where synthetic activity is inhibited is tested by running the assays for synthetic and 5' nuclease activity, described below, in the presence of a range of $Mg^{++}$ concentrations (5 to 10 mM). The effect of a given concentration of $Mg^{++}$ is determined by quantitation of the amount of synthesis and cleavage in the test reaction as compared to the standard reaction for each assay.

The inhibitory effect of other ions, polyamines, denaturants, such as urea, formamide, dimethylsulfoxide, glycerol and non-ionic detergents (Triton X-100 and Tween-20), nucleic acid binding chemicals such as, actinomycin D, ethidium bromide and psoralens, are tested by their addition to the standard reaction buffers for the synthesis and 5' nuclease assays. Those compounds having a preferential inhibitory effect on the synthetic activity of a thermostable polymerase are then used to create reaction conditions under which 5' nuclease activity (cleavage) is retained while synthetic activity is reduced or eliminated.

Physical means may be used to preferentially inhibit the synthetic activity of a polymerase. For example, the synthetic activity of thermostable polymerases is destroyed by exposure of the polymerase to extreme heat (typically 96° to 100° C.) for extended periods of time (greater than or equal to 20 minutes). While these are minor differences with respect to the specific heat tolerance for each of the enzymes, these are readily determined. Polymerases are treated with heat for various periods of time and the effect of the heat treatment upon the synthetic and 5' nuclease activities is determined.

III. Therapeutic Utility of Modified DNA Polymerases

The modified DNA polymerases of the invention have not only the diagnostic utility discussed above, but additionally have therapeutic utility for the cleavage and inactivation of specific mRNAs inside infected cells. The mRNAs of pathogenic agents, such as viruses, bacteria, are targeted for cleavage by a synthesis-deficient DNA polymerase by the introduction of a oligonucleotide complementary to a given mRNA produced by the pathogenic agent into the infected cell along with the synthesis-deficient polymerase. Any pathogenic agent may be targeted by this method provided the nucleotide sequence information is available so that an appropriate oligonucleotide may be synthesized. The synthetic oligonucleotide anneals to the complementary mRNA thereby forming a cleavage structure recognized by the modified enzyme. The ability of the 5' nuclease activity of thermostable DNA polymerases to cleave RNA-DNA hybrids is shown herein in Example 1D.

Liposomes provide a convenient delivery system. The synthetic oligonucleotide may be conjugated or bound to the nuclease to allow for co-delivery of these molecules. Additional delivery systems may be employed.

Inactivation of pathogenic mRNAs has been described using antisense gene regulation and using ribozymes (Rossi, U.S. Pat. No. 5,144,019, hereby incorporated by reference). Both of these methodologies have limitations.

The use of antisense RNA to impair gene expression requires stoichiometric and therefore, large molar excesses of anti-sense RNA relative to the pathogenic RNA to be effective. Ribozyme therapy, on the other hand, is catalytic and therefore lacks the problem of the need for a large molar excess of the therapeutic compound found with antisense methods. However, ribozyme cleavage of a given RNA requires the presence of highly conserved sequences to form the catalytically active cleavage structure. This requires that the target pathogenic mRNA contain the conserved sequences (GAAAC $(X)_n$ GU) thereby limiting the number of pathogenic mRNAs that can be cleaved by this method. In contrast, the catalytic cleavage of RNA by the use of a DNA oligonucleotide and a modified DNA polymerase is dependent upon structure only; thus, virtually any pathogenic RNA sequence can be used to design an appropriate cleavage structure.

IV. Detection of Antigenic or Nucleic Acid Targets by a Dual Capture Assay

The ability to generate synthesis-deficient thermostable DNA polymerases provides the basis for a novel means of detecting the presence of antigenic or nucleic acid targets. In this dual capture assay, the polymerase domains encoding the synthetic activity and the nuclease activity are covalently attached to two separate and distinct antibodies or oligonucleotides. When both the synthetic and the nuclease domains are present in the same reaction and dATP, dTTP and a small amount of poly d(A-T) are provided, an enormous amount of poly d(A-T) is produced. The large amounts of poly d(A-T) are produced as a result of the ability of the 5' nuclease to cleave newly made poly d(A-T) to generate primers that are, in turn, used by the synthetic domain to catalyze the production of even more poly d(A-T). The 5' nuclease is able to cleave poly d(A-T) because poly d(A-T) is self-complementary and easily forms alternate structures at elevated temperatures. These structures are recognized by the 5' nuclease and are then cleaved to generate more primer for the synthesis reaction.

The following is an example of the dual capture assay to detect an antigen(s): A sample to be analyzed for a given antigen(s) is provided. This sample may comprise a mixture of cells; for example, cells infected with viruses display virally-encoded antigens on their surface. If the antigen(s) to be detected are present in solution, they are first attached to a solid support such as the wall of a microtiter dish or to a bead using conventional methodologies. The sample is then mixed with 1) the synthetic domain of a thermostable DNA polymerase conjugated to an antibody which recognizes either a first antigen or a first epitope on an antigen, and 2) the 5' nuclease domain of a thermostable DNA polymerase conjugated to a second antibody which recognizes either a second, distinct antigen or a second epitope on the same antigen as recognized by the antibody conjugated to the synthetic domain. Following an appropriate period to allow the interaction of the antibodies with their cognate antigens (conditions will vary depending upon the antibodies used; appropriate conditions are well known in the art), the sample is then washed to remove unbound antibody-enzyme domain complexes. dATP, dTTP and a small amount of poly d(A-T) is then added to the washed sample and the sample is incubated at elevated temperatures (generally in the range of 60°–80° C. and more preferably, 70°–75° C.) to permit the thermostable synthetic and 5' nuclease domains to function. If the sample contains the antigen(s) recognized by both separately conjugated domains of the polymerase, then an exponential increase in poly d(A-T) production occurs. If only the antibody conjugated to the synthetic domain of the polymerase is present in the sample such that no 5' nuclease domain is present in the washed sample, then only an arithmetic increase in poly d(A-T) is possible. The reaction conditions may be controlled in such a way so that an arithmetic increase in poly d(A-T) is below the threshold of detection. This may be accomplished by controlling the length of time the reaction is allowed to proceed or by adding so little poly d(A-T) to act as template that in the absence of nuclease activity to generate new poly d(A-T) primers very little poly d(A-T) is synthesized.

It is not necessary for both domains of the enzyme to be conjugated to an antibody. One can provide the synthetic domain conjugated to an antibody and provide the 5' nuclease domain in solution or vice versa. In such a case the conjugated antibody-enzyme domain is added to the sample, incubated, then washed. dATP, dTTP, poly d(A-T) and the remaining enzyme domain in solution is then added.

Additionally, the two enzyme domains may be conjugated to oligonucleotides such that target nucleic acid sequences can be detected. The oligonucleotides conjugated to the two different enzyme domains may recognize different regions on the same target nucleic acid strand or may recognize two unrelated target nucleic acids.

The production of poly d(A-T) may be detected in many ways including: 1) use of a radioactive label on either the dATP or dTTP supplied for the synthesis of the poly d(A-T), followed by size separation of the reaction products and autoradiography; 2) use of a fluorescent probe on the dATP and a biotinylated probe on the dTTP supplied for the synthesis of the poly d(A-T), followed by passage of the reaction products over an avidin bead, such as magnetic beads conjugated to avidin; the presence of the florescent probe on the avidin-containing bead indicates that poly d(A-T) has been formed as the fluorescent probe will stick to the avidin bead only if the fluorescenated dATP is incorporated into a covalent linkage with the biotinylated dTTP; and 3) changes fluorescence polarization indicating an increase in size. Other means of detecting the presence of poly d(A-T) include the use of intercalating fluorescence indicators to monitor the increase in duplex DNA formation.

The advantages of the above dual capture assay for detecting antigenic or nucleic acid targets include:

1) No thermocycling of the sample is required. The polymerase domains and the dATP and dTTP are incubated at a fixed temperature (generally about 70° C.). After 30 minutes of incubation up to 75% of the added dNTPs are incorporated into poly d(A-T). The lack of thermocycling makes this assay well suited to clinical laboratory settings; there is no need to purchase a thermocycling apparatus and there is no need to maintain very precise temperature control.

2) The reaction conditions are simple. The incubation of the bound enzymatic domains is done in a buffer containing 0.5 mM $MgCl_2$ (higher concentrations may be used), 2–10 mM Tris-Cl, pH 8.5, approximately 50 μM dATP and dTTP. The reaction volume is 10–20 μl and reaction products are detectable within 10–20 minutes.

3) No reaction is detected unless both the synthetic and nuclease activities are present. Thus, a positive result indicates that both probes (antibody or oligonucleotide) have recognized their targets thereby increasing the specificity of recognition by having two different probes bind to the target.

The ability to separate the two enzymatic activities of the DNAP allows for exponential increases in poly d(A-T) production. If the Klenow fragment of DNAPEcl (which lacks 5' nuclease activity) is used, only a linear or arithmetic increase in poly d(A-T) production is possible [Setlow et al., J. Biol. Chem. 247:224 (1972)]. The ability to provide an enzyme having 5' nuclease activity but lacking synthetic activity is made possible by the disclosure of this invention.

EXAMPLE 1

Characteristics of Native Thermostable DNA Polymerases

A. 5' Nuclease Activity of DNAPTaq

Figure 6:
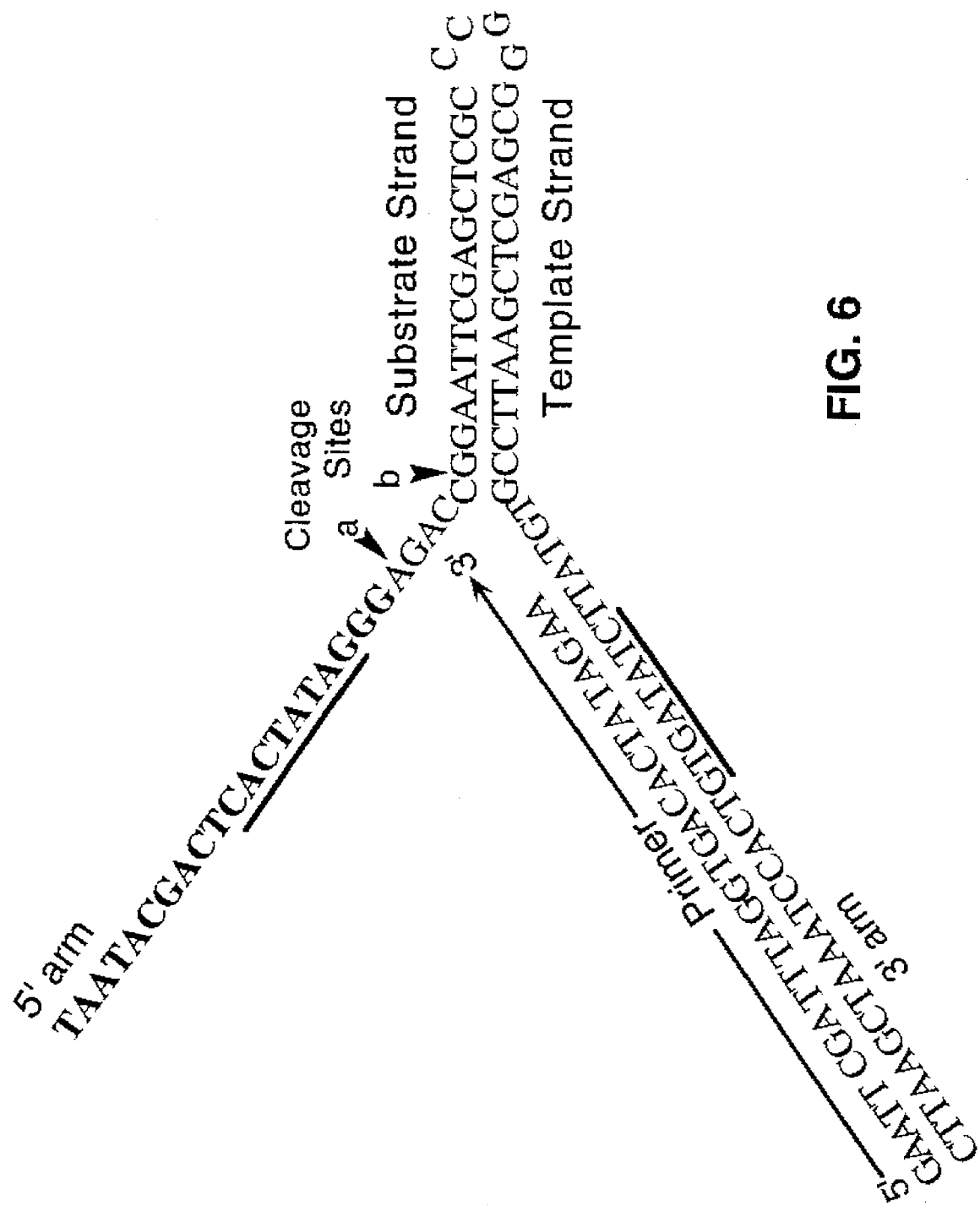
FIG. 6 depicts a structure which cannot be amplified using DNAPTaq.

During the polymerase chain reaction (PCR) [Saiki et al., Science 239:487 (1988); Mullis and Faloona, *Methods in Enzymology* 155:335 (1987)], DNAPTaq is able to amplify many, but not all, DNA sequences. One sequence that cannot be amplified using DNAPTaq is shown in FIG. 6 (Hairpin structure is SEQ ID NO:15, PRIMERS are SEQ ID NOS:16–17.) This DNA sequence has the distinguishing characteristic of being able to fold on itself to form a hairpin with two single-stranded arms, which correspond to the primers used in PCR.

To test whether this failure to amplify is due to the 5' nuclease activity of the enzyme, we compared the abilities of DNAPTaq and DNAPStf to amplify this DNA sequence during 30 cycles of PCR. Synthetic oligonucleotides were obtained from The Biotechnology Center at the University of Wisconsin-Madison. The DNAPTaq and DNAPStf were from Perkin Elmer. The substrate DNA comprised the hairpin structure shown in FIG. 6 cloned in a double-stranded form into pUC19. The primers used in the amplification are listed as SEQ ID NOS:16–17. Primer SEQ ID NO: 17 is shown annealed to the 3' arm of the hairpin structure in FIG. 6. Primer SEQ ID NO: 16 is shown as the first 20 nucleotides in bold on the 5' arm of the hairpin in FIG. 6.

Polymerase chain reactions comprised 1 ng of supercoiled plasmid target DNA, 5 pmoles of each primer, 40 μM each dNTP, and 2.5 units of DNAPTaq or DNAPStf, in a 50 μl solution of 10 mM Tris. Cl pH 8.3. The DNAPTaq reactions included 50 mM KCl and 1.5 mM $MgCl_2$. The temperature profile was 95° C. for 30 sec., 55° C. for 1 min. and 72° C. for 1 min., through 30 cycles. Ten percent of each reaction was analyzed by gel electrophoresis through 6% polyacrylamide (cross-linked 29:1) in a buffer of 45 mM Tris.Borate, pH 8.3, 1.4 mM EDTA.

Figure 7:
FIG. 7 is a ethidium bromide-stained gel demonstrating attempts to amplify a bifurcated duplex using either DNAPTaq or DNAPStf (Stoffel).

The results are shown in FIG. 7. The expected product was made by DNAPStf but not by DNAPTaq. We conclude that the 5' nuclease activity of DNAPTaq is responsible for the lack of amplification of this DNA sequence.

Figure 8:
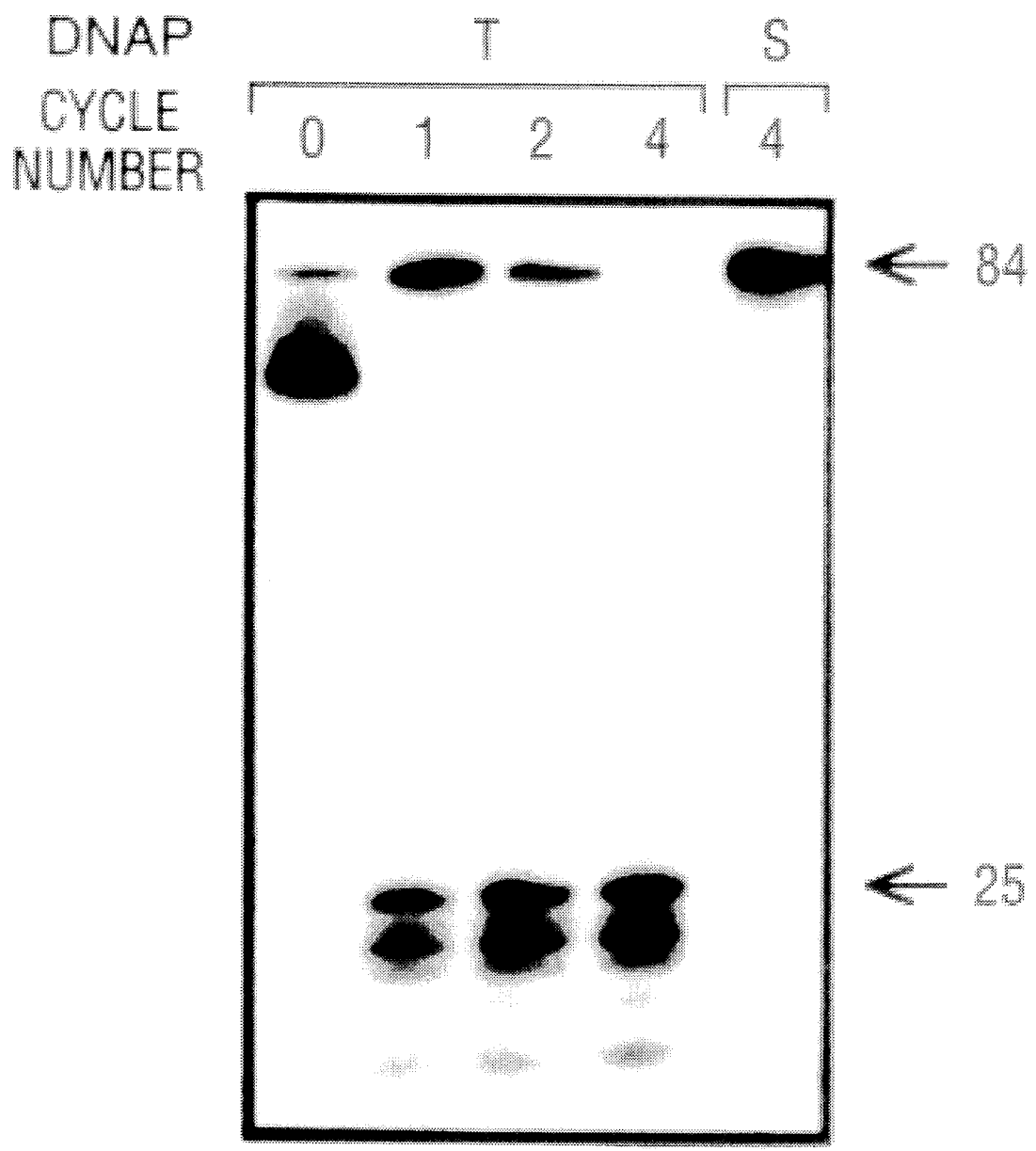
FIG. 8 is an autoradiogram of a gel analyzing the cleavage of a bifurcated duplex by DNAPTaq and lack of cleavage by DNAPStf.

To test whether the 5' unpaired nucleotides in the substrate region of this structured DNA are removed by DNAPTaq, the fate of the end-labeled 5' arm during four cycles of PCR was compared using the same two polymerases (FIG. 8). The hairpin templates, such as the one described in FIG. 6, were made using DNAPStf and a $^{32}P$-5'-end-labeled primer. The 5'-end of the DNA was released as a few large fragments by DNAPTaq but not by DNAPStf. The sizes of these fragments (based on their mobilities) show that they contain most or all of the unpaired 5' arm of the DNA. Thus, cleavage occurs at or near the base of the bifurcated duplex. These released fragments terminate with 3' OH groups, as evidenced by direct sequence analysis, and the abilities of the fragments to be extended by terminal deoxynucleotidyl transferase.

FIGS. 9–11 show the results of experiments designed to characterize the cleavage reaction catalyzed by DNAPTaq. Unless otherwise specified, the cleavage reactions comprised 0.01 pmoles of heat-denatured, end-labeled hairpin DNA (with the unlabeled complementary strand also present), 1 pmole primer (complementary to the 3' arm) and 0.5 units of DNAPTaq (estimated to be 0.026 pmoles) in a total volume of 10 μl of 10 mM Tris-Cl, ph 8.5, 50 mM KCl and 1.5 mM $MgCl_2$. As indicated, some reactions had different concentrations of KCl, and the precise times and temperatures used in each experiment are indicated in the individual figures and legends. The reactions that included a primer used the one shown in FIG. 6 (SEQ ID NO:17). In some instances, the primer was extended to the junction site through the use of polymerase and the appropriate nucleotides.

Reactions were initiated at the final reaction temperature by the addition of either the $MgCl_2$ or enzyme. Reactions were stopped at their incubation temperatures by the addition of 8 μl of 95% formamide with 20 mM EDTA and 0.05% marker dyes. The $T_m$ calculations listed were made using the Oligo™ primer analysis software from National Biosciences, Inc., Plymouth, Minn. These were determined using 0.25 μM as the DNA concentration, at either 15 or 65 mM total salt (the 1.5 mM MgCl$_2$ in all reactions was given the value of 15 mM salt for these calculations).

FIG. 9 is an autoradiogram containing the results of a set of experiments and conditions on the cleavage site. FIG. 9A is a determination of reaction components required for cleavage. Incubation of 5'-end-labeled hairpin DNA was for 30 minutes at 55° C., with the indicated components. The products were resolved by denaturing polyacrylamide gel electrophoresis and the lengths of the products, in nucleotides, are indicated. FIG. 9B describes the effect of temperature on the site of cleavage in the absence of added primer. Reactions were incubated in the absence of KCl for 10 minutes at the indicated temperatures. The lengths of the products, in nucleotides, are indicated.

Surprisingly, cleavage by DNAPTaq requires neither a primer nor dNTPs (see FIG. 9A). Thus, the 5' nuclease activity can be uncoupled from polymerization. Nuclease activity requires magnesium ions, though manganese ions can be substituted without loss of activity. Neither zinc nor calcium ions support the cleavage reaction. The reaction occurs over a broad temperature range, from 25° C. to 85° C., with the rate of cleavage increasing at higher temperatures.

Still referring to FIG. 9, the primer is not elongated in the absence of added dNTPs. However, the primer influences both the site and the rate of cleavage of the hairpin. The change in the site of cleavage (FIG. 9A) apparently results from disruption of a short duplex formed between the arms of the DNA substrate. In the absence of primer, the sequences indicated by underlining in FIG. 6 could pair, forming an extended duplex. Cleavage at the end of the extended duplex would release the 11 nucleotide fragment seen on the FIG. 9A lanes with no added primer. Addition of excess primer (FIG. 9A, lanes 3 and 4) or incubation at an elevated temperature (FIG. 9B) disrupts the short extension of the duplex and results in a longer 5' arm and, hence, longer cleavage products.

The location of the 3' end of the primer can influence the precise site of cleavage. Electrophoretic analysis revealed that in the absence of primer (FIG. 9B), cleavage occurs at the end of the substrate duplex (either the extended or shortened form, depending on the temperature) between the first and second base pairs. When the primer extends up to the base of the duplex, cleavage also occurs one nucleotide into the duplex. However, when a gap of four or six nucleotides exists between the 3' end of the primer and the substrate duplex, the cleavage site is shifted four to six nucleotides in the 5' direction.

Figures 10A, 10B:
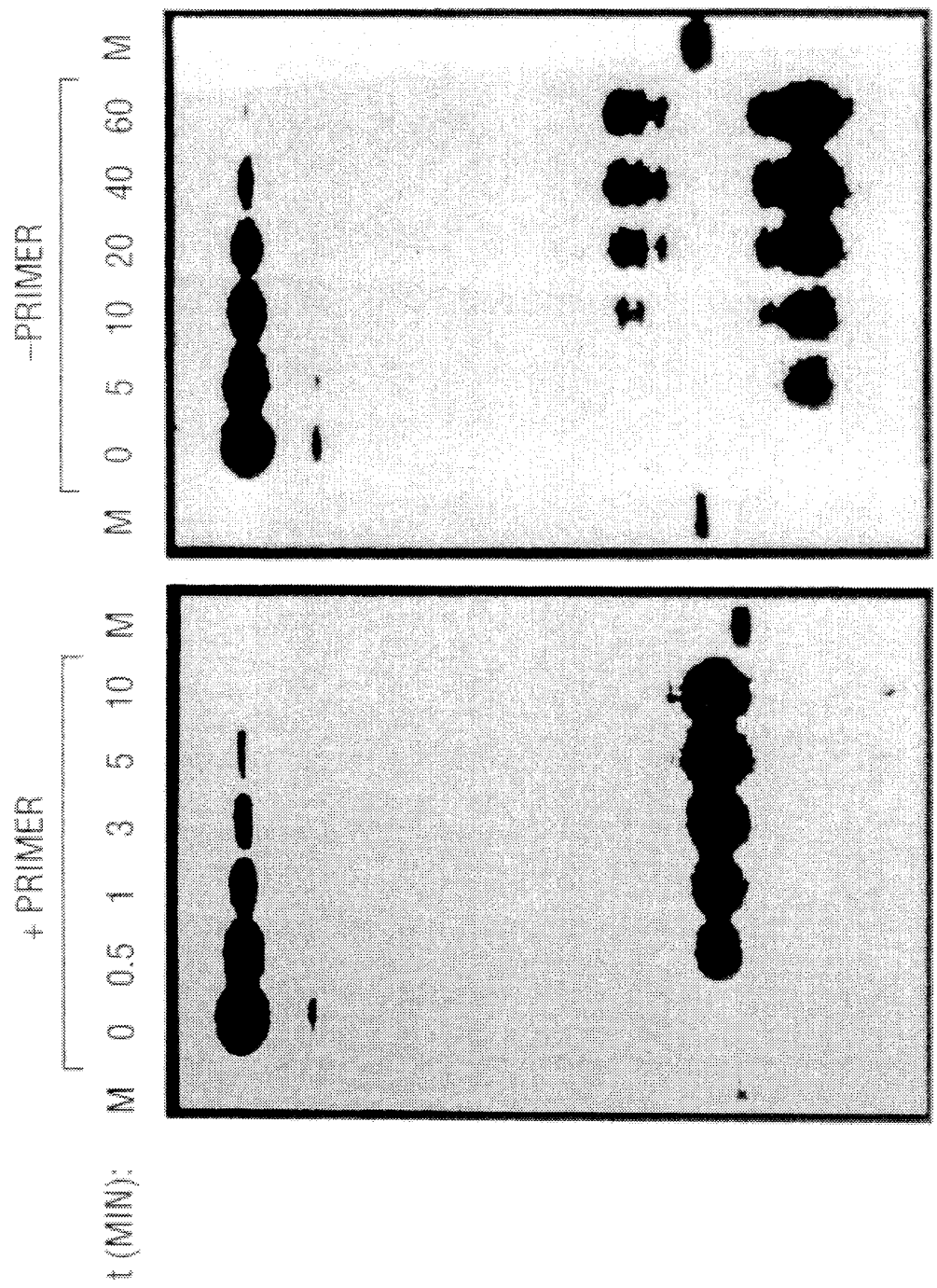
FIGS. 10A–B are an autoradiogram displaying timed cleavage reactions, with and without primer.

FIG. 10 describes the kinetics of cleavage in the presence (FIG. 10A) or absence (FIG. 10B) of a primer oligonucleotide. The reactions were run at 55° C. with either 50 mM KCl (FIG. 10A) or 20 mM KCl (FIG. 10B). The reaction products were resolved by denaturing polyacrylamide gel electrophoresis and the lengths of the products, in nucleotides, are indicated. "M", indicating a marker, is a 5' end-labeled 19-nt oligonucleotide. Under these salt conditions, FIGS. 10A and 10B indicate that the reaction appears to be about twenty times faster in the presence of primer than in the absence of primer. This effect on the efficiency may be attributable to proper alignment and stabilization of the enzyme on the substrate.

The relative influence of primer on cleavage rates becomes much greater when both reactions are run in 50 mM KCl. In the presence of primer, the rate of cleavage increases with KCl concentration, up to about 50 mM. However, inhibition of this reaction in the presence of primer is apparent at 100 mM and is complete at 150 mM KCl. In contrast, in the absence of primer the rate is enhanced by concentration of KCl up to 20 mM, but it is reduced at concentrations above 30 mM. At 50 mM KCl, the reaction is almost completely inhibited. The inhibition of cleavage by KCl in the absence of primer is affected by temperature, being more pronounced at lower temperatures.

Recognition of the 5' end of the arm to be cut appears to be an important feature of substrate recognition. Substrates that lack a free 5' end, such as circular M13 DNA, cannot be cleaved under any conditions tested. Even with substrates having defined 5' arms, the rate of cleavage by DNAPTaq is influenced by the length of the arm. In the presence of primer and 50 mM KCl, cleavage of a 5' extension that is 27 nucleotides long is essentially complete within 2 minutes at 55° C. In contrast, cleavages of molecules with 5' arms of 84 and 188 nucleotides are only about 90% and 40% complete after 20 minutes. Incubation at higher temperatures reduces the inhibitory effects of long extensions indicating that secondary structure in the 5' arm or a heat-labile structure in the enzyme may inhibit the reaction. A mixing experiment, run under conditions of substrate excess, shows that the molecules with long arms do not preferentially tie up the available enzyme in non-productive complexes. These results may indicate that the 5' nuclease domain gains access to the cleavage site at the end of the bifurcated duplex by moving down the 5' arm from one end to the other. Longer 5' arms would be expected to have more adventitious secondary structures (particularly when KCl concentrations are high), which would be likely to impede this movement.

Cleavage does not appear to be inhibited by long 3' arms of either the substrate strand target molecule or pilot nucleic acid, at least up to 2 kilobases. At the other extreme, 3' arms of the pilot nucleic acid as short as one nucleotide can support cleavage in a primer-independent reaction, albeit inefficiently. Fully paired oligonucleotides do not elicit cleavage of DNA templates during primer extension.

The ability of DNAPTaq to cleave molecules even when the complementary strand contains only one unpaired 3' nucleotide may be useful in optimizing allele-specific PCR. PCR primers that have unpaired 3' ends could act as pilot oligonucleotides to direct selective cleavage of unwanted templates during preincubation of potential template-primer complexes with DNAPTaq in the absence of nucleoside triphosphates.

B. 5' Nuclease Activities of Other DNAPs

To determine whether other 5' nucleases in other DNAPs would be suitable for the present invention, an array of enzymes, several of which were reported in the literature to be free of apparent 5' nuclease activity, were examined. The ability of these other enzymes to cleave nucleic acids in a structure-specific manner was tested using the hairpin substrate shown in FIG. 6 under conditions reported to be optimal for synthesis by each enzyme.

DNAPEcl and DNAP Klenow were obtained from Promega Corporation; the DNAP of *Pyrococcus furious* [DNAPPfu, Bargseid et al., Strategies (Strategene, La Jolla, Calif.) 4:34 (1991)] was from Strategene; the DNAP of *Thermococcus litoralis* DNAPTli, Vent™(exo-), Perler et al., Proc. Natl. Acad. Sci. USA 89:5577 (1992)] was from New England Biolabs; the DNAP of *Thermus flavus* [DNAPTfl, Kaledin et al., Biokhimiya 46:1576 (1981)] was from Epicentre Technologies; and the DNAP of *Thermus thermophilus* [DNAPTth, Carballeira et al., Biotechniques 9:276 (1990); Myers et al., Biochem. 30:7661 (1991)] was from U.S. Biochemicals.

0.5 units of each DNA polymerase was assayed in a 20 µl reaction, using either the buffers supplied by the manufacturers for the primer-dependent reactions, or 10 mM Tris.Cl, pH 8.5, 1.5 mM $MgCl_2$, and 20 mM KCl. Reaction mixtures were at held 72° C. before the addition of enzyme.

Figures 11A, 11B:
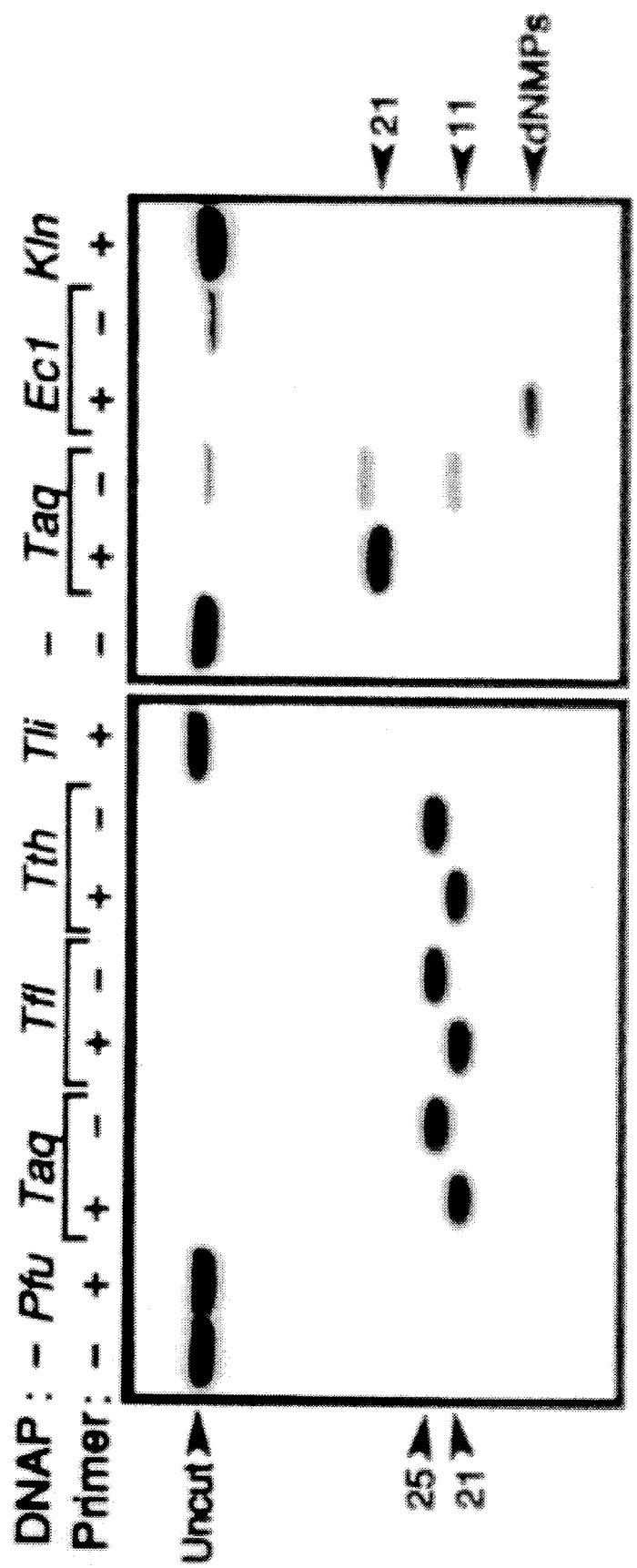
FIG. 11A–B are a set of autoradiograms of gels demonstrating attempts to cleave a bifurcated duplex (with and without primer) with various DNAPs.

FIG. 11 is an autoradiogram recording the results of these tests. FIG. 11A demonstrates reactions of endonucleases of DNAPs of several thermophilic bacteria. The reactions were incubated at 55° C. for 10 minutes in the presence of primer or at 72° C. for 30 minutes in the absence of primer, and the products were resolved by denaturing polyacrylamide gel electrophoresis. The lengths of the products, in nucleotides, are indicated. FIG. 11B demonstrates endonucleolytic cleavage by the 5' nuclease of DNAPEcl. The DNAPEcl and DNAP Klenow reactions were incubated for 5 minutes at 37° C. Note the light band of cleavage products of 25 and 11 nucleotides in the DNAPEcl lanes (made in the presence and absence of primer, respectively). FIG. 7B also demonstrates DNAPTaq reactions in the presence (+) or absence (−) of primer. These reactions were run in 50 mM and 20 mM KCl, respectively, and were incubated at 55° C. for 10 minutes.

Referring to FIG. 11A, DNAPs from the eubacteria *Thermus thermophilus* and *Thermus flavus* cleave the substrate at the same place as DNAPTaq, both in the presence and absence of primer. In contrast, DNAPs from the archaebacteria *Pyrococcus furiosus* and *Thermococcus litoralis* are unable to cleave the substrates endonucleolytically. The DNAPs from *Pyrococcus furious* and *Thermococcus litoralis* share little sequence homology with eubacterial enzymes (Ito et al., Nucl. Acids Res. 19:4045 (1991); Mathur et al., Nucl. Acids. Res. 19:6952 (1991); see also Perier et al.). Referring to FIG. 11B, DNAPEcl also cleaves the substrate, but the resulting cleavage products are difficult to detect unless the 3' exonuclease is inhibited. The amino acid sequences of the 5' nuclease domains of DNAPEcl and DNAPTaq are about 38% homologous (Gelfand, supra).

The 5' nuclease domain of DNAPTaq also shares about 19% homology with the 5' exonuclease encoded by gene 6 of bacteriophage T7 [Dunn et al., J. Mol. Biol., 166:477 (1983)]. This nuclease, which is not covalently attached to a DNAP polymerization domain, is also able to cleave DNA endonucleolytically, at a site similar or identical to the site that is cut by the 5' nucleases described above, in the absence of added primers. The nature of this 5' exonuclease precludes testing in the presence of a primer; a primer duplexed to the 3' arm would be a substrate for this activity.

C. Transcleavage

Figure 12A:
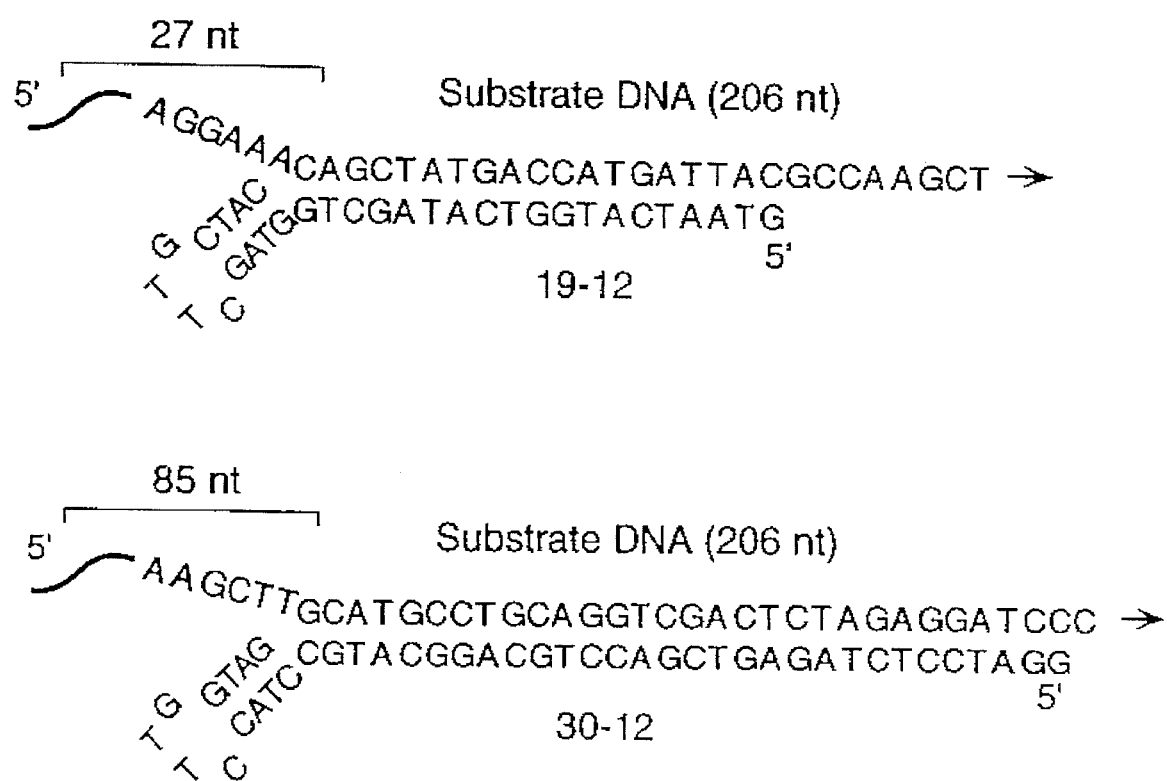
FIG. 12A shows the substrates and oligonucleotides used to test the specific cleavage of substrate DNAs targeted by pilot oligonucleotides.

The ability of a 5' nuclease to be directed to cleave efficiently at any specific sequence was demonstrated in the following experiment. A partially complementary oligonucleotide termed a "pilot oligonucleotide" was hybridized to sequences at the desired point of cleavage. The non-complementary part of the pilot oligonucleotide provided a structure analogous to the 3' arm of the template (see FIG. 6), whereas the 5' region of the substrate strand became the 5' arm. A primer was provided by designing the 3' region of the pilot so that it would fold on itself creating a short hairpin with a stabilizing tetra-loop [Antao et al., Nucl. Acids Res. 19:5901 (1991)]. Two pilot oligonucleotides are shown in FIG. 12A. Oligonucleotides 19–12 (SEQ ID NO:18) and 30–19 (SEQ ID NO:19) have 19 or 30 nucleotides, respectively, that are complementary to different sequences in the substrate strand. The pilot oligonucleotides are calculated to melt off their complements at about 50° C. (19–12) and about 75° C. (30–12). Both pilots have 12 nucleotides at their 3' ends, which act as 3' arms with base-paired primers attached.

To demonstrate that cleavage could be directed by a pilot oligonucleotide, we incubated a single-stranded target DNA with DNAPTaq in the presence of two potential pilot oligonucleotides. The transcleavage reactions, where the target and pilot nucleic acids are not covalently linked, includes 0.01 pmoles of single end-labeled substrate DNA, 1 unit of DNAPTaq and 5 pmoles of pilot oligonucleotide in a volume of 20 µl of the same buffers. These components were combined during a one minute incubation at 95° C., to denature the PCR-generated double-stranded substrate DNA, and the temperatures of the reactions were then reduced to their final incubation temperatures. Oligonucleotides 30–12 and 19–12 can hybridize to regions of the substrate DNAs that are 85 and 27 nucleotides from the 5' end of the targeted strand.

Figure 12B:
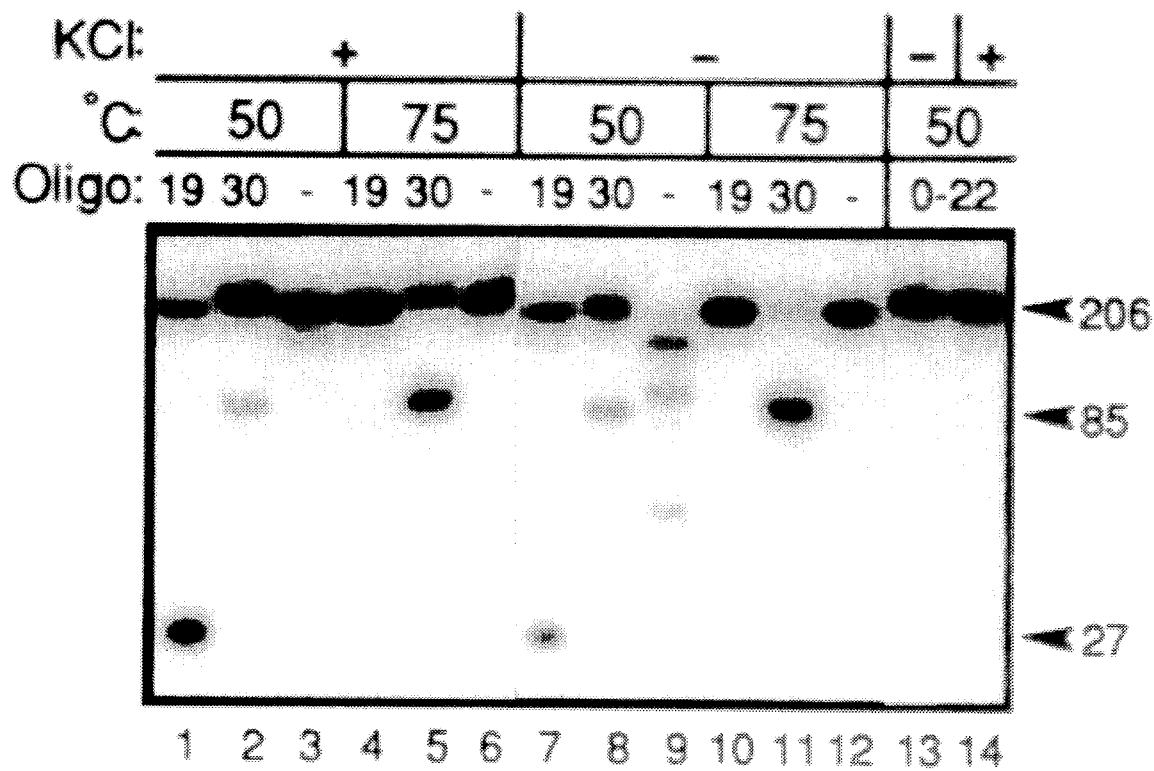
FIG. 12B shows an autoradiogram of a gel showing the results of cleavage reactions using the substrates and oilgonucleotides shown FIG. 12A.

Cleavage of the substrate DNA occurred in the presence of the pilot oligonucleotide 19–12 at 50° C. (FIG. 12B, lanes 1 and 7) but not at 75° C. (lanes 4 and 10). In the presence of oligonucleotide 30–12 cleavage was observed at both temperatures. Cleavage did not occur in the absence of added oligonucleotides (lanes 3, 6 and 12) or at about 80° C. even though at 50° C. adventitious structures in the substrate allowed primer-independent cleavage in the absence of KCl (FIG. 12B, lane 9). A non-specific oligonucleotide with no complementarity to the substrate DNA did not direct cleavage at 50° C., either in the absence or presence of 50 mM KCl (lanes 13 and 14). Thus, the specificity of the cleavage reactions can be controlled by the extent of complementarity to the substrate and by the conditions of incubation.

D. Cleavage of RNA

Figure 13A:
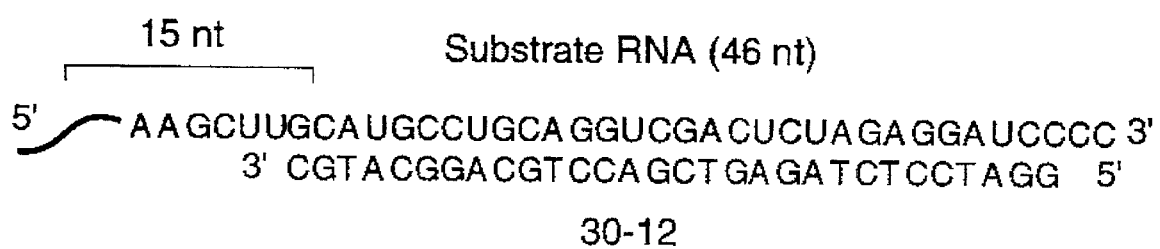
FIG. 13A shows the substrate and oligonucleotide used to test the specific cleavage of a substrate RNA targeted by a pilot oligonucleotide.

An RNA version of the sequence used in the transcleavage experiments discussed above was tested for its ability to serve as a substrate in the reaction. The RNA is cleaved at the expected place, in a reaction that is dependent upon the presence of the pilot oligonucleotide. The RNA substrate, made by T7 RNA polymerase in the presence of [$\alpha$-$^{32}$P] UTP, corresponds to a truncated version of the DNA substrate used in FIG. 12B. Reaction conditions were similar to those in used for the DNA substrates described above, with 50 mM KCl; incubation was for 40 minutes at 55° C. The pilot oligonucleotide used is termed 30–0 (SEQ ID NO:20) and is shown in FIG. 13A.

Figure 13B:
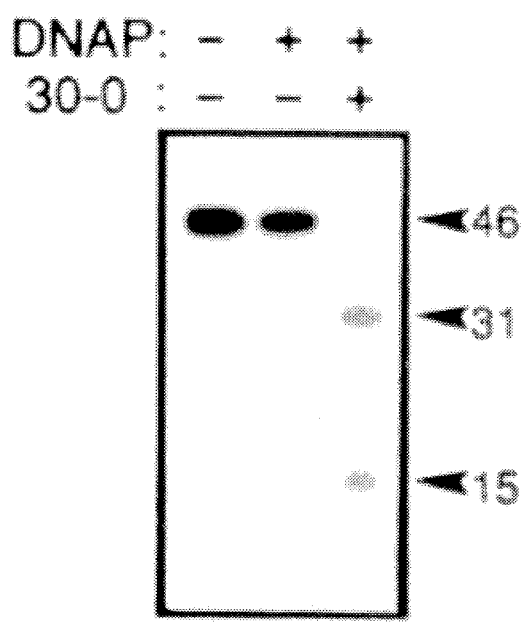
FIG. 13B shows an autoradiogram of a gel showing the results of a cleavage reaction using the substrate and oligonucleotide shown in FIG. 13A.

The results of the cleavage reaction is shown in FIG. 13B. The reaction was run either in the presence or absence of DNAPTaq or pilot oligonucleotide as indicated in FIG. 13B.

Strikingly, in the case of RNA cleavage, a 3' arm is not required for the pilot oligonucleotide. It is very unlikely that this cleavage is due to previously described RNaseH, which would be expected to cut the RNA in several places along the 30 base-pair long RNA-DNA duplex. The 5' nuclease of DNAPTaq is a structure-specific RNaseH that cleaves the RNA at a single site near the 5' end of the heteroduplexed region.

It is surprising that an oligonucleotide lacking a 3' arm is able to act as a pilot in directing cleavage of an RNA target because such oligonucleotides are unable to direct cleavage of DNA targets using native DNAPs. However, some modified DNAPs, for example, clone 4E described below, can cleave DNA in the absence of a 3' arm.

We tested whether cleavage of an RNA template by DNAPTaq in the presence of a fully complementary primer could help explain why DNAPTaq is unable to extend a DNA oligonucleotide on an RNA template, in a reaction resembling that of reverse transcriptase. Another thermophilic DNAP, DNAPTth, is able to use RNA as a template, but only in the presence of Mn++, so we predicted that this enzyme would not cleave RNA in the presence of this cation. Accordingly, we incubated an RNA molecule with an appropriate pilot oligonucleotide in the presence of DNAPTaq or DNAPTth, in buffer containing either Mg++ or Mn++. As expected, both enzymes cleaved the RNA in the presence of Mg++. However, DNAPTaq, but not DNAPTth, degraded the RNA in the presence of Mn++. We conclude that the 5' nuclease activities of many DNAPs may contribute to their inability to use RNA as templates.

EXAMPLE 2

Generation of Modified Thermostable DNA Polymerases

Thermostable DNA polymerases were generated which have reduced synthetic activity, an activity that is an undesirable side-reaction during DNA cleavage in the detection assay of the invention, yet have maintained thermostable nuclease activity. The result is a thermostable polymerase which cleaves nucleic acids DNA with extreme specificity.

Type A DNA polymerases from eubacteria of the genus Thermus share extensive protein sequence identity (90% in the polymerization domain, using the Lipman-Pearson method in the DNA analysis software from DNAStar, WI) and behave similarly in both polymerization and nuclease assays. Therefore, we have used the genes for the DNA polymerase of *Thermus aquaticus* (DNAPTaq) and *Thermus flavus* (DNAPTfl) as representatives of this class. Polymerase genes from other eubacterial organisms, such as *Thermus thermophilus, Thermus sp., Thermotoga maritima, Thermosipho africanus* and *Bacillus stearothermophilus* are equally suitable. The DNA polymerases from these thermophilic organisms are capable of surviving and performing at elevated temperatures, and can thus be used in reactions in which temperature is used as a selection against non-specific hybridization of nucleic acid strands.

The restriction sites used for deletion mutagenesis, described below, were chosen for convenience. Different sites situated with similar convenience are available in the Thermus thermophilus gene and can be used to make similar constructs with other Type A polymerase genes from related organisms.

A. Creation of Constructs Containing Modified DNA Polymerase Genes

1. Modified DNAPTaq Genes

The first step in our procedure was to place a modified gene for the Taq DNA polymerase on a plasmid under control of an inducible promoter. The modified Taq polymerase gene was isolated as follows: The Taq DNA polymerase gene was amplified by polymerase chain reaction from genomic DNA from *Thermus aquaticus*, strain YT-1 (Lawyer et al., supra), using as primers the oligonucleotides described in SEQ ID NOS:13–14. The resulting fragment of DNA has a recognition sequence for the restriction endonuclease EcoRI at the 5' end of the coding sequence and a BglII sequence at the 3' end. Cleavage with BglII leaves a 5' overhang or "sticky end" that is compatible with the end generated by BamHI. The PCR-amplified DNA was digested with EcoRI and BamHI. The 2512 bp fragment containing the coding region for the polymerase gene was gel purified and then ligated into a plasmid which contains an inducible promoter.

In one embodiment of the invention, the pTTQ 18 vector, which contains the hybrid trp-lac (tac) promoter, was used [M. J. R. Stark, Gene 5:255 (1987)] and shown in FIG. 14. The tac promoter is under the control of the *E. coli* lac repressor. Repression allows the synthesis of the gene product to be suppressed until the desired level of bacterial growth has been achieved, at which point repression is removed by addition of a specific inducer, isopropyl-β-D-thiogalactopyranoside (IPTG). Such a system allows the expression of foreign proteins that may slow or prevent growth of transformants.

Figures 15A, 15B, 15C:
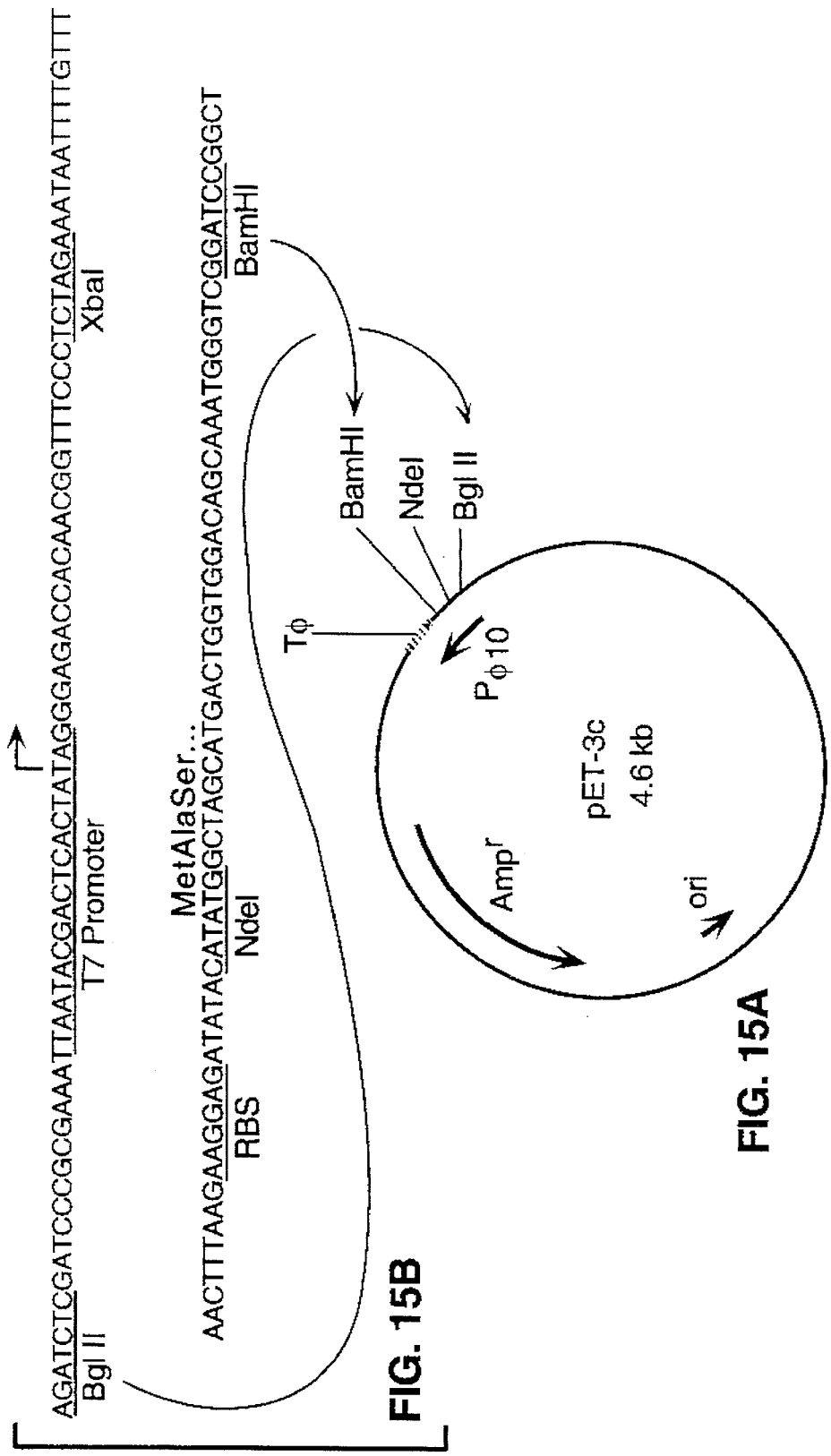
FIG. 15 is a diagram of vector pET-3c.

Bacterial promoters, such as tac, may not be adequately suppressed when they are present on a multiple copy plasmid. If a highly toxic protein is placed under control of such a promoter, the small amount of expression leaking through can be harmful to the bacteria. In another embodiment of the invention, another option for repressing synthesis of a cloned gene product was used. The non-bacterial promoter, from bacteriophage T7, found in the plasmid vector series pET-3 was used to express the cloned mutant Taq polymerase genes [FIG. 15; Studier and Moffatt, J. Mol. Biol. 189:113 (1986)]. This promoter initiates transcription only by T7 RNA polymerase. In a suitable strain, such as BL21(DE3)pLYS, the gene for this RNA polymerase is carded on the bacterial genome under control of the lac operator. This arrangement has the advantage that expression of the multiple copy gene (on the plasmid) is completely dependent on the expression of T7 RNA polymerase, which is easily suppressed because it is present in a single copy.

For ligation into the pTTQ18 vector (FIG. 14), the PCR product DNA containing the Taq polymerase coding region (mutTaq, clone 4B, SEQ ID NO:21) was digested with EcoRI and BglII and this fragment was ligated under standard "sticky end" conditions [Sambrook et al. *Molecular Cloning,* Cold Spring Harbor Laboratory Press, Cold Spring Harbor, pp. 1.63–1.69 (1989)] into the EcoRI and BamHI sites of the plasmid vector pTTQ18. Expression of this construct yields a translational fusion product in which the first two residues of the native protein (Met-Arg) are replaced by three from the vector (Met-Asn-Ser), but the remainder of the natural protein would not change. The construct was transformed into the JM109 strain of *E. coli* and the transformants were plated under incompletely repressing conditions that do not permit growth of bacteria expressing the native protein. These plating conditions allow the isolation of genes containing pre-existing mutations, such as those that result from the infidelity of Taq polymerase during the amplification process.

Using this amplification/selection protocol, we isolated a clone (depicted in FIG. 4B) containing a mutated Taq polymerase gene (mutTaq, clone 4B). The mutant was first detected by its phenotype, in which temperature-stable 5' nuclease activity in a crude cell extract was normal, but polymerization activity was almost absent (approximately less than 1% of wild type Taq polymerase activity).

DNA sequence analysis of the recombinant gene showed that it had changes in the polymerase domain resulting in two amino acid substitutions: an A to G change at nucleotide position 1394 causes a Glu to Gly change at amino acid position 465 (numbered according to the natural nucleic and amino acid sequences, SEQ ID NOS: I and 4) and another A to G change at nucleotide position 2260 causes a Gln to Arg change at amino acid position 754. Because the Gln to Gly mutation is at a nonconserved position and because the Glu to Arg mutation alters an amino acid that is conserved in virtually all of the known Type A polymerases, this latter mutation is most likely the one responsible for curtailing the synthesis activity of this protein. The nucleotide sequence for the FIG. 4B construct is given in SEQ ID NO:21.

Subsequent derivatives of DNAPTaq constructs were made from the mutTaq gene, thus, they all bear these amino acid substitutions in addition to their other alterations, unless these particular regions were deleted. These mutated sites are indicated by black boxes at these locations in the diagrams in FIG. 4. All constructs except the genes shown in FIGS. 4E and F were made in the pTTQ18 vector.

The cloning vector used for the genes in FIGS. 4E and F was from the pET-3 series, described above. Though this vector series has only a BamHI site for cloning downstream of the T7 promoter, the series contains variants that allow cloning into any of the three reading frames. For cloning of the PCR product described above, the variant called pET-3c was used (FIG. 15). The vector was digested with BamHI, dephosphorylated with calf intestinal phosphatase, and the sticky ends were filled in using the Klenow fragment of DNAPEcl and dNTPs. The gene for the mutant Taq DNAP shown in FIG. 4B (mutTaq, clone 4B) was released from pTTQ18 by digestion with EcoRI and SalI, and the "sticky ends" were filled in as was done with the vector. The fragment was ligated to the vector under standard blunt-end conditions (Sambrook et al., *Molecular Cloning*, supra), the construct was transformed into the BL21(DE3)pLYS strain of *E. coli*, and isolates were screened to identify those that were ligated with the gene in the proper orientation relative to the promoter. This construction yields another translational fusion product, in which the first two amino acids of DNAPTaq (Met-Arg) are replaced by 13 from the vector plus two from the PCR primer (Met-Ala-Ser-Met-Thr-Gly-Gly-Gln-Gln-Met-Gly-Arg-Ile-Asn-Ser)(SEQ ID NO:29).

Our goal was to generate enzymes that lacked the ability to synthesize DNA, but retained the ability to cleave nucleic acids with a 5' nuclease activity. The act of primed, templated synthesis of DNA is actually a coordinated series of events, so it is possible to disable DNA synthesis by disrupting one event while not affecting the others. These steps include, but are not limited to, primer recognition and binding, dNTP binding and catalysis of the inter-nucleotide phosphodiester bond. Some of the amino acids in the polymerization domain of DNAPEcI have been linked to these functions, but the precise mechanisms are as yet poorly defined.

One way of destroying the polymerizing ability of a DNA polymerase is to delete all or part of the gene that encodes that domain for the protein, or to otherwise render the gene incapable of making a complete polymerization domain. Individual mutant enzymes may differ from each other in stability and solubility both inside and outside cells. For instance, in contrast to the 5' nuclease domain of DNAPEcI, which can be released in an active form from the polymerization domain by gentle proteolysis [Setlow and Kornberg, J. Biol. Chem. 247:232 (1972)], the Thermus nuclease domain, when treated similarly, becomes less soluble and the cleavage activity is often lost.

Using the mutant gene shown in FIG. 4B as starting material, several deletion constructs were created. All cloning technologies were standard (Sambrook et al., supra) and are summarized briefly, as follows:

FIG. 4C: The mutTaq construct was digested with PstI, which cuts once within the polymerase coding region, as indicated, and cuts immediately downstream of the gene in the multiple cloning site of the vector. After release of the fragment between these two sites, the vector was re-ligated, creating an 894-nucleotide deletion, and bringing into frame a stop codon 40 nucleotides downstream of the junction. The nucleotide sequence of this modified polymerase (clone 4C) is given in SEQ ID NO:9.

FIG. 4D: The mutTaq construct was digested with NheI, which cuts once in the gene at position 2047. The resulting four-nucleotide 5' overhanging ends were filled in, as described above, and the blunt ends were re-ligated. The resulting four-nucleotide insertion changes the reading frame and causes termination of translation ten amino acids downstream of the mutation. The nucleotide sequence of this modified polymerase (clone 4D) is given in SEQ ID NO:10.

FIG. 4E: The entire mutTaq gene was cut from pTTQ18 using EcoRI and SalI and cloned into pET-3c, as described above. This clone was digested with BstXI and XcmI, at unique sites that are situated as shown in FIG. 4E. The DNA was treated with the Klenow fragment of DNAPEcl and dNTPs, which resulted in the 3' overhangs of both sites being trimmed to blunt ends. These blunt ends were ligated together, resulting in an out-of-frame deletion of 1540 nucleotides. An in-frame termination codon occurs 18 triplets past the junction site. The nucleotide sequence of this modified polymerase (clone 4E) is given in SEQ ID NO:11.

FIG. 4F: The entire mutTaq germ was cut from pTTQ18 using EcoRI and SalI and cloned into pET-3c, as described above. This clone was digested with BstXI and BamHi, at unique sites that are situated as shown in the diagram. The DNA was treated with the Klenow fragment of DNAPEcl and dNTPs, which resulted in the 3' overhang of the BstX I site being trimmed to a blunt end, while the 5' overhang of the Bam HI site was filled in to make a blunt end. These ends were ligated together, resulting in an in-frame deletion of 903 nucleotides. The nucleotide sequence of the modified polymerase (clone 4F) is given in SEQ ID NO:12.

2. Modified DNAPTfl Gene

The DNA polymerase gene of *Thermus flavus* was isolated from the "*T. flavus*" AT-62 strain obtained from the American Type Tissue Collection (ATCC 33923). This strain has a different restriction map then does the *T. flavus* strain used to generate the sequence published by Akhmetzjanov and Vakhitov, supra. The published sequence is listed as SEQ ID NO 2. No sequence data has been published for the DNA polymerase gene from the AT-62 strain of *T. flavus*.

Genomic DNA from *T. flavus* was amplified using the same primers used to amplify the *T. aquaticus* DNA polymerase gene (SEQ ID NOS:13–14). The approximately 2500 base pair PCR fragment was digested with EcoRI and BamHI. The over-hanging ends were made blunt with the Klenow fragment of DNAPEcl and dNTPs. The resulting approximately 1800 base pair fragment containing the coding region for the N-terminus was ligated into pET-3c, as described above. This construct, clone 5B, is depicted in FIG. 5B. The wild type *T. flavus* DNA polymerase gene is depicted in FIG. 5A. The 5B clone has the same leader amino acids as do the DNAPTaq clones 4E and F which were cloned into pET-3c; it is not known precisely where translation termination occurs, but the vector has a strong transcription termination signal immediately downstream of the cloning site.

B. Growth and Induction of Transformed Cells

Bacterial cells were transformed with the constructs described above using standard transformation techniques and used to inoculate 2 mls of a standard growth medium (e.g., Luria-Bertani broth). The resulting cultures were incubated as appropriate for the particular strain used, and induced if required for a particular expression system. For all of the constructs depicted in FIGS. 4 and 5, the cultures were grown to an optical density (at 600 nm wavelength) of 0.5 OD.

To induce expression of the cloned genes, the cultures were brought to a final concentration of 0.4 mM IPTG and the incubations were continued for 12 to 17 hours. 50 µl aliquots of each culture were removed both before and after induction and were combined with 20 µl of a standard gel loading buffer for sodium dodecyl sulfate-polyacrylamide gel electrophoresis (SDS-PAGE). Subsequent staining with Coomassie Blue (Sambrook et al., supra) allows visualization of the foreign proteins if they account for about 3–5% of the cellular protein and do not co-migrate with any of the major $E.$ $coli$ protein bands. Proteins that do co-migrate with a major host protein must be expressed as more than 10% of the total protein to be seen at this stage of analysis.

C. Heat Lysis and Fractionation

Expressed thermostable proteins, i.e., the modified polymerases, were isolated by heating crude bacterial cell extracts to cause denaturation and precipitation of the less stable $E.$ $coli$ proteins. The precipitated $E.$ $coli$ proteins were then, along with other cell debris, removed by centrifugation. 1.7 mls of the culture were pelleted by microcentrifugation at 12,000 to 14,000 rpm for 30 to 60 seconds. After removal of the supernatant, the cells were resuspended in 400 µl of buffer A (50 mM Tris-HCl, pH 7.9, 50 mM dextrose, 1 mM EDTA), re-centrifuged, then resuspended in 80 µl of buffer A with 4mg/ml lysozyme. The cells were incubated at room temperature for 15 minutes, then combined with 80 µl of buffer B (10 mM Tris-HCl, pH 7.9, 50 mM KCl, 1 mM EDTA, 1 mM phenylmethylsulfonyl fluoride (PMSF), 0.5% Tween-20, 0.5% Nonidet-P40).

This mixture was incubated at 75° C. for 1 hour to denature and precipitate the host proteins. This cell extract was centrifuged at 14,000 rpm for 15 minutes at 4° C., and the supernatant was transferred to a fresh tube. An aliquot of 0.5 to 1 µl of this supernatant was used directly in each test reaction, and the protein content of the extract was determined by subjecting 7 µl to electrophoretic analysis, as above. The native recombinant Taq DNA polymerase [Englke, Anal. Biochem 191:396 (1990)], and the double point mutation protein shown in FIG. 4B are both soluble and active at this point.

The foreign protein may not be detected after the heat treatments due to sequestration of the foreign protein by the cells into inclusion bodies. These are granules that form in the cytoplasm when bacteria are made to express high levels of a foreign protein, and they can be purified from a crude lysate, and analyzed SDS PAGE to determine their protein content. Many methods have been described in the literature, and one approach is described below.

D. Isolation and Solubilization of Inclusion Bodies

A small culture was grown and induced as described above. A 1.7 ml aliquot was pelleted by brief centrifugation, and the bacterial cells were resuspended in 100 of Lysis buffer (50 mM Tris-HCl, pH 8.0, 1 mM EDTA, 100 mM NaCl). 2.5 µl of 20 mM PMSF were added for a final concentration of 0.5 mM, and lysozyme was added to a concentration of 1.0 mg/ml. The cells were incubated at room temperature for 20 minutes, deoxycholic acid was added to 1 mg/ml (1 µl of 100 mg/ml solution), and the mixture was further incubated at 37° C. for about 15 minutes or until viscous. DNAse I was added to 10 µg/ml and the mixture was incubated at room temperature for about 30 minutes or until it was no longer viscous.

From this mixture the inclusion bodies were collected by centrifugation at 14,000 rpm for 15 minutes at 4° C., and the supernatant was discarded. The pellet was resuspended in 100 µl of lysis buffer with 10 mM EDTA (pH 8.0) and 0.5% Triton X- 100. After 5 minutes at room temperature, the inclusion bodies were pelleted as before, and the supernatant was saved for later analysis. The inclusion bodies were resuspended in 50 µl of distilled water, and 5 µl was combined with SDS gel loading buffer (which dissolves the inclusion bodies) and analyzed electrophoretically, along with an aliquot of the supernatant.

If the cloned protein is found in the inclusion bodies, it may be released to assay the cleavage and polymerase activities and the method of solubilization must be compatible with the particular activity. Different methods of solubilization may be appropriate for different proteins, and a variety of methods are discussed in Molecular Cloning (Sambrook et al., supra). The following is an adaptation we have used for several of our isolates.

20 µl of the inclusion body-water suspension were pelleted by centrifugation at 14,000 rpm for 4 minutes at room temperature, and the supernatant was discarded. To further wash the inclusion bodies, the pellet was resuspended in 20µl of lysis buffer with 2M urea, and incubated at room temperature for one hour. The washed inclusion bodies were then resuspended in 2 µl of lysis buffer with 8M urea; the solution clarified visibly as the inclusion bodies dissolved. Undissolved debris was removed by centrifugation at 14,000 rpm for 4 minutes at room temperature, and the extract supernatant was transferred to a fresh tube.

To reduce the urea concentration, the extract was diluted into $KH_2PO_4$. A fresh tube was prepared containing 180 µl of 50 mM $KH_2PO_4$, pH 9.5, 1 mM EDTA and 50 mM NaCl. A 2 µl aliquot of the extract was added and vortexed briefly to mix. This step was repeated until all of the extract had been added for a total of 10 additions. The mixture was allowed to sit at room temperature for 15 minutes, during which time some precipitate often forms. Precipitates were removed by centrifugation at 14,000 rpm, for 15 minutes at room temperature, and the supernatant was transferred to a fresh tube. To the 200 µl of protein in the $KH_2PO_4$ solution, 140–200 µl of saturated $(NH_4)_2SO_4$ were added, so that the resulting mixture was about 41% to 50% saturated $(NH_4)_2SO_4$. The mixture was chilled on ice for 30 minutes to allow the protein to precipitate, and the protein was then collected by centrifugation at 14,000 rpm, for 4 minutes at room temperature. The supernatant was discarded, and the pellet was dissolved in 20 µl Buffer C (20 mM HEPES, pH 7.9, 1 mM EDTA, 0.5% PMSF, 25 mM KCl and 0.5 % each of Tween-20 and Nonidet P 40). The protein solution was centrifuged again for 4 minutes to pellet insoluble materials, and the supernatant was removed to a fresh tube. The protein contents of extracts prepared in this manner were visualized by resolving 1–4 µl by SDS-PAGE; 0.5 to 1 µl of extract was tested in the cleavage and polymerization assays as described.

E. Protein Analysis for Presence of Nuclease and Synthetic Activity

The modified DNA polymerases described above and shown in FIGS. 4 and 5 were analyzed by the following methods.

1. Structure Specific Nuclease Assay

A candidate modified polymerase is tested for 5' nuclease activity by examining its ability to catalyze structure-specific cleavages. By the term "cleavage structure" as used herein, is meant a nucleic acid structure which is a substrate for cleavage by the 5' nuclease activity of a DNAP.

The polymerase is exposed to test complexes that have the structures shown in FIG. 16. Testing for 5' nuclease activity involves three reactions: 1) a primer-directed cleavage (FIG. 16B) is performed because it is relatively insensitive to variations in the salt concentration of the reaction and can, therefore, be performed in whatever solute conditions the modified enzyme requires for activity; this is generally the same conditions preferred by unmodified polymerases; 2) a similar primer-directed cleavage is performed in a buffer which permits primer-independent cleavage, i.e., a low salt buffer, to demonstrate that the enzyme is viable under these conditions; and 3) a primer-independent cleavage (FIG. 16A) is performed in the same low salt buffer.

The bifurcated duplex is formed between a substrate strand and a template strand as shown in FIG. 16. By the term "substrate strand" as used herein, is meant that strand of nucleic acid in which the cleavage mediated by the 5' nuclease activity occurs. The substrate strand is always depicted as the top strand in the bifurcated complex which serves as a substrate for 5' nuclease cleavage (FIG. 16). By the term "template strand" as used herein, is meant the strand of nucleic acid which is at least partially complementary to the substrate strand and which anneals to the substrate strand to form the cleavage structure. The template strand is always depicted as the bottom strand of the bifurcated cleavage structure (FIG. 16). If a primer (a short oligonucleotide of 19 to 30 nucleotides in length) is added to the complex, as when primer-dependent cleavage is to be tested, it is designed to anneal to the 3' arm of the template strand (FIG. 16B). Such a primer would be extended along the template strand if the polymerase used in the reaction has synthetic activity.

Figure 16B:
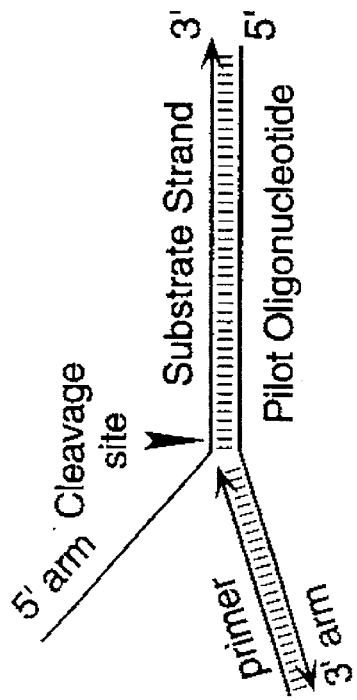
FIGS. 16A–E depicts a set of molecules which are suitable substrates for cleavage by the 5' nuclease activity of DNAPs.
Figure 16D:
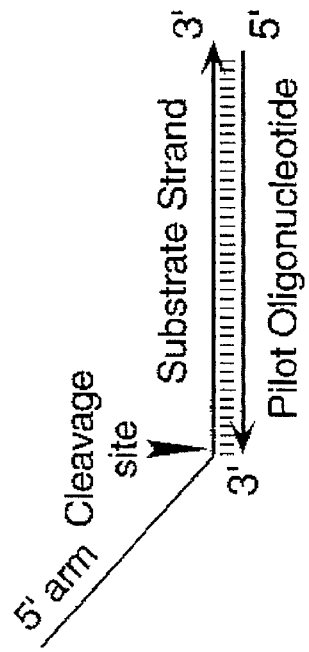
Figure 16A:
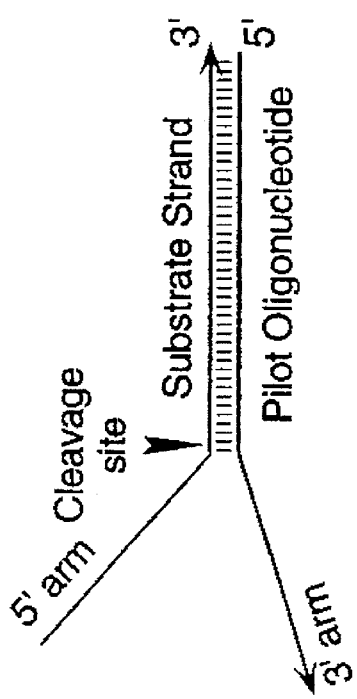
Figure 16C:
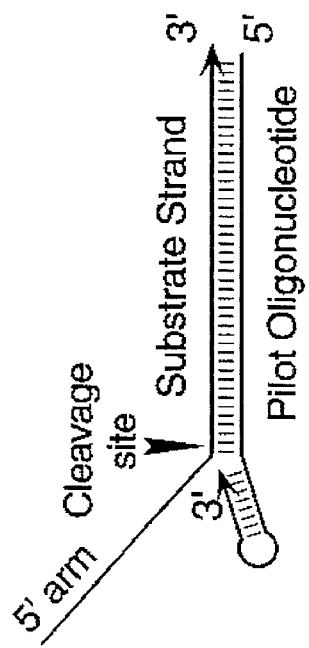
Figure 16E:
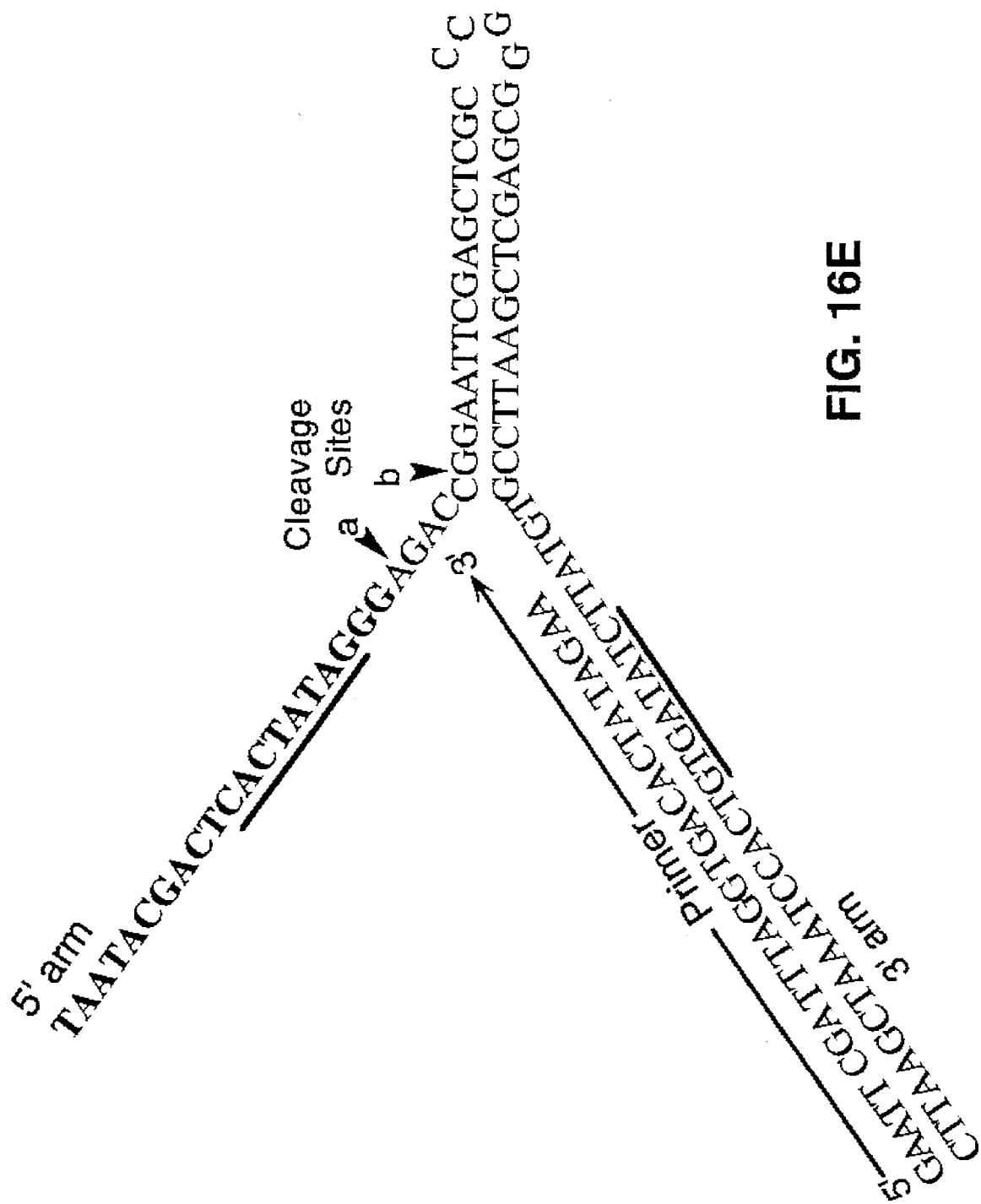

The cleavage structure may be made as a single hairpin molecule, with the 3' end of the target and the 5' end of the pilot joined as a loop as shown in FIG. 16E. A primer oligonucleotide complementary to the 3' arm is also required for these tests so that the enzyme's sensitivity to the presence of a primer may be tested.

Nucleic acids to be used to form test cleavage structures can be chemically synthesized, or can be generated by standard recombinant DNA techniques. By the latter method, the hairpin portion of the molecule can be created by inserting into a cloning vector duplicate copies of a short DNA segment, adjacent to each other but in opposing orientation. The double-stranded fragment encompassing this inverted repeat, and including enough flanking sequence to give short (about 20 nucleotides) unpaired 5' and 3' arms, can then be released from the vector by restriction enzyme digestion, or by PCR performed with an enzyme lacking a 5' exonuclease (e.g., the Stoffel fragment of Amplitaq™ DNA polymerase, Vent™ DNA polymerase).

The test DNA can be labeled on either end, or internally, with either a radioisotope, or with a non-isotopic tag. Whether the hairpin DNA is a synthetic single strand or a cloned double strand, the DNA is heated prior to use to melt all duplexes. When cooled on ice, the structure depicted in FIG. 16E is formed, and is stable for sufficient time to perform these assays.

To test for primer-directed cleavage (Reaction 1), a detectable quantity of the test molecule (typically 1–100 fmol of $^{32}$P-labeled hairpin molecule) and a 10 to 100-fold molar excess of primer are placed in a buffer known to be compatible with the test enzyme. For Reaction 2, where primer-directed cleavage is performed under condition which allow primer-independent cleavage, the same quantities of molecules are placed in a solution that is the same as the buffer used in Reaction 1 regarding pH, enzyme stabilizers (e.g., bovine serum albumin, nonionic detergents, gelatin) and reducing agents (e.g., dithiothreitol, 2-mercaptoethanol) but that replaces any monovalent cation salt with 20 mM KCl; 20 mM KCl is the demonstrated optimum for primer-independent cleavage. Buffers for enzymes, such as DNAPEcl, that usually operate in the absence of salt are not supplemented to achieve this concentration. To test for primer-independent cleavage (Reaction 3) the same quantity of the test molecule, but no primer, are combined under the same buffer conditions used for Reaction 2.

All three test reactions are then exposed to enough of the enzyme that the molar ratio of enzyme to test complex is approximately 1:1. The reactions are incubated at a range of temperatures up to, but not exceeding, the temperature allowed by either the enzyme stability or the complex stability, whichever is lower, up to 80° C. for enzymes from thermophiles, for a time sufficient to allow cleavage (10 to 60 minutes). The products of Reactions 1, 2 and 3 are resolved by denaturing polyacrylamide gel electrophoresis, and visualized by autoradiography or by a comparable method appropriate to the labeling system used. Additional labeling systems include chemiluminescence detection, silver or other stains, blotting and probing and the like. The presence of cleavage products is indicated by the presence of molecules which migrate at a lower molecular weight than does the uncleaved test structure. These cleavage products indicate that the candidate polymerase has structure-specific 5' nuclease activity.

To determine whether a modified DNA polymerase has substantially the same 5' nuclease activity as that of the native DNA polymerase, the results of the above-described tests are compared with the results obtained from these tests performed with the native DNA polymerase. By "substantially the same 5' nuclease activity" we mean that the modified polymerase and the native polymerase will both cleave test molecules in the same manner. It is not necessary that the modified polymerase cleave at the same rate as the native DNA polymerase.

Some enzymes or enzyme preparations may have other associated or contaminating activities that may be functional under the cleavage conditions described above and that may interfere with 5' nuclease detection. Reaction conditions can be modified in consideration of these other activities, to avoid destruction of the substrate, or other masking of the 5' nuclease cleavage and its products. For example, the DNA polymerase I of *E. coli* (Pol I), in addition to its polymerase and 5' nuclease activities, has a 3' exonuclease that can degrade DNA in a 3' to 5' direction. Consequently, when the molecule in FIG. 16E is exposed to this polymerase under the conditions described above, the 3' exonuclease quickly removes the unpaired 3' arm, destroying the bifurcated structure required of a substrate for the 5' exonuclease cleavage and no cleavage is detected. The true ability of Pol I to cleave the structure can be revealed if the 3' exonuclease is inhibited by a change of conditions (e.g., pH), mutation, or by addition of a competitor for the activity. Addition of 500 pmoles of a single-stranded competitor oligonucleotide, unrelated to the FIG. 16E structure, to the cleavage reaction with Pol I effectively inhibits the digestion of the 3' arm of the FIG. 16E structure without interfering with the 5' exonuclease release of the 5' arm. The concentration of the competitor is not critical, but should be high enough to occupy the 3' exonuclease for the duration of the reaction.

Similar destruction of the test molecule may be caused by contaminants in the candidate polymerase preparation. Several sets of the structure specific nuclease reactions may be performed to determine the purity of the candidate nuclease and to find the window between under and over exposure of the test molecule to the polymerase preparation being investigated.

The above described modified polymerases were tested for 5' nuclease activity as follows: Reaction 1 was performed in a buffer of 10 mM Tris-Cl, pH 8.5 at 20° C., 1.5 mM $MgCl_2$ and 50 mM KCl and in Reaction 2 the KCl concentration was reduced to 20 mM. In Reactions 1 and 2, 10 fmoles of the test substrate molecule shown in FIG. 16E were combined with 1 pmole of the indicated primer and 0.5 to 1.0 µl of extract containing the modified polymerase (prepared as described above). This mixture was then incubated for 10 minutes at 55° C. For all of the mutant polymerases tested these conditions were sufficient to give complete cleavage. When the molecule shown in FIG. 16E was labeled at the 5' end, the released 5' fragment, 25 nucleotides long, was conveniently resolved on a 20% polyacrylamide gel (19:1 cross-linked) with 7 M urea in a buffer containing 45 mM Tris-borate pH 8.3, 1.4 mM EDTA. Clones 4C–F and 5B exhibited structure-specific cleavage comparable to that of the unmodified DNA polymerase. Additionally, clone 4E has the added ability to cleave DNA in the absence of a 3' arm as discussed above. Representative cleavage reactions are shown in FIG. 17.

Figure 17:
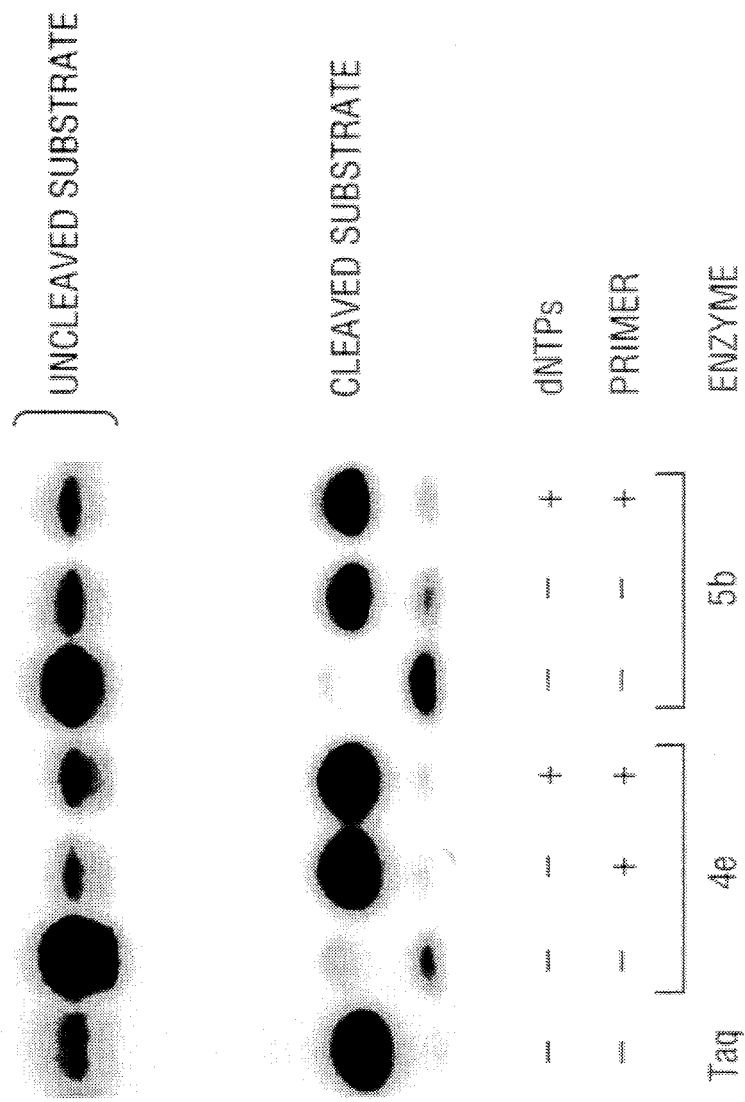
FIG. 17 is an autoradiogram of a gel showing the results of a cleavage reaction run with synthesis-deficient DNAPs.

For the reactions shown in FIG. 17, the mutant polymerase clones 4E (Taq mutant) and 5B (Tfl mutant) were examined for their ability to cleave the hairpin substrate molecule shown in FIG. 16E. The substrate molecule was labeled at the 5' terminus with $^{32}P$. 10 fmoles of heat-denatured, end-labeled substrate DNA and 0.5 units of DNAPTaq (lane 1 ) or 0.5 µl of 4e or 5b extract (FIG. 17, lanes 2–7, extract was prepared as described above) were mixed together in a buffer containing 10 mM Tris-Cl, pH 8.5, 50 mM KCl and 1.5 mM $MgCl_2$. The final reaction volume was 10 µl. Reactions shown in lanes 4 and 7 contain in addition 50 µM of each dNTP. Reactions shown in lanes 3, 4, 6 and 7 contain 0.2 µM of the primer oligonucleotide (complementary to the 3' arm of the substrate and shown in FIG. 16E). Reactions were incubated at 55° C. for 4 minutes. Reactions were stopped by the addition of 8 µl of 95% formamide containing 20 mM EDTA and 0.05% marker dyes per 10 µl reaction volume. Samples were then applied to 12% denaturing acrylamide gels. Following electrophoresis, the gels were audoradiographed. FIG. 17 shows that clones 4E and 5B exhibit cleavage activity similar to that of the native DNAPTaq. Note that some cleavage occurs in these reactions in the absence of the primer. When long hairpin structure, such as the one used here (FIG. 16E), are used in cleavage reactions performed in buffers containing 50 mM KCl a low level of primer-independent cleavage is seen. Higher concentrations of KCl suppress this primer-independent cleavage.

2. Assay for Synthetic Activity in Modified Polymerases

The ability of the modified enzyme or proteolytic fragments is assayed by adding the modified enzyme to an assay system in which a primer is annealed to a template and DNA synthesis is catalyzed by the added enzyme. Many standard laboratory techniques employ such an assay. For example, nick translation and enzymatic sequencing involve extension of a primer along a DNA template by a polymerase molecule.

In a preferred assay for determining the synthetic activity of a modified enzyme an oligonucleotide primer is annealed to a single-stranded DNA template, e.g., bacteriophage M13 DNA, and the primer/template duplex is incubated in the presence of the modified polymerase in question, deoxynucleoside triphosphates (dNTPs) and the buffer and salts known to be appropriate for the unmodified or native enzyme. Detection of either primer extension (by denaturing gel electrophoresis) or dNTP incorporation (by acid precipitation or chromatography) is indicative of an active polymerase. A label, either isotopic or non-isotopic, is preferably included on either the primer or as a dNTP to facilitate detection of polymerization products. Synthetic activity is quantified as the amount of free nucleotide incorporated into the growing DNA chain and is expressed as amount incorporated per unit of time under specific reaction conditions.

Figure 18:
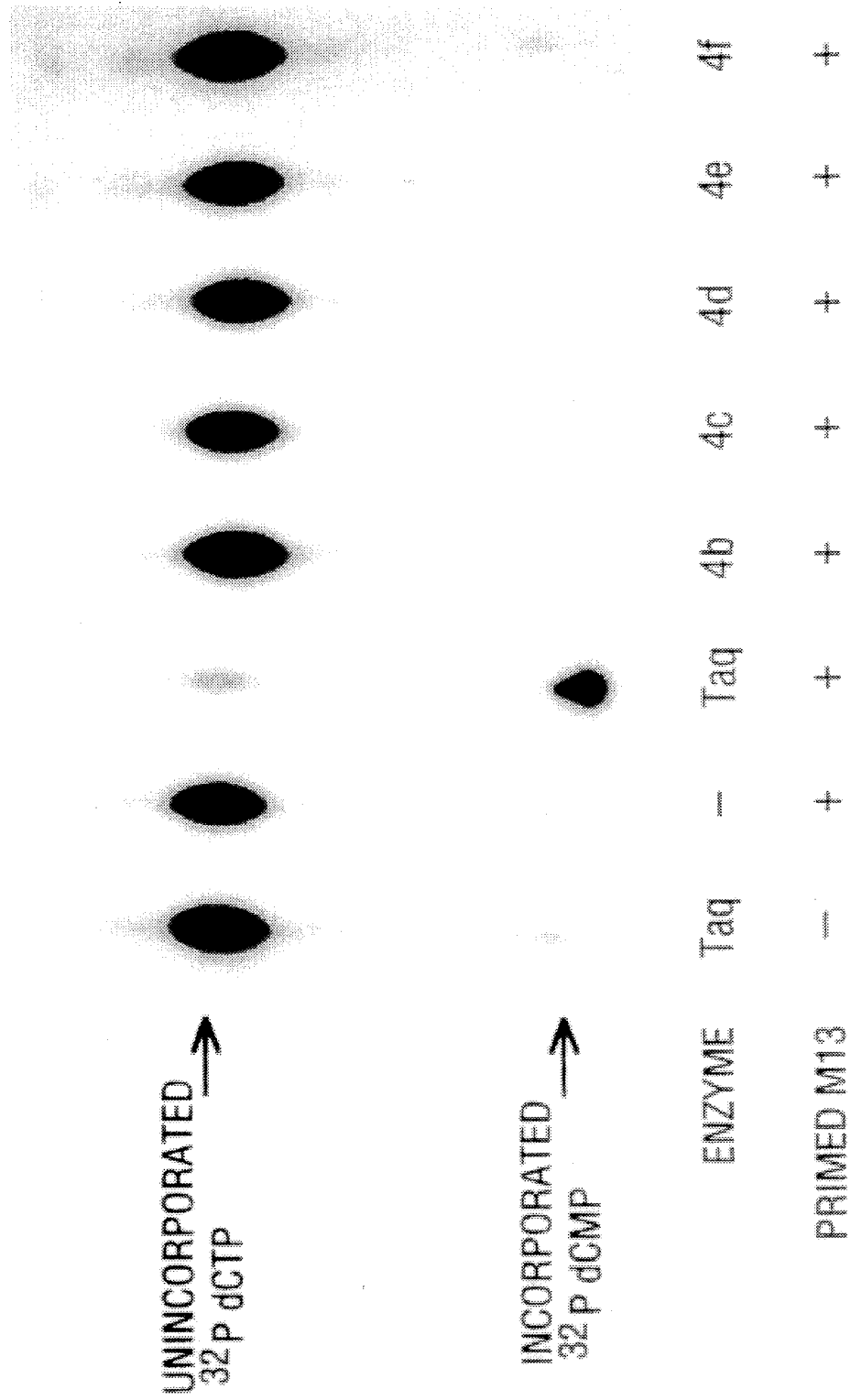
FIG. 18 is an autoradiogram of a PEI chromatogram resolving the products of an assay for synthetic activity in synthesis-deficient DNAPTaq clones.

Representative results of an assay for synthetic activity is shown in FIG. 18. The synthetic activity of the mutant DNAPTaq clones 4B–F was tested as follows: A master mixture of the following buffer was made: 1.2× PCR buffer (1× PCR buffer contains 50 mM KCl, 1.5 mM $MgCl_2$, 10 mM Tris-Cl, ph 8.5 and 0.05% each Tween 20 and Nonidet P40), 50 µM each of dGTP, dATP and dTTP, 5 µM dCTP and 0.125 µM $\alpha$-$^{32}P$-dCTP at 600 Ci/mmol. Before adjusting this mixture to its final volume, it was divided into two equal aliquots. One received distilled water up to a volume of 50 µl to give the concentrations above. The other received 5 µg of single-stranded M13mp18 DNA (approximately 2.5 pmol or 0.05 µM final concentration) and 250 pmol of M13 sequencing primer (5 µM final concentration) and distilled water to a final volume of 50 µl. Each cocktail was warmed to 75° C. for 5 minutes and then cooled to room temperature. This allowed the primers to anneal to the DNA in the DNA-containing mixtures.

For each assay, 4 µl of the cocktail with the DNA was combined with 1 µl of the mutant polymerase, prepared as described, or 1 unit of DNAPTaq (Perkin Elmer) in 1 µl of $dH_2O$. A "no DNA" control was done in the presence of the DNAPTaq (FIG. 18, lane 1 ), and a "no enzyme" control was done using water in place of the enzyme (lane 2). Each reaction was mixed, then incubated at room temperature (approx. 22° C.) for 5 minutes, then at 55° C. for 2 minutes, then at 72° C. for 2 minutes. This step incubation was done to detect polymerization in any mutants that might have optimal temperatures lower than 72° C. After the final incubation, the tubes were spun briefly to collect any condensation and were placed on ice. One µl of each reaction was spotted at an origin 1.5 cm from the bottom edge of a polyethyleneimine (PEI) cellulose thin layer chromatography plate and allowed to dry. The chromatography plate was run in 0.75 M $NaH_2PO_4$, pH 3.5, until the buffer front had run approximately 9 cm from the origin. The plate was dried, wrapped in plastic wrap, marked with luminescent ink, and exposed to X-ray film. Incorporation was detected as counts that stuck where originally spotted, while the unincorporated nucleotides were carded by the salt solution from the origin.

Comparison of the locations of the counts with the two control lanes confirmed the lack of polymerization activity in the mutant preparations. Among the modified DNAPTaq clones, only clone 4B retains any residual synthetic activity as shown in FIG. 18.

EXAMPLE 3

Figure 19A:
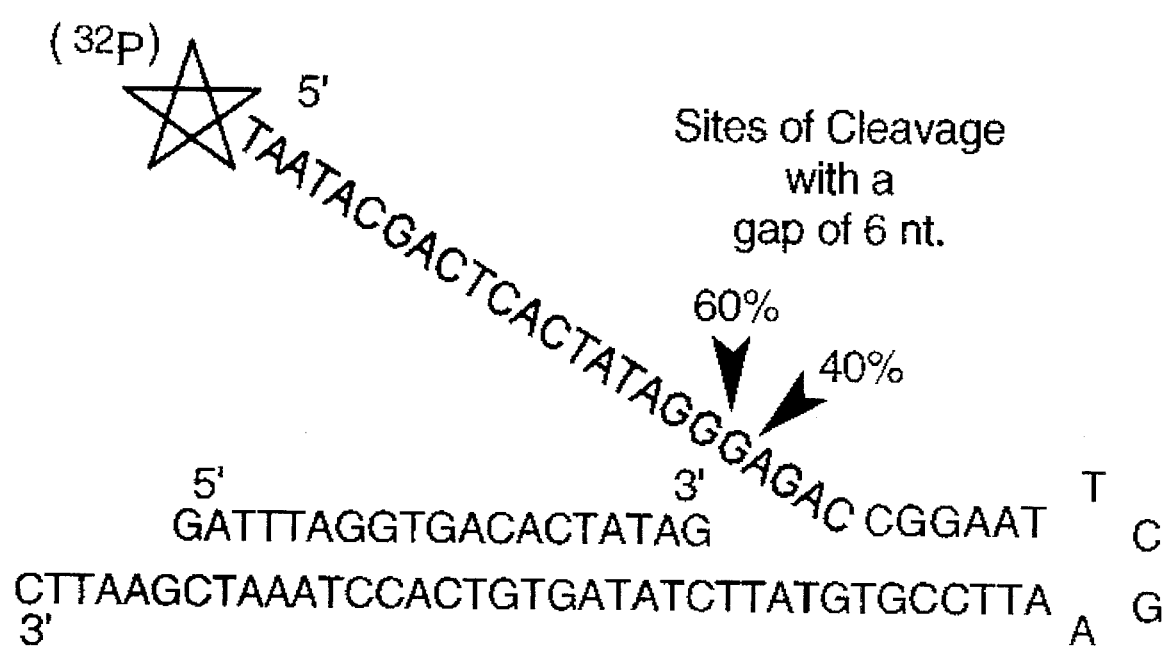
FIG. 19A depicts the substrate molecule used to test the ability of synthesis-deficient DNAPs to cleave short hairpin structures.

Synthesis-Deficient Thermostable DNA Polymerases Can Cleave Short Hairpin Structures with Specificity The ability of the modified polymerases to cleave hairpin structures to generate a cleaved hairpin structure suitable as a detection molecule was examined. The structure and sequence of the hairpin test molecule is shown in FIG. 19A (SEQ ID NO:15). The oligonucleotide (labeled "primer" in FIG. 19A, SEQ ID NO:22) is shown annealed to its complementary sequence on the 3' arm of the hairpin test molecule. The hairpin test molecule was single-end labeled with $^{32}P$ using a labeled T7 promoter primer in a polymerase chain reaction. The label is present on the 5' arm of the hairpin test molecule and is represented by the star in FIG. 19A.

The cleavage reaction was performed by adding 10 fmoles of heat-denatured, end-labeled hairpin test molecule, 0.2 uM of the primer oligonucleotide (complementary to the 3' arm of the hairpin), 50 µM of each dNTP and 0.5 units of DNAPTaq (Perkin Elmer) or 0.5 µl of extract containing a modified polymerase (prepared as described above) in a total volume of 10 µl in a buffer containing 10 mM Tris-Cl, pH 8.5, 50 mM KCl and 1.5 mM $MgCl_2$. Reactions shown in lanes 3, 5 and 7 were run in the absence of dNTPs.

Reactions were incubated at 55° C. for 4 minutes. Reactions were stopped at 55° C. by the addition of 8 µl of 95% formamide with 20 mM EDTA and 0.05% marker dyes per 10 µl reaction volume. Samples were not heated before loading onto denaturing polyacrylamide gels (10% polyacrylamide, 19:1 crosslinking, 7 M urea, 89 mM tris-borate, pH 8.3, 2.8 mM EDTA). The samples were not heated to allow for the resolution of single-stranded and re-duplexed uncleaved hairpin molecules.

Figure 19B:
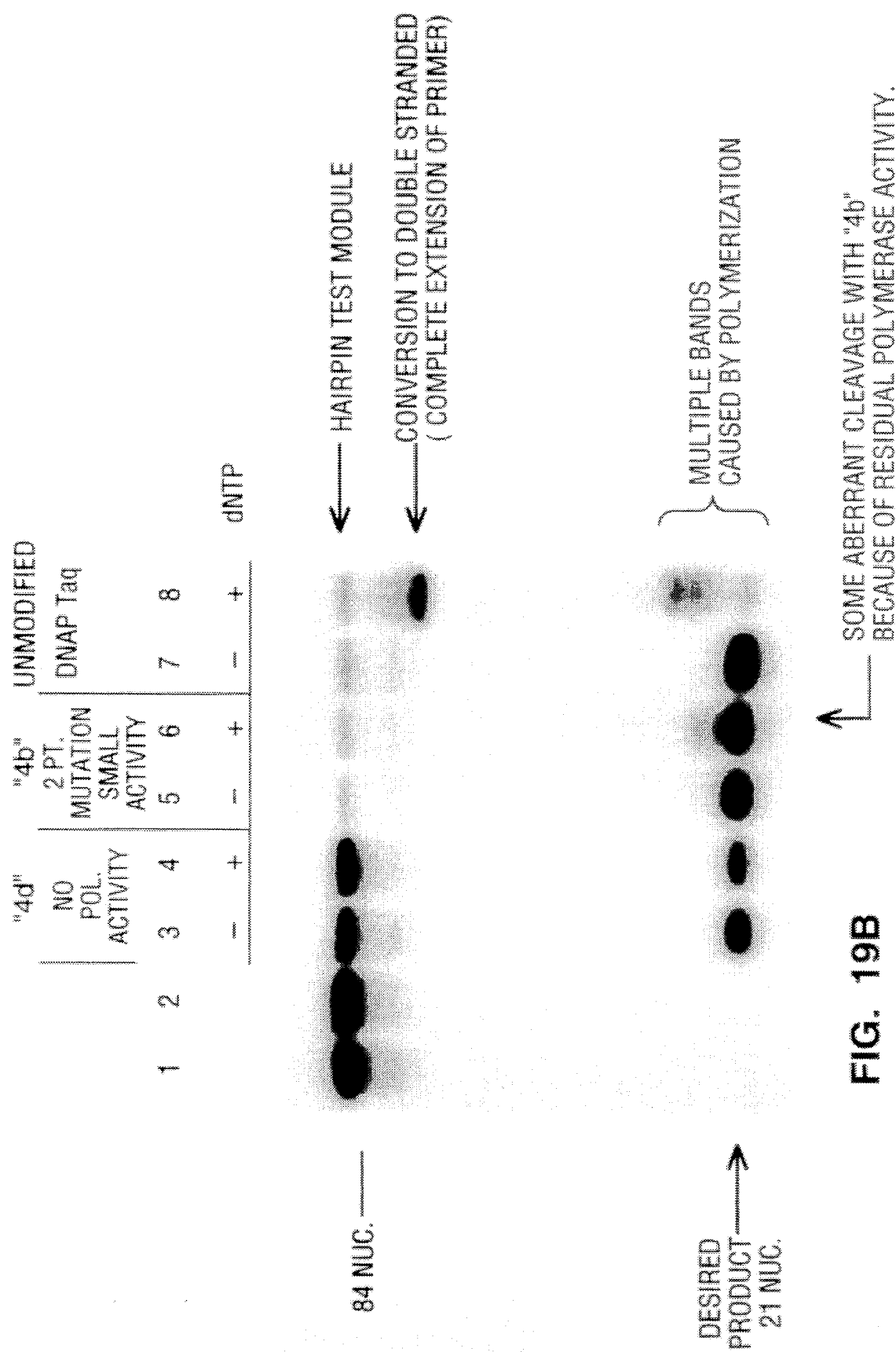
FIG. 19B shows an autoradiogram of a gel resolving the products of a cleavage reaction run using the substrate shown in FIG. 19A.

FIG. 19B shows that altered polymerases lacking any detectable synthetic activity cleave a hairpin structure when an oligonucleotide is annealed to the single-stranded 3' arm of the hairpin to yield a single species of cleaved product (FIG. 19B, lanes 3 and 4). Modified polymerases, such as clone 4D, shown in lanes 3 and 4, produce a single cleaved product even in the presence of dNTPs. Modified polymerases which retain a residual amount of synthetic activity (less than 1% of wild type activity) produce multiple cleavage products as the polymerase can extend the oligonucleotide annealed to the 3' arm of the hairpin thereby moving the site of cleavage (clone 4B, lanes 5 and 6). Native DNATaq produces even more species of cleavage products than do mutant polymerases retaining residual synthetic activity and additionally converts the hairpin structure to a double-stranded form in the presence of dNTPs due to the high level of synthetic activity in the native polymerase (FIG. 19B, lane 8).

EXAMPLE 4

Test of the Trigger/Detection Assay

To test the ability of an oligonucleotide of the type released in the trigger reaction of the trigger/detection assay to be detected in the detection reaction of the assay, the two hairpin structures shown in FIG. 20A were synthesized using standard techniques. The two hairpins are termed the A-hairpin (SEQ ID NO:23) and the T-hairpin (SEQ ID NO:24). The predicted sites of cleavage in the presence of the appropriate annealed primers are indicated by the arrows. The A- and T-hairpins were designed m prevent intra-strand mis-folding by omitting most of the T residues in the A-hairpin and omitting most of the A residues in the T-hairpin. To avoid mis-priming and slippage, the hairpins were designed with local variations in the sequence motifs (e.g., spacing T residues one or two nucleotides apart or in pairs). The A- and T-hairpins can be annealed together to form a duplex which has appropriate ends for directional cloning in pUC-type vectors; restriction sites are located in the loop regions of the duplex and can be used to elongate the stem regions if desired.

The sequence of the test trigger oligonucleotide is shown in FIG. 20B; this oligonucleotide is termed the alpha primer (SEQ ID NO:25). The alpha primer is complementary to the 3' arm of the T-hairpin as shown in FIG. 20A. When the alpha primer is annealed to the T-hairpin, a cleavage structure is formed that is recognized by thermostable DNA polymerases. Cleavage of the T-hairpin liberates the 5' single-stranded arm of the T-hairpin, generating the tau primer (SEQ ID NO:26) and a cleaved T-hairpin (FIG. 20B; SEQ ID NO:27). The tau primer is complementary to the 3' arm of the A-hairpin as shown in FIG. 20A. Annealing of the tau primer to the A-hairpin generates another cleavage structure; cleavage of this second cleavage structure liberates the 5' single-stranded arm of the A-hairpin, generating another molecule of the alpha primer which then is annealed to another molecule of the T-hairpin. Thermocycling releases the primers so they can function in additional cleavage reactions. Multiple cycles of annealing and cleavage are carried out. The products of the cleavage reactions are primers and the shortened hairpin structures shown in FIG. 20C. The shortened or cleaved hairpin structures may be resolved from the uncleaved hairpins by electrophoresis on denaturing acrylamide gels.

The annealing and cleavage reactions are carried as follows: In a 50 µl reaction volume containing 10 mM Tris-Cl, pH 8.5, 1.0 $MgCl_2$, 75 mM KCl, 1 pmole of A-hairpin, 1 pmole T-hairpin, the alpha primer is added at equimolar amount relative to the hairpin structures (1 pmole) or at dilutions ranging from 10- to $10^6$-fold and 0.5 µl of extract containing a modified polymerase (prepared as described above) are added. The predicted melting temperature for the alpha or trigger primer is 60° C. in the above buffer. Annealing is performed just below this predicted melting temperature at 55° C. Using a Perkin Elmer DNA Thermal Cycler, the reactions are annealed at 55° C. for 30 seconds. The temperature is then increased slowly over a five minute period to 72° C. to allow for cleavage. After cleavage, the reactions are rapidly brought to 55° C. (1° C. per second) to allow another cycle of annealing to occur. A range of cycles are performed (20, 40 and 60 cycles) and the reaction products are analyzed at each of these number of cycles. The number of cycles which indicates that the accumulation of cleaved hairpin products has not reached a plateau is then used for subsequent determinations when it is desirable to obtain a quantitative result.

Following the desired number of cycles, the reactions are stopped at 55° C. by the addition of 8 µl of 95% formamide with 20 mM EDTA and 0.05% marker dyes per 10 µl reaction volume. Samples are not heated before loading onto denaturing polyacrylamide gels (10% polyacrylamide, 19:1 crosslinking, 7 M urea, 89 mM tris-borate, pH 8.3, 2.8 mM EDTA). The samples were not heated to allow for the resolution of single-stranded and re-duplexed uncleaved hairpin molecules.

The hairpin molecules may be attached to separate solid support molecules, such as agarose, styrene or magnetic beads, via the 3' end of each hairpin. A spacer molecule may be placed between the 3' end of the hairpin and the bead if so desired. The advantage of attaching the hairpins to a solid support is that this prevents the hybridization of the A- and T-hairpins to one another during the cycles of melting and annealing. The A- and T-hairpins are complementary to one another (as shown in FIG. 20D) and if allowed to anneal to one another over their entire lengths this would reduce the amount of hairpins available for hybridization to the alpha and tau primers during the detection reaction.

Modified thermostable polymerases are used in this assay because they lack significant synthetic activity. The lack of synthetic activity results in the production of a single cleaved hairpin product (as shown in FIG. 19B, lane 4). Multiple cleavage products may be generated by 1) the presence of interfering synthetic activity (see FIG. 19B, lanes 6 and 8) or 2) the presence of primer-independent cleavage in the reaction. Primer-independent cleavage is that cleavage which occurs at sites along the single-stranded 3' arm of the hairpin but not at the primer-dependent cleavage site at the fork of the 3' arm and the double-stranded region of the hairpin. The presence of primer-independent cleavage is detected in the trigger/detection assay by the presence of different sized products at the fork of the cleavage structure. Primer-independent cleavage can be dampened or repressed, when present, by the use of uncleavable nucleotides in the fork region of the hairpin molecule. For example, thiolated nucleotides can be used to replace several nucleotides at the fork region to prevent primer-independent cleavage.

From the above, it should be clear that the present invention provides a cleaving enzyme having 5' nuclease activity without interfering nucleic acid synthetic ability. While having various uses, the enzyme is employed with success in a method of detecting specific target DNAs which does not need to amplify the sample DNA first. Thus, the invention provides an important improvement in nucleic acid detection technology.

We claim:

1. A non-naturally occurring oligonucleotide having a nucleotide sequence encoding a non-naturally occurring thermostable DNA polymerase altered in sequence relative to the naturally occurring sequence of a thermostable DNA polymerase of the genus Thermus such that it exhibits reduced DNA synthetic activity from that of the naturally occurring DNA polymerase, wherein said encoded non-naturally occurring thermostable DNA polymerase exhibits substantially the same 5' nuclease activity as said naturally occurring DNA polymerase.

2. The oligonucleotide of claim 1 comprising the oligonucleotide sequence of SEQ ID NO:21.

3. The oligonucleotide of claim 1 comprising an oligonucleotide sequence selected from the group consisting of SEQ ID NOS:9, 11 and 12.

4. The oligonucleotide of claim 1 comprising the oligonucleotide sequence of SEQ ID NO:10.

5. A recombinant DNA vector comprising DNA having a nucleotide sequence encoding a non-naturally occurring thermostable DNA polymerase altered in sequence relative to the naturally occurring sequence of a thermostable DNA polymerase of the genus Thermus such that it exhibits reduced DNA synthetic activity from that of the naturally occurring DNA polymerase wherein said encoded non-naturally occurring thermostable DNA polymerase exhibits substantially the same 5' nuclease activity as said naturally occurring DNA polymerase.

6. The recombinant DNA vector of claim 5 wherein said nucleotide sequence encoding said altered thermostable DNA polymerase comprises the nucleotide sequence of SEQ ID NO:21.

7. The recombinant DNA vector of claim 5 wherein said nucleotide sequence comprises a nucleotide sequence selected from the group consisting of SEQ ID NOS:9, 11 and 12.

8. The recombinant DNA vector of claim 5 wherein said nucleotide sequence comprises the nucleotide sequence of SEQ ID NO:10.

9. A host cell transformed with the recombinant vector of claim 5.

* * * * *

UNITED STATES PATENT AND TRADEMARK OFFICE
CERTIFICATE OF CORRECTION

PATENT NO. : 5,541,311
DATED : 07/30/96
INVENTOR(S) : JAMES E. DAHLBERG ET AL.

It is certified that error appears in the above-indentified patent and that said Letters Patent is hereby corrected as shown below:

Col. 1, line 6, please delete "vital" and insert --viral--.

Col. 1, line 61, please delete "Them" and insert --There--.

Col. 8, line 17, please delete "(SEQ ID NO:4)" and insert --(SEQ ID NO:7)--.

Col. 9, lines 65-66, please delete "Lawyer et al., J. Biol Chem. Sci., 12:288 (1987)".

Col. 10, line 9, please delete "17" and insert --19--.

Col. 14, line 23, please delete "forth" and insert --fourth--.

Col. 22, line 17, please delete "Tris.Cl" and insert --Tris•Cl--.

Col. 22, line 22, please delete "Tris.Borate" and insert --Tris•Borate--.

Col. 24, line 62, please insert --[-- before "DNAPTli".

Col. 25, line 5, please delete "Tris. Cl" and insert --Tris•Cl--.

Col. 28, line 31, please delete "carded" and insert --carried--.

UNITED STATES PATENT AND TRADEMARK OFFICE
CERTIFICATE OF CORRECTION

PATENT NO. : 5,541,311
DATED : 07/30/96
INVENTOR(S) : JAMES E. DAHLBERG ET AL.

It is certified that error appears in the above-indentified patent and that said Letters Patent is hereby corrected as shown below:

Col. 30, line 32, please delete "germ" and insert --gene--.

Col. 30, line 34, please delete "BamHi" and insert --BamHI--.

Signed and Sealed this

Twenty-fourth Day of February, 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,541,311
DATED : 07/30/96
INVENTOR(S) : JAMES E. DAHLBERG ET AL.

It is certified that error appears in the above-identified patent and that said Letters Patent is hereby corrected as shown below:

In Column 1, line 7, please insert as a new paragraph under the reference to prior applications--The invention was made with Government support under GM 30220, awarded by the National Institutes of Health. The Government has certain rights in the invention.--.

Signed and Sealed this

Twentieth Day of June, 2000

Attest:

Q. TODD DICKINSON

Attesting Officer

Director of Patents and Trademarks

UNITED STATES PATENT AND TRADEMARK OFFICE
CERTIFICATE OF CORRECTION

| | | |
|---|---|---|
| PATENT NO. | : 5,541,311 | Page 1 of 1 |
| APPLICATION NO. | : 08/073384 | |
| DATED | : July 30, 1996 | |
| INVENTOR(S) | : James E. Dahlberg et al. | |

It is certified that error appears in the above-identified patent and that said Letters Patent is hereby corrected as shown below:

Column 1, Please insert before "Filed of Invention" the following paragraph;

--This invention was made with United States Government support under grant number NIH R43 GM30220 awarded by the National Institutes of Health. The United States Government has certain rights in this invention.--

Signed and Sealed this

Twenty-sixth Day of December, 2006

JON W. DUDAS
*Director of the United States Patent and Trademark Office*